(12) United States Patent
Agrawal et al.

(10) Patent No.: US 9,828,601 B2
(45) Date of Patent: Nov. 28, 2017

(54) COMPOSITIONS FOR INHIBITING CHECKPOINT GENE EXPRESSION AND USES THEREOF

(71) Applicant: Idera Pharmaceuticals, Inc., Cambridge, MA (US)

(72) Inventors: Sudhir Agrawal, Shrewsbury, MA (US); Wayne Jiang, Waltham, MA (US); Daqing Wang, Bedford, MA (US); Jessica Seitzer, Windham, NH (US); Fu-Gang Zhu, Bedford, MA (US); Xianzhi Mao, Ambler, PA (US)

(73) Assignee: IDERA PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/053,309

(22) Filed: Feb. 25, 2016

(65) Prior Publication Data
US 2016/0251652 A1    Sep. 1, 2016

Related U.S. Application Data

(60) Provisional application No. 62/126,368, filed on Feb. 27, 2015.

(51) Int. Cl.
| | | |
|---|---|---|
| *C07H 21/04* | (2006.01) |
| *C12N 15/11* | (2006.01) |
| *A61K 31/7105* | (2006.01) |
| *A61K 45/06* | (2006.01) |
| *C12N 15/113* | (2010.01) |

(52) U.S. Cl.
CPC .......... *C12N 15/11* (2013.01); *A61K 31/7105* (2013.01); *A61K 45/06* (2013.01); *C12N 15/1138* (2013.01); *C12N 2310/11* (2013.01); *C12N 2310/314* (2013.01); *C12N 2310/51* (2013.01)

(58) Field of Classification Search
None
See application file for complete search history.

(56) References Cited

U.S. PATENT DOCUMENTS

| | | |
|---|---|---|
| 8,431,544 B1 | 4/2013 | Agrawal et al. |
| 8,877,722 B2 | 11/2014 | Agrawal et al. |
| 2013/0142778 A1 | 6/2013 | Agrawal et al. |
| 2016/0101128 A1 | 4/2016 | Wang et al. |

OTHER PUBLICATIONS

Borkner, L., et al., "RNA interference targeting programmed death receptor-1 improves immune functions of tumor-specific T cells," Cancer Immunol Immunother, (2010) 59:1173-1183.
GenBank: BC119179.1, Mus musculus programmed cell death 1, mRNA (cDNA clone MGC:155495 Image:8733928), complete eds. (2006). [Retrieved from the internet Jul. 29, 2016: <http://www.ncbi.nlm.nih.gov/nuccore/111600043/?report=genbank>.

*Primary Examiner* — Kimberly Chong
(74) *Attorney, Agent, or Firm* — Morgan, Lewis & Bockius LLP

(57) ABSTRACT

The present invention is directed to compounds, compositions, and methods useful for modulating PD1, PDL1, IDO1, LAG3, TIM3, CTLA4, IDO2, CEACAM1, OX40, and/or OX40L mRNA or protein expression using gene silencing compounds comprising two or more single stranded antisense oligonucleotides that are linked through their 5'-ends to allow the presence of two or more accessible 3'-ends.

17 Claims, No Drawings

COMPOSITIONS FOR INHIBITING CHECKPOINT GENE EXPRESSION AND USES THEREOF

RELATED APPLICATIONS

This application claims the benefit of U.S. provisional patent application Ser. No. 62/126,368, filed on Feb. 27, 2015, the contents of which are incorporated herein by reference in its entirety.

BACKGROUND OF THE INVENTION

Field of the Invention

The present invention relates to compounds, compositions, and methods of use for the inhibition of checkpoint gene expression or for diagnosing, treating and/or preventing diseases and/or conditions that respond to the inhibition of checkpoint gene expression.

Summary of the Related Art

The immune system is a hosts defense against foreign antigens; however, in order to function properly a variety of checks and balances are required to protect against self-antigens (i.e., autoimmunity) and, at the same time, provide an appropriate response against foreign. Immune-activating and immune-suppressive receptors and ligands provide these regulatory checks and balances (see Pardoll et al., The blockade of immune checkpoints in cancer immunotherapy, Nat. Rev. Canc. 12, 252 (2012)).

Immune checkpoints refer to a group of endogenous immune-suppressive ligands and receptors that are crucial for the maintenance of self-tolerance and the protection of tissues from damage when the immune system is responding to an infection. (see Y. L. Wu, et al., Immunotherapies: The Blockade of Inhibitory Signals, Int. J. Biol. Sci. 8, 1420 (2012)) In response to the induction of an immune response expression of checkpoints increases. These checkpoints act as regulatory feedback to maintain immune homeostasis.

In patients with cancer, tumor mutations give rise to tumor-specific antigens that can be recognized by the immune system, particularly T-cells, leading to elimination of cancer cells. However, to defend themselves, tumor cells can co-opt immune checkpoint pathways to suppress the immune response in the tumor microenvironment and evade the host immune system by inhibiting T cells that might otherwise attack the tumor cells. (see J. F. Grosso & M. N. Jure-Kunkel; CTLA-4 blockade in tumor models: an overview of preclinical and translational research, Cancer Immun. 13, 5 (2013); M. E. Turnis, et al.; Combinatorial immunotherapy: PD-1 may not be LAG-ing behind any more, OncoImmunology 1, 1172 (2012)).

Many previous cancer immunotherapies have likely been limited by these suppressive mechanisms. Thus there is a need to over these immunosuppressive mechanisms in order to enhance antitumor immunotherapy applications.

BRIEF SUMMARY OF THE INVENTION

The present invention is directed to compounds, compositions, and methods useful for modulating PD1, PDL1, IDO1, LAG3, TIM3, CTLA4, IDO2, CEACAM1, OX40, and/or OX40L mRNA or protein expression using gene silencing compounds comprising two or more single stranded antisense oligonucleotides that are linked through their 5'-ends to allow the presence of two or more accessible 3'-ends. The gene silencing compounds according to the invention effectively inhibit or decrease PD1, PDL1, IDO1, LAG3, TIM3, CTLA4, IDO2, CEACAM1, OX40, and/or OX40L mRNA or protein expression.

Provided herein are methods, compounds, and compositions for modulating expression of PD1, PDL1, IDO1, LAG3, TIM3, CTLA4, IDO2, CEACAM1, OX40, and/or OX40L mRNA and protein. In certain embodiments, compounds useful for modulating expression of PD1, PDL1, IDO1, LAG3, TIM3, CTLA4, IDO2, CEACAM1, OX40, and/or OX40L mRNA and protein are gene silencing compounds.

In certain embodiments, modulation can occur in a cell or tissue. In certain embodiments the cell is a tumor cell. In certain embodiments, the tissue is a tumor. In certain embodiments, the cell or tissue is in an animal. In certain embodiments, the animal is a human. In certain embodiments, PD1, PDL1, IDO1, LAG3, TIM3, CTLA4, IDO2, CEACAM1, OX40, and/or OX40L mRNA levels are reduced. In certain embodiments, PD1, PDL1, IDO1, LAG3, TIM3, CTLA4, IDO2, CEACAM1, OX40, and/or OX40L protein levels are reduced. Such reduction can occur in a time-dependent manner or in a dose-dependent manner.

Also provided are methods, compounds, and compositions useful for preventing, treating, and ameliorating diseases, disorders, and conditions. In certain embodiments, such diseases, disorders, and conditions are hyperproliferative diseases, disorders, and conditions. In certain embodiments such hyperproliferative diseases, disorders, and conditions include cancer as well as associated malignancies and metastases.

In certain embodiments, methods of treatment include administering a PD1, PDL1, IDO1, LAG3, TIM3, CTLA4, IDO2, CEACAM1, OX40, and/or OX40L gene silencing compound or composition to an individual in need thereof. In certain embodiments, the gene silencing compound or composition is administered intratumorally.

DETAILED DESCRIPTION OF THE PREFERRED EMBODIMENTS

The invention relates to the therapeutic and prophylactic use of gene silencing compounds, also referred to as $3^{rd}$ generation antisense (3GA) compounds, to down-regulate checkpoint mRNA or protein expression. Such molecules are useful, for example, in providing compositions for modulation of checkpoint gene expression or for treating and/or preventing diseases and/or conditions that are capable of responding to modulation of checkpoint gene expression in patients, subjects, animals or organisms.

The objects of the present invention, the various features thereof, as well as the invention itself may be more fully understood from the following description, when read together with the accompanying drawings in which the following terms have the ascribed meaning. Unless specific definitions are provided, the nomenclature utilized in connection with, and the procedures and techniques of, analytical chemistry, synthetic organic chemistry, and medicinal and pharmaceutical chemistry described herein are those well-known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

The term "2'-O-substituted" means substitution of the 2' position of the pentose moiety with an —O— lower alkyl group containing 1-6 saturated or unsaturated carbon atoms (for example, but not limited to, 2'-O-methyl), or with an —O-aryl or allyl group having 2-6 carbon atoms, wherein such alkyl, aryl or allyl group may be unsubstituted or may be substituted, (for example, with 2'-O-methoxyethyl, ethoxy, methoxy, halo, hydroxyl, trifluoromethyl, cyano, nitro, acyl, acyloxy, alkoxy, carboxyl, carbalkoxyl, or amino groups); or with a hydroxyl, an amino or a halo group, but not with a 2'-H group. In some embodiments the oligonucleotides of the invention include four or five 2'-O-alky nucleotides at their 5' terminus, and/or four or five 2' —O-alky nucleotides at their 3' terminus.

The term "3'", when used directionally, generally refers to a region or position in a polynucleotide or oligonucleotide 3' (toward the 3' end of the nucleotide) from another region or position in the same polynucleotide or oligonucleotide.

The term "3' end" generally refers to the 3' terminal nucleotide of the component oligonucleotides. "Two or more oligonucleotides linked at their 3' ends" generally refers to a linkage between the 3' terminal nucleotides of the oligonucleotides which may be directly via 5', 3' or 2' hydroxyl groups, or indirectly, via a non-nucleotide linker. Such linkages may also be via a nucleoside, utilizing both 2' and 3' hydroxyl positions of the nucleoside. Such linkages may also utilize a functionalized sugar or nucleobase of a 3' terminal nucleotide.

The term "5'", when used directionally, generally refers to a region or position in a polynucleotide or oligonucleotide 5' (toward the 5' end of the nucleotide) from another region or position in the same polynucleotide or oligonucleotide.

The term "5' end" generally refers to the 5' terminal nucleotide of the component oligonucleotides. "Two or more single-stranded antisense oligonucleotides linked at their 5' ends" generally refers to a linkage between the 5' terminal nucleotides of the oligonucleotides which may be directly via 5', 3' or 2' hydroxyl groups, or indirectly, via a non-nucleotide linker. Such linkages may also be via a nucleoside, utilizing both 2' and 3' hydroxyl positions of the nucleoside. Such linkages may also utilize a functionalized sugar or nucleobase of a 5' terminal nucleotide.

The term "about" generally means that the exact number is not critical. Thus, oligonucleotides having one or two fewer nucleoside residues, or from one to several additional nucleoside residues are contemplated as equivalents of each of the embodiments described above.

The term "accessible" generally means when related to a compound according to the invention, that the relevant portion of the molecule is able to be recognized by the cellular components necessary to elicit an intended response to the compound.

The term "agonist" generally refers to a substance that binds to a receptor of a cell and induces a response. An agonist can be a naturally occurring substance such as bacterial DNA or a synthetic composition. A synthetic agonist often mimics the action of a naturally occurring substance such as a ligand.

The term "antigen" generally refers to a substance that is recognized and selectively bound by an antibody or by a T cell antigen receptor. Antigens may include but are not limited to peptides, proteins, lipids, carbohydrates, nucleosides, nucleotides, nucleic acids, and combinations thereof. Antigens may be natural or synthetic and generally induce an immune response that is specific for that antigen.

"Antisense activity" means any detectable or measurable activity attributable to the hybridization of a gene silencing compound to its target nucleic acid. In certain embodiments, antisense activity is a decrease in the amount or expression of a target nucleic acid or protein encoded by such target nucleic acid.

As used herein, "Gene silencing oligonucleotide (GSO)", "Gene silencing compound", or "$3^{rd}$ generation antisense (3GA)" compound are used interchangeably to refer to an oligomeric compound comprising two or more single stranded antisense oligonucleotides that are linked through their 5'-ends to allow the presence of two or more accessible 3'-ends. Gene silencing compounds are capable of undergoing hybridization to a target nucleic acid through hydrogen bonding.

"Antisense inhibition" means reduction of target nucleic acid levels or target protein levels in the presence of a gene silencing compound complementary to a target nucleic acid as compared to target nucleic acid levels or target protein levels in the absence of the gene silencing compound.

"Antisense oligonucleotide" means a single-stranded oligonucleotide having a nucleobase sequence that permits hybridization to a corresponding region or segment of a target nucleic acid.

The term "biologic instability" generally refers to a molecule's ability to be degraded and subsequently inactivated in vivo. For oligonucleotides, such degradation results from exonuclease activity and/or endonuclease activity, wherein exonuclease activity refers to cleaving nucleotides from the 3' or 5' end of an oligonucleotide, and endonuclease activity refers to cleaving phosphodiester bonds at positions other than at the ends of the oligonucleotide.

The term "cancer" generally refers to, without limitation, any malignant growth or tumor caused by abnormal or uncontrolled cell proliferation and/or division. Cancers may occur in humans and/or mammals and may arise in any and all tissues. Treating a patient having cancer may include administration of a compound, pharmaceutical formulation or vaccine according to the invention such that the abnormal or uncontrolled cell proliferation and/or division, or metastasis is affected.

The term "carrier" generally encompasses any excipient, diluent, filler, salt, buffer, stabilizer, solubilizer, oil, lipid, lipid containing vesicle, microspheres, liposomal encapsulation, or other material for use in pharmaceutical formulations. It will be understood that the characteristics of the carrier, excipient or diluent will depend on the route of administration for a particular application. The preparation of pharmaceutically acceptable formulations containing these materials is described in, for example, *Remington's Pharmaceutical Sciences,* 18th Edition, ed. A. Gennaro, Mack Publishing Co., Easton, Pa., 1990.

The term "co-administration" or "co-administered" generally refers to the administration of at least two different substances. Co-administration refers to simultaneous administration, as well as temporally spaced order of up to several days apart, of at least two different substances in any order, either in a single dose or separate doses.

The term "in combination with" generally means administering two or more agents (e.g., a gene silencing compound according to the invention and another agent) such that there is an overlap of an effect of each agent on the patient. Such administration may be done in any order, including simultaneous administration, as well as temporally spaced order from a few seconds up to several days apart. In some embodiments, the administration of the agents are spaced sufficiently close together such that a combinatorial effect is achieved. Such combination treatment may also include more than a single administration of the compound according to the invention and/or independently the other agent. The administration of the compound according to the invention and the other agent may be by the same or different routes. In some embodiments, administration of at least one agent is made while the other agent is still present at a therapeutic level in the subject.

The term "complementary" is intended to mean the capacity for pairing between nucleobases of a first nucleic acid and a second nucleic acid.

"Contiguous nucleobases" means nucleobases immediately adjacent to each other.

The term "individual" or "subject" or "patient" generally refers to a mammal, such as a human.

"CEACAM1 nucleic acid" means any nucleic acid encoding CEACAM1. For example, in certain embodiments, a CEACAM1 nucleic acid includes a DNA sequence encoding CEACAM1, an RNA sequence transcribed from DNA encoding CEACAM1 (including genomic DNA comprising introns and exons), and an mRNA sequence encoding CEACAM1. "CEACAM1 mRNA" means an mRNA encoding a CEACAM1 protein.

"CTLA4 nucleic acid" means any nucleic acid encoding CTLA4. For example, in certain embodiments, a CTLA4 nucleic acid includes a DNA sequence encoding CTLA4, an RNA sequence transcribed from DNA encoding CTLA4 (including genomic DNA comprising introns and exons), and an mRNA sequence encoding CTLA4. "CTLA4 mRNA" means an mRNA encoding a CTLA4 protein.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Hybridization" means the annealing of complementary nucleic acid molecules. In certain embodiments, complementary nucleic acid molecules include an antisense compound and a target nucleic acid.

"IDO1 nucleic acid" means any nucleic acid encoding IDO1. For example, in certain embodiments, a IDO1 nucleic acid includes a DNA sequence encoding IDO1, an RNA sequence transcribed from DNA encoding IDO1 (including genomic DNA comprising introns and exons), and an mRNA sequence encoding IDO1. "IDO1 mRNA" means an mRNA encoding an IDO1 protein.

"IDO2 nucleic acid" means any nucleic acid encoding IDO2. For example, in certain embodiments, a IDO2 nucleic acid includes a DNA sequence encoding IDO2, an RNA sequence transcribed from DNA encoding IDO2 (including genomic DNA comprising introns and exons), and an mRNA sequence encoding IDO2. "IDO2 mRNA" means an mRNA encoding an IDO2 protein.

"Inhibiting PD1, PDL1, IDO1, LAG3, TIM3, CTLA4, IDO2, CEACAM1, OX40, and/or OX40L mRNA or protein expression" means reducing expression of PD1, PDL1, IDO1, LAG3, TIM3, CTLA4, IDO2, CEACAM1, OX40, and/or OX40L mRNA and/or protein levels in the presence of a gene silencing compound according to the invention as compared to expression of PD1, PDL1, IDO1, LAG3, TIM3, CTLA4, IDO2, CEACAM1, OX40, and/or OX40L mRNA and/or protein levels in the absence of a gene silencing compound according to the invention.

The term "kinase inhibitor" generally refers to molecules that antagonize or inhibit phosphorylation-dependent cell signaling and/or growth pathways in a cell. Kinase inhibitors may be naturally occurring or synthetic and include small molecules that have the potential to be administered as oral therapeutics. Kinase inhibitors have the ability to rapidly and specifically inhibit the activation of the target kinase molecules. Protein kinases are attractive drug targets, in part because they regulate a wide variety of signaling and growth pathways and include many different proteins. As such, they have great potential in the treatment of diseases involving kinase signaling, including cancer, cardiovascular disease, inflammatory disorders, diabetes, macular degeneration and neurological disorders. A non-limiting example of a kinase inhibitor is sorafenib.

"LAG3 nucleic acid" means any nucleic acid encoding LAG3. For example, in certain embodiments, a LAG3 nucleic acid includes a DNA sequence encoding LAG3, an RNA sequence transcribed from DNA encoding LAG3 (including genomic DNA comprising introns and exons), and an mRNA sequence encoding LAG3. "LAG3 mRNA" means an mRNA encoding a LAG3 protein.

The term "linear synthesis" generally refers to a synthesis that starts at one end of an oligonucleotide and progresses linearly to the other end. Linear synthesis permits incorporation of either identical or non-identical (in terms of length, base composition and/or chemical modifications incorporated) monomeric units into an oligonucleotide.

The term "mammal" is expressly intended to include warm blooded, vertebrate animals, including, without limitation, humans, non-human primates, rats, mice, cats, dogs, horses, cattle, cows, pigs, sheep and rabbits.

The term "nucleoside" generally refers to compounds consisting of a sugar, usually ribose, deoxyribose, pentose, arabinose or hexose, and a purine or pyrimidine base.

The term "nucleotide" generally refers to a nucleoside comprising a phosphorous-containing group attached to the sugar.

The term "modified nucleoside" or "nucleotide derivative" generally is a nucleoside that includes a modified heterocyclic base, a modified sugar moiety, or any combination thereof. In some embodiments, the modified nucleoside or nucleotide derivative is a non-natural pyrimidine or purine nucleoside, as herein described. For purposes of the invention, a modified nucleoside or nucleotide derivative, a pyrimidine or purine analog or non-naturally occurring pyrimidine or purine can be used interchangeably and refers to a nucleoside that includes a non-naturally occurring base and/or non-naturally occurring sugar moiety. For purposes of the invention, a base is considered to be non-natural if it is not guanine, cytosine, adenine, thymine or uracil and a sugar is considered to be non-natural if it is not β-ribofuranoside or 2'-deoxyribo-furanoside.

The term "modified oligonucleotide" as used herein describes an oligonucleotide in which at least two of its nucleotides are covalently linked via a synthetic linkage, i.e., a linkage other than a phosphodiester linkage between the 5' end of one nucleotide and the 3' end of another nucleotide in which the 5' nucleotide phosphate has been replaced with any number of chemical groups. The term "modified oligonucleotide" also encompasses 2'-O,4'-C-methylene-b-D-ribofuranosyl nucleic acids, arabinose nucleic acids, substituted arabinose nucleic acids, hexose nucleic acids, peptide nucleic acids, morpholino, and oligonucleotides having at least one nucleotide with a modified base and/or sugar, such as a 2'-O-substituted, a 5-methylcytosine and/or a 3'-O-substituted ribonucleotide.

The term "nucleic acid" encompasses a genomic region or an RNA molecule transcribed therefrom. In some embodiments, the nucleic acid is mRNA.

The term "linker" generally refers to any moiety that can be attached to an oligonucleotide by way of covalent or non-covalent bonding through a sugar, a base, or the backbone. The non-covalent linkage may be, without limitation, electrostatic interactions, hydrophobic interactions, π-stacking interactions, hydrogen bonding and combinations thereof. Non-limiting examples of such non-covalent linkage includes Watson-Crick base pairing, Hoogsteen base pairing, and base stacking. The linker can be used to attach two or more nucleosides or can be attached to the 5' and/or 3' terminal nucleotide in the oligonucleotide. Such linker can be either a non-nucleotide linker or a nucleoside linker.

The term "non-nucleotide linker" generally refers to a chemical moiety, other than a linkage directly between two nucleotides that can be attached to an oligonucleotide by way of covalent or non-covalent bonding. Preferably such non-nucleotide linker is from about 2 angstroms to about 200 angstroms in length, and may be either in a cis or trans orientation.

The term "internucleotide linkage" generally refer to a chemical linkage to join two nucleosides through their sugars (e.g. 3'–3', 2'–3', 2'–5', 3'–5', 5'–5') consisting of a phosphorous atom and a charged, or neutral group (e.g., phosphodiester, phosphorothioate, phosphorodithioate or methylphosphonate) between adjacent nucleosides.

The term "oligonucleotide" refers to a polynucleoside formed from a plurality of linked nucleoside units, which may include, for example, deoxyribonucleotides or ribonucleotides, synthetic or natural nucleotides, phosphodiester or modified linkages, natural bases or modified bases natural sugars or modified sugars, or combinations of these components. The nucleoside units may be part of viruses, bacteria, cell debris or oligonucleotide-based compositions (for example, siRNA and microRNA). Such oligonucleotides can also be obtained from existing nucleic acid sources, including genomic or cDNA, but are preferably produced by synthetic methods. In certain embodiments each nucleoside unit includes a heterocyclic base and a pentofuranosyl, trehalose, arabinose, 2'-deoxy-2'-substituted nucleoside, 2'-deoxy-2'-substituted arabinose, 2'-O-substitutedarabinose or hexose sugar group. The nucleoside residues can be coupled to each other by any of the numerous known internucleoside linkages. Such internucleoside linkages include, without limitation, phosphodiester, phosphorothioate, phosphorodithioate, methylphosphonate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., ($R_P$)- or ($S_P$)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain exemplary embodiments, these internucleoside linkages may be phosphodiester, phosphorothioate or phosphorodithioate linkages, or combinations thereof. In exemplary embodiments, the nucleotides of the synthetic oligonucleotides are linked by at least one phosphorothioate internucleotide linkage. The phosphorothioate linkages may be mixed Rp and Sp enantiomers, or they may be stereoregular or substantially stereoregular in either Rp or Sp form (see Iyer et al. (1995) Tetrahedron Asymmetry 6:1051-1054). In certain embodiments, one or more of the oligonucleotides within the antisense compositions of the invention contain one or more 2'-O,4'-C-methylene-b-D-ribofuranosyl nucleic acids, wherein the ribose is modified with a bond between the 2' and 4' carbons, which fixes the ribose in the 3'-endo structural conformation.

"OX40 nucleic acid" means any nucleic acid encoding OX40. For example, in certain embodiments, a OX40 nucleic acid includes a DNA sequence encoding OX40, an RNA sequence transcribed from DNA encoding OX40 (including genomic DNA comprising introns and exons), and an mRNA sequence encoding OX40. "OX40 mRNA" means an mRNA encoding an OX40 protein.

"OX40L nucleic acid" means any nucleic acid encoding OX40L. For example, in certain embodiments, a OX40L nucleic acid includes a DNA sequence encoding OX40L, an RNA sequence transcribed from DNA encoding OX40L (including genomic DNA comprising introns and exons), and an mRNA sequence encoding OX40L. "OX40L mRNA" means an mRNA encoding an OX40L protein.

"PD1 nucleic acid" means any nucleic acid encoding PD1. For example, in certain embodiments, a PD1 nucleic acid includes a DNA sequence encoding PD1, an RNA sequence transcribed from DNA encoding PD1 (including genomic DNA comprising introns and exons), and an mRNA sequence encoding PD1. "PD1 mRNA" means an mRNA encoding a PD1 protein.

"PDL1 nucleic acid" means any nucleic acid encoding PDL1. For example, in certain embodiments, a PDL1 nucleic acid includes a DNA sequence encoding PDL1, an RNA sequence transcribed from DNA encoding PDL1 (including genomic DNA comprising introns and exons), and an mRNA sequence encoding PDL1. "PDL1 mRNA" means an mRNA encoding a PDL1 protein.

The term "peptide" generally refers to oligomers or polymers of amino acids that are of sufficient length and composition to affect a biological response, for example, antibody production or cytokine activity whether or not the peptide is a hapten. The term "peptide" may include modified amino acids (whether or not naturally or non-naturally occurring), where such modifications include, but are not limited to, phosphorylation, glycosylation, pegylation, lipidization, and methylation.

The term "pharmaceutically acceptable" means a non-toxic material that does not interfere with the effectiveness of a compound according to the invention or the biological activity of a compound according to the invention.

The term "physiologically acceptable" refers to a non-toxic material that is compatible with a biological system such as a cell, cell culture, tissue, or organism. Preferably, the biological system is a living organism, such as a mammal, particularly a human.

The term "prophylactically effective amount" generally refers to an amount sufficient to prevent or reduce the development of an undesired biological effect.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Single-stranded oligonucleotide" means an oligonucleotide which is not hybridized to a complementary strand.

"Specifically hybridizable" refers to a gene silencing compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Targeting" or "targeted" means the process of design and selection of a gene silencing compound that will specifically hybridize to a target nucleic acid and induce a desired effect.

"Target nucleic acid," "target RNA," "target mRNA," and "target RNA transcript" all refer to a nucleic acid capable of being targeted by gene silencing compounds.

"Target segment" means the sequence of nucleotides of a target nucleic acid to which a gene silencing compound is targeted. "5' target site" refers to the 5'-most nucleotide of a target segment. "3' target site" refers to the 3'-most nucleotide of a target segment.

The term "therapeutically effective amount" or "pharmaceutically effective amount" generally refers to an amount sufficient to affect a desired biological effect, such as a beneficial result, including, without limitation, prevention, diminution, amelioration or elimination of signs or symptoms of a disease or disorder. Thus, the total amount of each active component of the pharmaceutical composition or method is sufficient to show a meaningful patient benefit, for example, but not limited to, healing of chronic conditions characterized by immune stimulation. Thus, a "pharmaceutically effective amount" will depend upon the context in which it is being administered. A pharmaceutically effective amount may be administered in one or more prophylactic or therapeutic administrations. When applied to an individual active ingredient, administered alone, the term refers to that ingredient alone. When applied to a combination, the term refers to combined amounts of the active ingredients that result in the therapeutic effect, whether administered in combination, serially or simultaneously.

"TIM3 nucleic acid" means any nucleic acid encoding TIM3. For example, in certain embodiments, a TIM3 nucleic acid includes a DNA sequence encoding TIM3, an RNA sequence transcribed from DNA encoding TIM3 (including genomic DNA comprising introns and exons), and an mRNA sequence encoding TIM3. "TIM3 mRNA" means an mRNA encoding a TIM3 protein.

The term "treatment" generally refers to an approach intended to obtain a beneficial or desired result, which may include alleviation of symptoms, or delaying or ameliorating a disease progression.

The term "gene expression" generally refers to process by which information from a gene is used in the synthesis of a functional gene product, which may be a protein. The process may involve transcription, RNA splicing, translation, and post-translational modification of a protein, and may include mRNA, preRNA, ribosomal RNA, and other templates for protein synthesis.

In certain embodiments provided are methods, compounds, and compositions for inhibiting PD1, PDL1, IDO1, LAG3, TIM3, CTLA4, IDO2, CEACAM1, OX40, or OX40L mRNA or protein expression. In certain embodiments the compounds are antisense oligonucleotides, double stranded or single-stranded siRNA compounds, or gene silencing compounds.

As used herein, gene silencing compounds according to the invention comprise two or more single-stranded antisense oligonucleotides linked at their 5' ends, wherein the compounds have two or more accessible 3' ends. The general structure of the oligonucleotide-based compounds of the invention may be described by the following formula I:

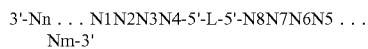
(Formula I), wherein L is a nucleotide linker or non-nucleotide linker; N1-N8, at each occurrence, is independently a nucleotide or nucleotide derivative; Nm and Nn, at each occurrence, are independently a nucleotide or nucleotide derivative; and wherein m and n are independently numbers from 0 to about 40.

The linkage at the 5' ends of the component oligonucleotides is independent of the other oligonucleotide linkages and may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

In certain embodiments provided are gene silencing compounds targeted to a mouse or human PD1 nucleic acid. In certain embodiments, the mouse PD1 nucleic acid is the sequence set forth in GENBANK Accession No. NM_008798 (incorporated herein as SEQ ID NO: 387) or the human PD1 nucleic acid is the sequence set forth in GENBANK Accession No. NM_005018 (incorporated herein as SEQ ID NO: 388).

In certain embodiments provided are gene silencing compounds targeted to a mouse or human PDL1 nucleic acid. In certain embodiments, the mouse PDL1 nucleic acid is the sequence set forth in GENBANK Accession No. NM_021893 (incorporated herein as SEQ ID NO: 389) or the human PDL1 nucleic acid is the sequence set forth in GENBANK Accession No. NM_014143 (incorporated herein as SEQ ID NO: 390).

In certain embodiments provided are gene silencing compounds targeted to a mouse or human IDO1 nucleic acid. In certain embodiments, the mouse IDO1 nucleic acid is the sequence set forth in GENBANK Accession No. NM_008324 (incorporated herein as SEQ ID NO: 391) or the human IDO1 nucleic acid is the sequence set forth in GENBANK Accession No. NM_002164 (incorporated herein as SEQ ID NO: 392).

In certain embodiments provided are gene silencing compounds targeted to a mouse or human LAG3 nucleic acid. In certain embodiments, the mouse LAG3 nucleic acid is the sequence set forth in GENBANK Accession No. NM_008479 (incorporated herein as SEQ ID NO: 393) or the human LAG3 nucleic acid is the sequence set forth in GENBANK Accession No. NM_002286 (incorporated herein as SEQ ID NO: 394).

In certain embodiments provided are gene silencing compounds targeted to a mouse or human TIM3 nucleic acid. In certain embodiments, the mouse TIM3 nucleic acid is the sequence set forth in GENBANK Accession No. NM_134250 (incorporated herein as SEQ ID NO: 395) or the human TIM3 nucleic acid is the sequence set forth in GENBANK Accession No. NM_032782 (incorporated herein as SEQ ID NO: 396).

In certain embodiments provided are gene silencing compounds targeted to a mouse or human CTLA4 nucleic acid. In certain embodiments, the mouse CTLA4 nucleic acid is the sequence set forth in GENBANK Accession No. NM_009843 (incorporated herein as SEQ ID NO: 397) or the human CTLA4 nucleic acid is the sequence set forth in GENBANK Accession No. NM_005214 (incorporated herein as SEQ ID NO: 398).

In certain embodiments provided are gene silencing compounds targeted to a mouse or human IDO2 nucleic acid. In certain embodiments, the mouse IDO2 nucleic acid is the sequence set forth in GENBANK Accession No. NM_145949 (incorporated herein as SEQ ID NO: 399) or the human IDO2 nucleic acid is the sequence set forth in GENBANK Accession No. NM_194294 (incorporated herein as SEQ ID NO: 400).

In certain embodiments provided are gene silencing compounds targeted to a mouse or human CEACAM1 nucleic acid. In certain embodiments, the mouse CEACAM1 nucleic acid is the sequence set forth in GENBANK Accession No. NM_001039187 (incorporated herein as SEQ ID NO: 401) or the human CEACAM1 nucleic acid is the sequence set forth in GENBANK Accession No. NM_001205344 (incorporated herein as SEQ ID NO: 402).

In certain embodiments provided are gene silencing compounds targeted to a mouse or human OX40 nucleic acid. In certain embodiments, the mouse OX40 nucleic acid is the sequence set forth in GENBANK Accession No. NM_011659 (incorporated herein as SEQ ID NO: 403) or the human OX40 nucleic acid is the sequence set forth in GENBANK Accession No. NM_003327 (incorporated herein as SEQ ID NO: 404).

In certain embodiments provided are gene silencing compounds targeted to a mouse or human OX40L nucleic acid. In certain embodiments, the mouse OX40L nucleic acid is the sequence set forth in GENBANK Accession No. NM_009452 (incorporated herein as SEQ ID NO: 405) or the human OX40L nucleic acid is the sequence set forth in GENBANK Accession No. NM_003326 (incorporated herein as SEQ ID NO: 406).

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, or SEQ ID NO: 406. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, or SEQ ID NO: 406. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, or SEQ ID NO: 406. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, or SEQ ID NO: 406.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 387, SEQ ID NO: 389, SEQ ID NO: 391, SEQ ID NO: 393, SEQ ID NO: 395, SEQ ID NO: 397, SEQ ID NO: 399, SEQ ID NO: 401, SEQ ID NO: 403, or SEQ ID NO: 405. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 387, SEQ ID NO: 389, SEQ ID NO: 391, SEQ ID NO: 393, SEQ ID NO: 395, SEQ ID NO: 397, SEQ ID NO: 399, SEQ ID NO: 401, SEQ ID NO: 403, or SEQ ID NO: 405. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 387, SEQ ID NO: 389, SEQ ID NO: 391, SEQ ID NO: 393, SEQ ID NO: 395, SEQ ID NO: 397, SEQ ID NO: 399, SEQ ID NO: 401, SEQ ID NO: 403, or SEQ ID NO: 405. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 387, SEQ ID NO: 389, SEQ ID NO: 391, SEQ ID NO: 393, SEQ ID NO: 395, SEQ ID NO: 397, SEQ ID NO: 399, SEQ ID NO: 401, SEQ ID NO: 403, or SEQ ID NO: 405.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 388, SEQ ID NO: 390, SEQ ID NO: 392, SEQ ID NO: 394, SEQ ID NO: 396, SEQ ID NO: 398, SEQ ID NO: 400, SEQ ID NO: 402, SEQ ID NO: 404, or SEQ ID NO: 406. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 388, SEQ ID NO: 390, SEQ ID NO: 392, SEQ ID NO: 394, SEQ ID NO: 396, SEQ ID NO: 398, SEQ ID NO: 400, SEQ ID NO: 402, SEQ ID NO: 404, or SEQ ID NO: 406. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 388, SEQ ID NO: 390, SEQ ID NO: 392, SEQ ID NO: 394, SEQ ID NO: 396, SEQ ID NO: 398, SEQ ID NO: 400, SEQ ID NO: 402, SEQ ID NO: 404, or SEQ ID NO: 406. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 388, SEQ ID NO: 390, SEQ ID NO: 392, SEQ ID NO: 394, SEQ ID NO: 396, SEQ ID NO: 398, SEQ ID NO: 400, SEQ ID NO: 402, SEQ ID NO: 404, or SEQ ID NO: 406.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 387. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 387. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 387. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 387.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 388. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 388. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 388. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 388.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 389. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 389. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 389. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 389.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 390. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 390. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 390. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 390.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 391. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 391. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 391. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 391.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 392. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 392. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 392. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 392.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 393. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 393. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 393. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 393.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 394. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 394. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 394. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 394.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 395. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 395. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 395. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 395.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 396. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 396. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 396. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 396.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 397. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 397. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 397. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 397.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 398. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 398. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 398. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 398.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 399. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 399. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 399. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 399.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 400. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 400. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 400. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 400.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 401. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 401. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 401. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 401.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 402. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 402. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 402. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 402.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 403. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 403. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 403. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 403.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 404. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 404. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 404. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 404.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 405. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 405. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 405. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 405.

Certain embodiments provide gene silencing compounds comprising two oligonucleotides each, independently, consisting of 12 to 30 nucleotides having a nucleobase sequence comprising a portion of at least 12 contiguous nucleobases complementary to an equal length portion of SEQ ID NO: 406. Certain embodiments provide compounds comprising two oligonucleotides each, independently, consisting of 15 to 25 nucleotides having a nucleobase sequence comprising a portion of at least 12 contiguous nucleobases complementary to an equal length portion of SEQ ID NO: 406. Certain embodiments provide compounds comprising a modified oligonucleotide consisting of 18 to 21 nucleotides having a nucleobase sequence comprising a portion of at least 12 contiguous nucleobases complementary to an equal length portion of SEQ ID NO: 406. In certain embodiments, the two oligonucleotide of the gene silencing compound each, independently, comprise at least 9, at least 10, at least 11, at least 12, at least 13, at least 14, at least 15, at least 16, at least 17, at least 18, at least 19, at least 20, or at least 21 contiguous nucleobases complementary to an equal length portion of SEQ ID NO: 406.

In certain embodiments, the nucleobase sequence of the oligonucleotides of the gene silencing compound are, independently, at least 90% complementary over its entire length to a nucleobase sequence of SEQ ID NO: 387, 388, 389, 390, 391, 392, 393, 394, 395, 396, 397, 398, 399, 400, 401, 402, 403, 404, 405, or 406. In certain embodiments, the nucleobase sequence of the oligonucleotides of the gene silencing compound are, independently, at least 95% complementary over its entire length to a nucleobase sequence of SEQ ID NO: 387, 388, 389, 390, 391, 392, 393, 394, 395, 396, 397, 398, 399, 400, 401, 402, 403, 404, 405, or 406. In certain embodiments, the oligonucleotides of the gene silencing compound are at least 99% complementary over its entire length to SEQ ID NO: 387, 388, 389, 390, 391, 392, 393, 394, 395, 396, 397, 398, 399, 400, 401, 402, 403, 404, 405, or 406. In certain embodiments, the nucleobase sequence of the oligonucleotides of the gene silencing compound are 100% complementary over its entire length to a nucleobase sequence of SEQ ID NO: 387, 388, 389, 390, 391, 392, 393, 394, 395, 396, 397, 398, 399, 400, 401, 402, 403, 404, 405, or 406.

In certain embodiments, the oligonucleotides of the gene silencing compound are, independently, 12 to 30 nucleotides in length. In other words, the oligonucleotides are from 12 to 30 linked nucleobases. In other embodiments, the oligonucleotides, independently, consist of 15 to 28, 18 to 24, 19 to 22, or 20 linked nucleobases. In certain such embodiments, the oligonucleotides, independently, consist of 8, 9, 10, 11, 12, 13, 14, 15, 16, 17, 18, 19, 20, 21, 22, 23, 24, 25, 26, 27, 28, 29, 30 linked nucleobases in length, or a range defined by any two of the above values.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for PD1, PDL1, IDO1, LAG3, TIM3, CTLA4, IDO2, CEACAM1, OX40, or OX40L can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Certain embodiments provide a composition comprising a 3GA compound as described herein, or a salt thereof, and a pharmaceutically acceptable carrier or diluent. Certain embodiments provide a composition comprising two or more 3GA compounds as described herein, or a salt thereof, and a pharmaceutically acceptable carrier or diluent. The two or more 3GA compounds can inhibit the mRNA or protein expression of the same target or can inhibit the mRNA or protein expression of different targets.

In certain embodiments, the 3GA compounds according to the invention comprise two identical or different sequences linked at their 5'-5' ends via a phosphodiester, phosphorothioate or non-nucleoside linker. 3GA compounds according to the invention that comprise identical sequences are able to bind to a specific mRNA via Watson-Crick hydrogen bonding interactions and inhibit mRNA and protein expression. Gene silencing compounds according to the invention that comprise different sequences are able to bind to two or more different regions of one or more mRNA target and inhibit mRNA and protein expression. Such compounds are comprised of heteronucleotide sequences complementary to target mRNA and form stable duplex structures through Watson-Crick hydrogen bonding.

In certain embodiments, gene silencing compounds according to the invention are useful in treating and/or preventing diseases wherein inhibiting PD1, PDL1, IDO1, LAG3, TIM3, CTLA4, IDO2, CEACAM1, OX40, or OX40L expression would be beneficial. Gene silencing compounds according to the invention include, but are not limited to, antisense oligonucleotides comprising naturally occurring nucleotides, modified nucleotides, modified oligonucleotides and/or backbone modified oligonucleotides.

The oligonucleotides of the 3GA compounds are linked through their 5'-ends to allow the presence of two or more accessible 3'-ends. In certain embodiments, the oligonucleotides are linked through one or more of the non-nucleotide linkers listed in Table 1. In certain embodiments, a single linker listed in Table 1 is used to link the oligonucleotides of the gene silencing compounds. In certain embodiments, the linker is small molecule linker such as glycerol or a glycerol homolog of the formula HO—$(CH_2)_o$—CH(OH)—$(CH_2)_p$—OH, wherein o and p independently are integers from 1 to about 6, from 1 to about 4 or from 1 to about 3. In some other embodiments, the small molecule linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6 or from 2 to about 4. Representative non-nucleotide linkers are set forth in Table 1.

TABLE 1

Representative Non-Nucleotide Linkers

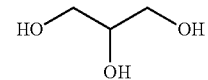

Glycerol(1,2,3-Propanetriol)

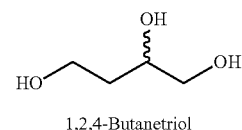

1,2,4-Butanetriol

TABLE 1-continued

Representative Non-Nucleotide Linkers

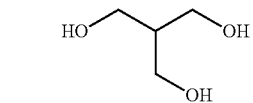

2-(hydroxymethyl)-1,3-propanediol

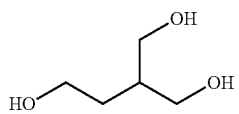

2-(hydroxymethyl)1,4-butanediol

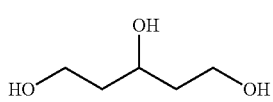

1,3,5-Pentanetriol

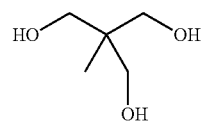

1,1,1-Tris(hydroxymethyl)ethane

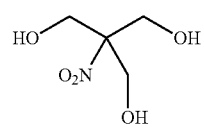

1,1,1-Tris(hydroxymethyl)nitromethane

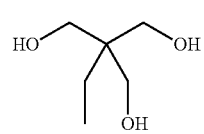

1,1,1-Tris(hydroxymethyl)propane

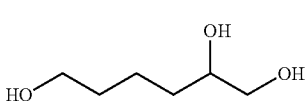

1,2,6-Hexanetriol

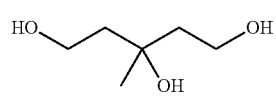

3-Methyl-1,3,5-pentanetriol

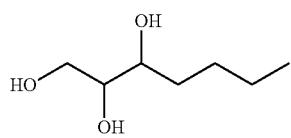

1,2,3-Heptanetriol

TABLE 1-continued

Representative Non-Nucleotide Linkers

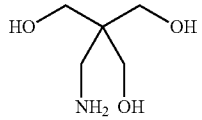

2-Amino-2-(hydroxymethyl)-1,3-propanediol

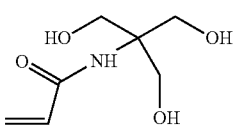

N-[Tris(hydroxymethyl)methyl]acrylamide

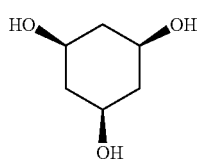

cis-1,3,5-Cyclohexanetriol

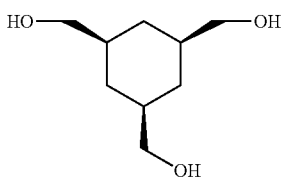 [SMILES: OC[C@H]1C[C@@H](CO)C[C@@H](CO)C1]

cis-1,3,5-Tri(hydroxymethyl)cyclohexane

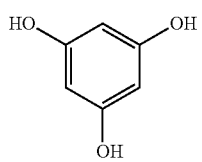

1,3,5,-Trihydroxyl-benzene

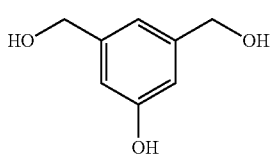 [SMILES: OCc1cc(O)cc(CO)c1]

3,5,-Di(hydroxymethyl)phenol

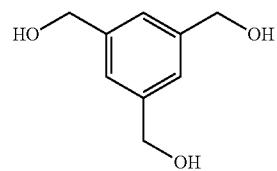 [SMILES: OCc1cc(CO)cc(CO)c1]

1,3,5-Tri(hydroxymethyl)benzene

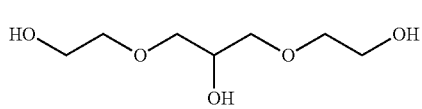 [SMILES: OCCOCC(O)COCCO]

1,3-Di(hydroxyethoxy)-2-hydroxyl-propane

TABLE 1-continued

Representative Non-Nucleotide Linkers

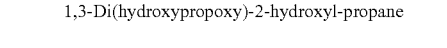

1,3-Di(hydroxypropoxy)-2-hydroxyl-propane

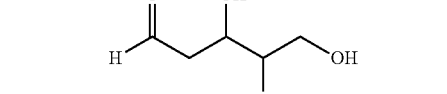

2-Deoxy-D-ribose

1,2,4,-Trihydroxyl-benzene

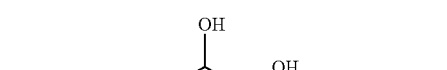

D-Galactoal

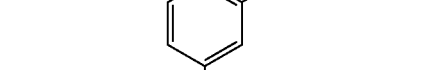

1,6-anhydro-β-D-Glucose

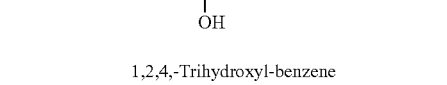

1,3,5-Tris(2-hydroxyethyl)-Cyanuric acid

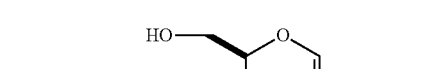

Gallic acid

TABLE 1-continued

Representative Non-Nucleotide Linkers 3,5,7-Trihydroxyflavone 4,6-Nitropyrogallol Ethylene glycol 1,3-Propanediol 1,2-Propanediol 1,4-Butanediol 1,3-Butanediol 2,3-Butanediol 1,4-Butanediol 1,5-Pentanediol 2,4-Pentanediol TABLE 1-continued Representative Non-Nucleotide Linkers

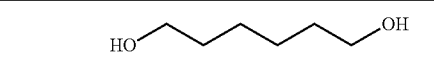

1,6-Hexanediol

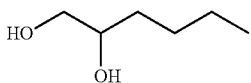

1,2-Hexanediol

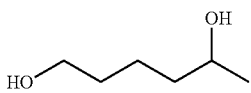

1,5-Hexanediol

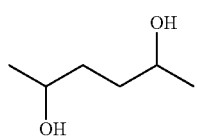

2,5-Hexanediol

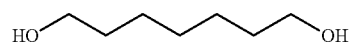

1,7-Heptanediol

1,8-Octanediol

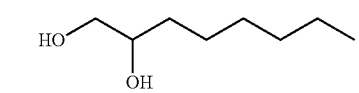

1,2-Octanediol

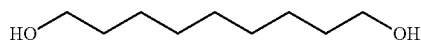 [SMILES: OCCCCCCCCCO]

1,9-Nonanediol

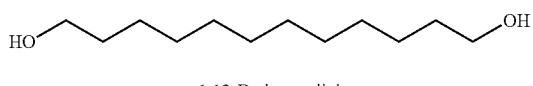

1,12-Dodecanediol

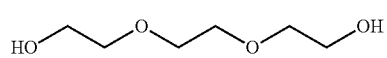

Triethylene glycol

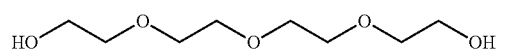 [SMILES: OCCOCCOCCOCCO]

Tetraethylene glycol

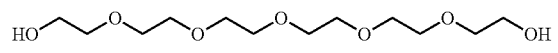

Hexaethylene glycol

TABLE 1-continued

Representative Non-Nucleotide Linkers

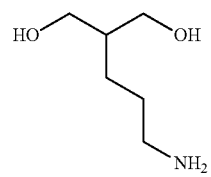

2-(1-Aminopropyl)-1,3-propanediol

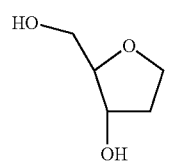

1,2-Dideoxyribose

In some embodiments, the small molecule linker is glycerol or a glycerol homolog of the formula HO—$(CH_2)_o$—CH(OH)—$(CH_2)_p$—OH, wherein o and p independently are integers from 1 to about 6, from 1 to about 4 or from 1 to about 3. In some other embodiments, the small molecule linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6 or from 2 to about 4.

In certain embodiments, the two or more oligonucleotides of the gene silencing compounds of the invention can be linked as shown in Table 2.

TABLE 2

Oligoribonucleotide Formulas II-V

Formula II 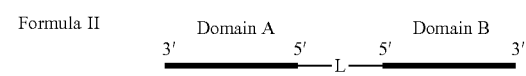

Formula III 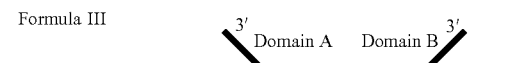

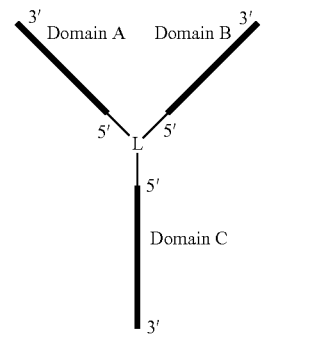

TABLE 2-continued

Oligoribonucleotide Formulas II-V

Formula IV

```
         3'            3'
          \Domain A  Domain B/
           \          /
            5'\      /5'
               \ L  /
                |
                |3'
                |
                | Domain C
                |
                |5'
```

Formula V

```
              5'  Domain A  3'
              5'  Domain B  3'
         L —  5'  Domain C  3'
              5'  Domain D  3'
```

In certain embodiments of Formulas II and/or V, L is a linker or a nucleotide linkage and Domain A and/or Domain B are antisense oligonucleotides that are designed to selectively hybridize to the same target RNA sequence or different target RNA sequences.

In certain embodiments of Formulas II, III, IV or V, L is a linker and Domain A and/or Domain B and/or Domain C and/or Domain D are antisense oligonucleotides that are designed to selectively hybridize to the same target RNA sequence or different target RNA sequences. For example, in one embodiment, Domain A and/or Domain B and/or Domain C of Formulas II and/or III are antisense oligonucleotides that are designed to selectively hybridize to the same target RNA sequence. In this embodiment, Domain A and/or Domain B and/or Domain C can be designed to hybridize to the same region on the target RNA sequence or to different regions of the same target RNA sequence.

In a further embodiment of this aspect of the invention, Domain A, Domain B, Domain C, and Domain D are independently RNA or DNA-based oligonucleotides. In certain aspects of this embodiment, the oligonucleotides comprise mixed backbone oligonucleotides.

In another embodiment, one or more of Domain A and/or Domain B and/or Domain C and/or Domain D is an antisense oligonucleotide that is designed to selectively hybridize to one target RNA sequence and one or more of the remaining Domain A and/or Domain B and/or Domain C and/or Domain D is an antisense oligonucleotide that is designed to selectively hybridized to a different target RNA sequence.

In another embodiment, one or more of Domain A and/or Domain B and/or Domain C and/or Domain D is an RNA-based oligonucleotide hybridized to a complimentary RNA-based oligonucleotide such that the domain comprises an siRNA molecule.

These gene silencing compounds of the invention can be prepared by the art recognized methods such as phosphoramidate or H-phosphonate chemistry which can be carried out manually or by an automated synthesizer. The synthetic antisense oligonucleotides of the invention may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate or carboxymethyl ester or a combination of these and other internucleotide linkages between the 5' end of one nucleotide and the 3' end of another nucleotide in which the 5' nucleotide phosphodiester linkage has been replaced with any number of chemical groups.

The synthetic antisense oligonucleotides of the invention may comprise combinations of internucleotide linkages. For example, U.S. Pat. No. 5,149,797 describes traditional chimeric oligonucleotides having a phosphorothioate core region interposed between methylphosphonate or phosphoramidate flanking regions. Additionally, U.S. Pat. No. 5,652,356 discloses "inverted" chimeric oligonucleotides comprising one or more nonionic oligonucleotide region (e.g. alkylphosphonate and/or phosphoramidate and/or phosphotriester internucleoside linkage) flanked by one or more region of oligonucleotide phosphorothioate. Various synthetic antisense oligonucleotides with modified internucleotide linkages can be prepared according to standard methods. In certain embodiments, the phosphorothioate linkages may be mixed Rp and Sp enantiomers, or they may be made stereoregular or substantially stereoregular in either Rp or Sp form.

Other modifications of gene silencing compounds of the invention include those that are internal or at the end(s) of the oligonucleotide molecule and include additions to the molecule of the internucleoside phosphate linkages, such as cholesterol, cholesteryl, or diamine compounds with varying numbers of carbon residues between the amino groups and terminal ribose, deoxyribose and phosphate modifications which cleave, or crosslink to the opposite chains or to associated enzymes or other proteins which bind to the genome. Examples of such modified oligonucleotides include oligonucleotides with a modified base and/or sugar such as 2'-O,4'-C-methylene-b-D-ribofuranosyl, or arabinose instead of ribose, or a 3', 5'-substituted oligonucleotide having a sugar which, at both its 3' and 5' positions, is attached to a chemical group other than a hydroxyl group (at its 3' position) and other than a phosphate group (at its 5' position).

Other examples of modifications to sugars of the oligonucleotide-based compounds of the invention include modifications to the 2' position of the ribose moiety which include but are not limited to 2'-O-substituted with an —O-alkyl group containing 1-6 saturated or unsaturated carbon atoms, or with an —O-aryl, or —O-allyl group having 2-6 carbon atoms wherein such —O-alkyl, —O-aryl or —O-allyl group may be unsubstituted or may be substituted, for example with halo, hydroxyl, trifluoromethyl, cyano, nitro, acyl, acyloxy, alkoxy, carboxy, carbalkoxyl or amino groups. None of these substitutions are intended to exclude the presence of other residues having native 2'-hydroxyl group in the case of ribose or 2' H— in the case of deoxyribose.

The gene silencing compounds according to the invention can comprise one or more ribonucleotides. For example, U.S. Pat. No. 5,652,355 discloses traditional hybrid oligonucleotides having regions of 2'-O-substituted ribonucleotides flanking a DNA core region. U.S. Pat. No. 5,652,356 discloses an "inverted" hybrid oligonucleotide that includes an oligonucleotide comprising a 2'-O-substituted (or 2' OH, unsubstituted) RNA region which is in between two oligodeoxyribonucleotide regions, a structure that "inverted relative to the "traditional" hybrid oligonucleotides. Non-limiting examples of particularly useful oligonucleotides of the invention have 2'-O-alkylated ribonucleotides at their 3', 5', or 3' and 5' termini, with at least four, and in some exemplary embodiments five, contiguous nucleotides being so modified. Non-limiting examples of 2'-O-alkylated groups include 2'-O-methyl, 2'-O-ethyl, 2'-O-propyl, 2'-O-butyls and 2'-O-methoxy-ethyl.

The oligonucleotide-based compounds of the invention may conveniently be synthesized using an automated synthesizer and phosphoramidite approach further described in Example 1. In some embodiments, the oligonucleotide-based compounds of the invention are synthesized by a linear synthesis approach.

An alternative mode of synthesis is "parallel synthesis", in which synthesis proceeds outward from a central linker moiety. A solid support attached linker can be used for parallel synthesis, as is described in U.S. Pat. No. 5,912,332. Alternatively, a universal solid support (such as phosphate attached controlled pore glass) support can be used.

Parallel synthesis of the oligonucleotide-based compounds of the invention has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the final immune modulatory oligoribonucleotide product.

At the end of the synthesis by either linear synthesis or parallel synthesis protocols, the oligonucleotide-based compounds of the invention may conveniently be deprotected with concentrated ammonia solution or as recommended by the phosphoramidite supplier, if a modified nucleoside is incorporated. The product oligonucleotide-based compounds is preferably purified by reversed phase HPLC, detritylated, desalted and dialyzed.

In certain embodiments, the oligonucleotides of the gene silencing compound according to the invention are selected from the non-limiting list of the oligonucleotides shown in Table 3 below. The oligonucleotides shown in Table 3 have phosphorothioate (PS) linkages, but may also include phosphodiester linkages. Those skilled in the art will recognize, however, that other linkages, based on phosphodiester or non-phosphodiester moieties may be included.

TABLE 3

| Oligo #/SEQ ID NO: | Target | Species | Target Site | Sequence 5'→3' |
|---|---|---|---|---|
| 1 | PD1 | Mouse | 58 | GCCGGACCCACATGCCCAG |
| 2 | PD1 | Mouse | 65 | GGTACCTGCCGGACCCACA |
| 3 | PD1 | Mouse | 115 | GCCACCCTGATTGCCAGCT |
| 4 | PD1 | Mouse | 198 | GGTGGCATTTGCTCCCTCT |
| 5 | PD1 | Mouse | 755 | GGTGTCTTCTCTCGTCCCT |
| 6 | PD1 | Mouse | 848 | GCTGAGCCCCTACGTCCCA |
| 7 | PD1 | Mouse | 1161 | CCCCAGCTCTGCACCTTGT |
| 8 | PD1 | Mouse | 1589 | CTAGCTCTGCTGGTTCCCT |
| 9 | PD1 | Human | 69 | GCGCCTGTGGGATCTGCAT |
| 10 | PD1 | Human | 108 | GCCAGCCCAGTTGTAGCAC |
| 11 | PD1 | Human | 285 | GCTTGTCCGTCTGGTTGCT |
| 12 | PD1 | Human | 495 | CCCTTCTCTCTGTCACCCT |
| 13 | PD1 | Human | 496 | GCCCTTCTCTCTGTCACCC |
| 14 | PD1 | Human | 497 | TGCCCTTCTCTCTGTCACC |
| 15 | PD1 | Human | 616 | GCCAGGACCCAGACTAGCA |
| 16 | PD1 | Human | 620 | GACGGCCAGGACCCAGACT |
| 17 | PD1 | Human | 895 | CCATCCTCAGGCCTCAGTG |
| 18 | PD1 | Human | 897 | GTCCATCCTCAGGCCTCAG |
| 19 | PD1 | Human | 899 | GTGTCCATCCTCAGGCCTC |
| 20 | PD1 | Human | 901 | CAGTGTCCATCCTCAGGCC |
| 21 | PD1 | Human | 1003 | GCACCCTGCCTGCTTCTCC |
| 22 | PD1 | Human | 1005 | CTGCACCCTGCCTGCTTCT |
| 23 | PD1 | Human | 1137 | GTGACACCTGCTGCCTGGG |

TABLE 3-continued

| Oligo #/SEQ ID NO: | Target | Species | Target Site | Sequence 5'→3' |
|---|---|---|---|---|
| 24 | PD1 | Human | 1161 | ATCTGGCCCTCCCTGTAGG |
| 25 | PD1 | Human | 1163 | GCATCTGGCCCTCCCTGTA |
| 26 | PD1 | Human | 1165 | CTGCATCTGGCCCTCCCTG |
| 27 | PD1 | Human | 1167 | GACTGCATCTGGCCCTCCC |
| 28 | PD1 | Human | 1169 | GTGACTGCATCTGGCCCTC |
| 29 | PD1 | Human | 1412 | CTCCTGTGCCCAGTCTTGG |
| 30 | PD1 | Human | 1512 | CCCACCACAGCCAGGAGCT |
| 31 | PD1 | Human | 1513 | GCCCACCACAGCCAGGAGC |
| 32 | PD1 | Human | 1563 | GCCTGAGGTGCTGCCTGGG |
| 33 | PD1 | Human | 1591 | CTGCCTCAGCTTCCCTGCC |
| 34 | PD1 | Human | 1592 | ACTGCCTCAGCTTCCCTGC |
| 35 | PD1 | Human | 1615 | CCTCCAGCTCTGCCTGCCC |
| 36 | PD1 | Human | 1616 | GCCTCCAGCTCTGCCTGCC |
| 37 | PD1 | Human | 1720 | GCCCTCCTGACCTTGGGAC |
| 38 | PD1 | Human | 1722 | CTGCCCTCCTGACCTTGGG |
| 39 | PD1 | Human | 1724 | CCCTGCCCTCCTGACCTTG |
| 40 | PD1 | Human | 1894 | CCTTCCCACCCAGGCCCTG |
| 41 | PD1 | Human | 1896 | TACCTTCCCACCCAGGCCC |
| 42 | PD1 | Human | 1898 | TGTACCTTCCCACCCAGGC |
| 43 | PD1 | Human | 1900 | CCTGTACCTTCCCACCCAG |
| 44 | PD1 | Human | 1996 | CTGGATGCTGGTGGCCCTG |
| 45 | PD1 | Human | 1997 | CCTGGATGCTGGTGGCCCT |
| 46 | PD1 | Human | 2024 | CCCAGCCACTCAGGTGCCT |
| 47 | PD1 | Human | 2032 | TCCCTTGTCCCAGCCACTC |
| 48 | PD1 | Human | 2034 | GATCCCTTGTCCCAGCCAC |
| 49 | PDL1 | Mouse | 219 | CAAGCAGGTCCAGCTCCCG |
| 50 | PDL1 | Mouse | 316 | CTCCCCCTGAAGTTGCTGT |
| 51 | PDL1 | Mouse | 436 | TTGTAGTCCGCACCACCGT |
| 52 | PDL1 | Mouse | 1399 | GGTGACCTCTGTGTTCCCT |
| 53 | PDL1 | Mouse | 2152 | GCCTGCCTCTGCCTCCCTA |
| 54 | PDL1 | Mouse | 3311 | GCCCAGCCTGTTCCTTCAG |
| 55 | PDL1 | Human | 571 | GGTAGCCCTCAGCCTGACA |
| 56 | PDL1 | Human | 892 | CCATCATTCTCCCTTTTCT |
| 57 | PDL1 | Human | 1075 | ATTGCCTGCATCCCACGGG |
| 58 | PDL1 | Human | 1080 | CCCACATTGCCTGCATCCC |
| 59 | PDL1 | Human | 1103 | TTCAGTGCTTGGGCCTTTT |
| 60 | PDL1 | Human | 1163 | GGCTCCCTGTTTGACTCCA |
| 61 | PDL1 | Human | 1182 | GTATCAAGGTCTCCCTCCA |

TABLE 3-continued

| Oligo #/SEQ ID NO: | Target | Species | Target Site | Sequence 5'→3' |
|---|---|---|---|---|
| 62 | PDL1 | Human | 1230 | TCCTTTCTCCCTGTCACAG |
| 63 | PDL1 | Human | 1296 | ATTCTCAACCCGTCTTCCT |
| 64 | PDL1 | Human | 1855 | TCTGTTTGCTTCCTCAGCT |
| 65 | PDL1 | Human | 1904 | GGGTGGCAGTCTGAGGTCT |
| 66 | PDL1 | Human | 1911 | GGACAGTGGGTGGCAGTCT |
| 67 | PDL1 | Human | 2142 | TTCCCCTCGCATCATCCTT |
| 68 | PDL1 | Human | 2192 | TCCCAGACCACATTGGCCT |
| 69 | PDL1 | Human | 2901 | TGCACCCTGGAGAGCCCAT |
| 70 | PDL1 | Human | 3128 | GCTGGTGGCATTCAAGGGT |
| 71 | PDL1 | Human | 3173 | CGAAACCTCCAGGAAGCCT |
| 72 | PDL1 | Human | 3196 | GATCTCCCAGGGCATCTGA |
| 73 | PDL1 | Human | 3397 | GCCTTGCTCAGCCACAATT |
| 74 | PDL1 | Human | 3402 | TATGTGCCTTGCTCAGCCA |
| 75 | IDO1 | Mouse | 138 | CTAGCCACAAGGACCCAGG |
| 76 | IDO1 | Mouse | 264 | ATGTACCCAGGGCCAGGT |
| 77 | IDO1 | Mouse | 295 | ATCCCCTCGGTTCCACACA |
| 78 | IDO1 | Mouse | 492 | CCCTTGTCGCAGTCCCCAC |
| 79 | IDO1 | Mouse | 817 | GAAGATGCTGCTCTGGCCT |
| 80 | IDO1 | Mouse | 1145 | CAGTCCCTCTGCTTTCCAC |
| 81 | IDO1 | Human | 172 | GCAGAGCAAAGCCCACTTC |
| 82 | IDO1 | Human | 184 | CCTGTGGATTTGGCAGAGC |
| 83 | IDO1 | Human | 388 | CTCCATGACCTTTGCCCCA |
| 84 | IDO1 | Human | 507 | CTTTTTCTTCCAGTTTGCC |
| 85 | IDO1 | Human | 619 | CAGCTGCTATTTCCACCAA |
| 86 | IDO1 | Human | 816 | GTTGCCTTTCCAGCCAGAC |
| 87 | IDO1 | Human | 823 | GCTGGGGTTGCCTTTCCA |
| 88 | IDO1 | Human | 849 | CCCTTCATACACCAGACCG |
| 89 | IDO1 | Human | 956 | TGTCCTCCACCAGCAGTCT |
| 90 | IDO1 | Human | 1138 | GCAGATGGTAGCTCCTCAG |
| 91 | IDO1 | Human | 1187 | TCCTTTGGCTGCTGGCTTG |
| 92 | IDO1 | Human | 1239 | GCCTCCAGTTCCTTTGGCT |
| 93 | IDO1 | Human | 1246 | AATCAGTGCCTCCAGTTCC |
| 94 | IDO1 | Human | 1327 | GTGCTCTTGTTGGGTTACA |
| 95 | IDO1 | Human | 1627 | GCCTCGGCCTCCCAAAGTG |
| 96 | IDO1 | Human | 1745 | TAGCTGGGACTACAGGTGC |
| 97 | IDO1 | Human | 1767 | TCTCCTGCCTCAGCCTCCC |
| 98 | IDO1 | Human | 1774 | ACGCCATTCTCCTGCCTCA |
| 99 | IDO1 | Human | 1792 | GCTCCGCCTCCCAGGTTCA |

TABLE 3-continued

| Oligo #/SEQ ID NO: | Target | Species | Target Site | Sequence 5'→3' |
|---|---|---|---|---|
| 100 | IDO1 | Human | 1815 | GGCACAATCTTGGCTCACT |
| 101 | LAG3 | Mouse | 25 | GCTCCTCCAGACCCAGTCC |
| 102 | LAG3 | Mouse | 321 | GGCCTCCCCAGCCCTCCAA |
| 103 | LAG3 | Mouse | 355 | GGAGCAGGTCCTCCCTCAT |
| 104 | LAG3 | Mouse | 422 | AGCTCTTTCCCAGGCCCTG |
| 105 | LAG3 | Mouse | 585 | CCCCTGGTGAAGGTCAAGG |
| 106 | LAG3 | Mouse | 590 | GGCATCCCCTGGTGAAGGT |
| 107 | LAG3 | Mouse | 601 | GTCTAGGCGAGGGCATCCC |
| 108 | LAG3 | Mouse | 953 | GGCACTCGGTTCTGGCCCT |
| 109 | LAG3 | Mouse | 1044 | GACACAGCCCCAGGTCCCA |
| 110 | LAG3 | Mouse | 1108 | GCTCCAGACCCAGAACCTT |
| 111 | LAG3 | Mouse | 1161 | GGGCAGCTCCACCCTAGAA |
| 112 | LAG3 | Mouse | 1260 | GCCACTCTTTCCAGCCACG |
| 113 | LAG3 | Mouse | 1295 | GCCAGACCCACAGCCTCAA |
| 114 | LAG3 | Mouse | 1316 | CAGGTGTAGGTCCCAGCCT |
| 115 | LAG3 | Mouse | 1349 | GCATTGAGCTGCTGTCCCT |
| 116 | LAG3 | Mouse | 1524 | GGCCTCCTGAATCTCCAGC |
| 117 | LAG3 | Mouse | 1573 | GCCTCTGGCCCTCGTACAG |
| 118 | LAG3 | Mouse | 1819 | CCAGCTCCTCTATCTTCCT |
| 119 | LAG3 | Mouse | 1918 | CTGCCTCGGCTCCAGGTCA |
| 120 | LAG3 | Mouse | 1936 | GCTGCTGAGACCTGCTGGC |
| 121 | LAG3 | Mouse/Human | 1315 | AGGTGTAGGTCCCAGCCTG |
| 122 | LAG3 | Mouse/Human | 1822 | GCTCCAGCTCCTCTATCTT |
| 123 | LAG3 | Mouse/Human | 1062 | GCCATCTCTGTAGGTGAGG |
| 124 | LAG3 | Mouse/Human | 1356 | GACAGTGGCATTGAGCTGC |
| 125 | LAG3 | Human | 3 | TCTCTGGGCCTTCACCCCT |
| 126 | LAG3 | Human | 123 | CTGGGCAGATCAGGCAGCC |
| 127 | LAG3 | Human | 167 | GGGAGGGATGACCAGAGGC |
| 128 | LAG3 | Human | 229 | GGGAGGTGGAGGAAGGGGT |
| 129 | LAG3 | Human | 346 | CTGAGCCTCCCACATCTCT |
| 130 | LAG3 | Human | 395 | GCTTCACTGGAGCCACCCA |
| 131 | LAG3 | Human | 494 | GGCTGAGATCCTGGAGGGG |
| 132 | LAG3 | Human | 524 | GCTGCCAAGTGACCCCTGC |
| 133 | LAG3 | Human | 648 | GGACCCACGCTCAGCACCG |
| 134 | LAG3 | Human | 736 | CCATAGCGAGAAGTCCCCG |
| 135 | LAG3 | Human | 834 | TGGCCCAGGCGCAGACGGA |
| 136 | LAG3 | Human | 1034 | CCATGGGGCTGACTTGGGG |
| 137 | LAG3 | Human | 1359 | TTGAGCTGCTGTTCCTGCA |

TABLE 3-continued

| Oligo #/SEQ ID NO: | Target | Species | Target Site | Sequence 5'→3' |
|---|---|---|---|---|
| 138 | LAG3 | Human | 1433 | GCAGCTTCCCCAGGGATCC |
| 139 | LAG3 | Human | 1499 | GGGATGGGGTGTCCAGAGA |
| 140 | LAG3 | Human | 1554 | TGGGAAAGGAGCTGGGCCT |
| 141 | LAG3 | Human | 1593 | AGAAGCCTCTCCCCCTGGT |
| 142 | LAG3 | Human | 1636 | GGCACCTGGGCTAGACAGC |
| 143 | LAG3 | Human | 1848 | GGTTCTTGCTCCAGCTCCT |
| 144 | LAG3 | Human | 1940 | GCTGAGATCTGCTGGCTGC |
| 145 | LAG3 | Human/Mouse | 1972 | GCTGCTGACAGGGAGTTTA |
| 146 | LAG3 | Human/Mouse | 642 | ACGCTCAGCACCGTGTAGC |
| 147 | LAG3 | Human/Mouse | 1234 | AGGAGGAGTCCACTTGGCA |
| 148 | LAG3 | Human/Mouse | 1366 | AGTGGCATTGAGCTGCTGT |
| 149 | TIM3 | Mouse | 222 | AATCCCTTGCCCCAGCACA |
| 150 | TIM3 | Mouse | 319 | GAGATCGCCCTTTAGCTGG |
| 151 | TIM3 | Mouse | 386 | TGCAGCAGTAGGTCCCATG |
| 152 | TIM3 | Mouse | 462 | GGAGTGACCTTGGCTGCTT |
| 153 | TIM3 | Mouse | 661 | CCCAGCAGAGACTCCCACT |
| 154 | TIM3 | Mouse | 782 | CATTTGCCAACCCTCCTGG |
| 155 | TIM3 | Mouse | 887 | GCTGGCTGTTGACGTAGCA |
| 156 | TIM3 | Mouse | 1273 | TTAGCCCTTTATTCCCCCT |
| 157 | TIM3 | Mouse | 1416 | CCTCCTGCCTAAGGTTCCC |
| 158 | TIM3 | Mouse | 1425 | ACTTATCACCCTCCTGCCT |
| 159 | TIM3 | Mouse | 1517 | GAGCCTCATCTCCAGCCTC |
| 160 | TIM3 | Mouse | 1526 | TCACTGTCCGAGCCTCATC |
| 161 | TIM3 | Mouse | 1668 | CTGACTGCACGCAAGCCCC |
| 162 | TIM3 | Mouse | 1767 | GAGCAGAGGACAACCCCCA |
| 163 | TIM3 | Mouse | 1953 | CTGCTCTGCCATGCTCCCA |
| 164 | TIM3 | Mouse | 2138 | GTCAGTTCCCCTTGAGCAC |
| 165 | TIM3 | Mouse | 2220 | CTGCCTTCGTATGTCCCAG |
| 166 | TIM3 | Mouse | 2461 | CACAGTTGCTCCCCAATGC |
| 167 | TIM3 | Mouse | 2570 | AGCCAGGACCTCCACAGCT |
| 168 | TIM3 | Mouse | 2596 | GTCTCCCTTCCATACCCAC |
| 169 | TIM3 | Human | 59 | CTGCCAGGTCTACAGTCAC |
| 170 | TIM3 | Human | 281 | CAGCAGCAGCAGCAGGACA |
| 171 | TIM3 | Human | 338 | GGCATTCTGACCGACCTCC |
| 172 | TIM3 | Human | 457 | TCCCTTTCATCAGTCCTGA |
| 173 | TIM3 | Human | 740 | GAGGCTCCCCAGTGTCTGT |
| 174 | TIM3 | Human | 803 | GGCCAATCTAGAGTCCCGT |
| 175 | TIM3 | Human | 1110 | GTGAGGGTTGCTGCCTGCT |

TABLE 3-continued

| Oligo #/SEQ ID NO: | Target | Species | Target Site | Sequence 5'→3' |
|---|---|---|---|---|
| 176 | TIM3 | Human | 1235 | GCAGTGGACAGAACCTCCA |
| 177 | TIM3 | Human | 1304 | CAGTGCAGGTCCCAGTTCA |
| 178 | TIM3 | Human | 1442 | GAGCTCCAGAGACCCCACG |
| 179 | TIM3 | Human | 1456 | GCCCGAATTTCCTGGAGCT |
| 180 | TIM3 | Human | 1506 | CAGCACCCAGTTTTCCCTA |
| 181 | TIM3 | Human | 1549 | GCCCCTTTAGACTTTCTGT |
| 182 | TIM3 | Human | 1640 | TGCCATTGCACTCCAGCCT |
| 183 | TIM3 | Human | 1716 | ATCCCAGCCACTCAGGAGG |
| 184 | TIM3 | Human | 1725 | ATGCCTGTAATCCCAGCCA |
| 185 | TIM3 | Human | 1863 | GCTCACGCCTGTAATCCCA |
| 186 | TIM3 | Human | 1877 | GGCTGGATGTGGTGGCTCA |
| 187 | TIM3 | Human | 2053 | GCCACATCTCAGCCCTGCA |
| 188 | TIM3 | Human | 2246 | GCCTTTGCCTTCTTTCCAC |
| 189 | CTLA4 | Mouse | 106 | GGTCCTCAGGGAGCAGAGT |
| 190 | CTLA4 | Mouse | 191 | AGGCCAAGTCCTAGAAGGC |
| 191 | CTLA4 | Mouse | 253 | TGGGTCACCTGTATGGCTT |
| 192 | CTLA4 | Mouse | 344 | AGTCACCCGGACCTCATCA |
| 193 | CTLA4 | Mouse | 416 | GCCCACTGTATTCTTCTCT |
| 194 | CTLA4 | Mouse | 497 | GTCAACAGCTCTCAGTCCT |
| 195 | CTLA4 | Mouse | 563 | GTTGCCCATGCCCACAAAG |
| 196 | CTLA4 | Mouse | 567 | TCCCGTTGCCCATGCCCAC |
| 197 | CTLA4 | Mouse | 647 | CCCCAAGCTAACTGCGACA |
| 198 | CTLA4 | Mouse | 735 | TCACATAGACCCCTGTTGT |
| 199 | CTLA4 | Mouse | 760 | CATTCTGGCTCTGTTGGGG |
| 200 | CTLA4 | Mouse | 1084 | CCTTGACCCCACACCATAA |
| 201 | CTLA4 | Mouse | 1135 | CTCTTCCTTCACCCCCTTC |
| 202 | CTLA4 | Mouse | 1434 | CTCCCCAGCCAAACCTCCC |
| 203 | CTLA4 | Mouse | 1436 | AGCTCCCCAGCCAAACCTC |
| 204 | CTLA4 | Mouse | 1470 | GACCTCGAGTCCAACCTGA |
| 205 | CTLA4 | Mouse | 1484 | GCCAGTTGGTGCAGGACCT |
| 206 | CTLA4 | Mouse | 1542 | ACTCCATCACCATCGGTTT |
| 207 | CTLA4 | Mouse | 1552 | CCCAGTTTACACTCCATCA |
| 208 | CTLA4 | Mouse | 1794 | TCCCATCCTACCATCTGCT |
| 209 | CTLA4 | Human | 129 | GGGAGCGGTGTTCAGGTCT |
| 210 | CTLA4 | Human | 211 | AGGAGAGTGCAGGGCCAGG |
| 211 | CTLA4 | Human | 346 | CGGACCTCAGTGGCTTTGC |
| 212 | CTLA4 | Human | 504 | CCATGGCCCTCAGTCCTTG |
| 213 | CTLA4 | Human | 574 | CCGTTGCCTATGCCCAGGT |

TABLE 3-continued

| Oligo #/SEQ ID NO: | Target | Species | Target Site | Sequence 5'→3' |
|---|---|---|---|---|
| 214 | CTLA4 | Human | 953 | GGGTTCCGCATCCAACTTT |
| 215 | CTLA4 | Human | 1007 | CATCCCAGCTCTGTCTTTC |
| 216 | CTLA4 | Human | 1067 | GCATCCCCATATTAATCCC |
| 217 | CTLA4 | Human | 1136 | CTCCCTGCCTTTTCCTTCT |
| 218 | CTLA4 | Human | 1308 | ACCTTTAGCATCACTGGCT |
| 219 | CTLA4 | Human | 1514 | AGTGTCCTGAGCTCCTCCA |
| 220 | CTLA4 | Human | 1537 | CCTTGTGTTCTACCTGGTG |
| 221 | CTLA4 | Human | 1570 | CCTCATCCAGTTTCCAAGC |
| 222 | CTLA4 | Human | 1606 | CTCAGCACAATTCCACGCA |
| 223 | CTLA4 | Human | 1632 | AGCCCCAAAGCACATGTCA |
| 224 | CTLA4 | Human | 1747 | ATACCTGTGGGTCTCCTGG |
| 225 | CTLA4 | Human | 1822 | GCCTTCTTCTGTCCATGGC |
| 226 | CTLA4 | Human | 1844 | GCACCCCATTCTGCCACCT |
| 227 | CTLA4 | Human/Mouse | 744 | TCACATAGACCCCTGTTGT |
| 228 | CTLA4 | Human/Mouse | 1117 | TTGGGCTGTGCCATTCCCT |
| 229 | IDO2 | Mouse | 49 | TGCCCCAGAGGAATGCCCA |
| 230 | IDO2 | Mouse | 127 | GTGGTATCTCCCCAAGGAC |
| 231 | IDO2 | Mouse | 279 | CAGTCCAGGAGAGGCATCC |
| 232 | IDO2 | Mouse | 440 | GGAGTCCCAAGTTCCTGGA |
| 233 | IDO2 | Mouse | 510 | TCCAACGGTCCTTCTGGGT |
| 234 | IDO2 | Mouse | 639 | GCCTCCATTCCCTGAACCA |
| 235 | IDO2 | Mouse | 801 | GGATTGTCCTTCCACCCAG |
| 236 | IDO2 | Mouse | 873 | GCTGCACTTCCTCCAGAGT |
| 237 | IDO2 | Mouse | 971 | GCGGCATGTAGTCCCTCAT |
| 238 | IDO2 | Mouse | 1047 | CCAGGACCAGAGGCCAGTA |
| 239 | IDO2 | Mouse | 1215 | GTACCCCAGTGCCCCTGT |
| 240 | IDO2 | Mouse | 1280 | CACCAGGACACAGGAGGGC |
| 241 | IDO2 | Mouse | 1617 | GCTCCCACGGGACCTGACT |
| 242 | IDO2 | Mouse | 1782 | TGAGGAGGTCATGGCTGCA |
| 243 | IDO2 | Mouse | 1911 | GGGACGAGGGAGGTAGGGA |
| 244 | IDO2 | Mouse | 2058 | GTTTGAGGCCCATCAGACC |
| 245 | IDO2 | Mouse | 2345 | GCTCAGTGGCTCATCCCTG |
| 246 | IDO2 | Mouse | 2638 | GGCTGTCCCAGGTCACAGA |
| 247 | IDO2 | Mouse | 2748 | GGTGACTTCCAGGTCTGCA |
| 248 | IDO2 | Mouse | 2756 | CCCGTGCTGGTGACTTCCA |
| 249 | IDO2 | Human | 156 | GGTGTCCATTGCCTTCTGT |
| 250 | IDO2 | Human | 214 | GCCTGGTGGGTGAAGTGTC |
| 251 | IDO2 | Human | 222 | TTGTGGTGGCCTGGTGGGT |

TABLE 3-continued

| Oligo #/SEQ ID NO: | Target | Species | Target Site | Sequence 5'→3' |
|---|---|---|---|---|
| 252 | IDO2 | Human | 284 | ATTCGGTCTGTGGGGCTCC |
| 253 | IDO2 | Human | 561 | CTCCTTCCTGCCAGACATA |
| 254 | IDO2 | Human | 633 | GCCCCAAGTTCCTGGAGAC |
| 255 | IDO2 | Human | 713 | CCCAATTTCCAGGAATCCG |
| 256 | IDO2 | Human | 722 | CTCCAGGTTCCCAATTTCC |
| 257 | IDO2 | Human | 757 | TGCAGGCTCTCTCCCCCAG |
| 258 | IDO2 | Human | 802 | GGCACTGCTTCTTTCTCTA |
| 259 | IDO2 | Human | 1137 | AGTCACCACTTTCCTTGCT |
| 260 | IDO2 | Human | 1207 | GGTGCTGAGTGGATGTCTT |
| 261 | IDO2 | Human | 1253 | CAGCAAGTGGTCCTGTCCA |
| 262 | IDO2 | Human | 1363 | GGCTTCCCATGCTTTGCCT |
| 263 | IDO2 | Human | 1415 | TCCACCTGTGCCCCTGTCT |
| 264 | IDO2 | Human | 1464 | ACTCCAAGGTCTTATCCCT |
| 265 | IDO2 | Human | 1573 | TGATCCCAGGCAGAACCCT |
| 266 | IDO2 | Human | 1593 | GGGCTGAGATCCTTCCTGG |
| 267 | IDO2 | Human | 1745 | TGGGGGTTCTGCATGAGGA |
| 268 | IDO2 | Human | 1752 | ACTCCTCTGGGGGTTCTGC |
| 269 | IDO2 | Human | 1837 | AGTAATGTATCCCCAGGCA |
| 270 | IDO2 | Human | 1945 | AAGAGGGCTGGTCTGGGAC |
| 271 | CEACAM1 | Mouse | 291 | GTAGTGTTTCCCTTGTACC |
| 272 | CEACAM1 | Mouse | 294 | GCCGTAGTGTTTCCCTTGT |
| 273 | CEACAM1 | Mouse | 299 | CTATAGCCGTAGTGTTTCC |
| 274 | CEACAM1 | Mouse | 1110 | GTGAGGAACAGAATCCGGG |
| 275 | CEACAM1 | Mouse | 1526 | TTCCTGCTTCTGGTTTGTT |
| 276 | CEACAM1 | Mouse | 1530 | CCATTTCCTGCTTCTGGTT |
| 277 | CEACAM1 | Mouse | 1531 | GCCATTTCCTGCTTCTGGT |
| 278 | CEACAM1 | Mouse | 2474 | CCATGCTGGAACTCTGTCT |
| 279 | CEACAM1 | Mouse | 2485 | CTGCACAGGCTCCATGCTG |
| 280 | CEACAM1 | Mouse | 2486 | CCTGCACAGGCTCCATGCT |
| 281 | CEACAM1 | Mouse | 2500 | CTGTGGGATTGAAACCTGC |
| 282 | CEACAM1 | Mouse | 2507 | GGTGTTACTGTGGGATTGA |
| 283 | CEACAM1 | Mouse | 2513 | GCAGAAGGTGTTACTGTGG |
| 284 | CEACAM1 | Mouse | 2533 | GTCTGAGCAGGTGGGGTGC |
| 285 | CEACAM1 | Mouse | 2536 | GCAGTCTGAGCAGGTGGGG |
| 286 | CEACAM1 | Mouse | 2568 | TGTCCAGGTAGCCAGGCCT |
| 287 | CEACAM1 | Mouse | 2570 | AATGTCCAGGTAGCCAGGC |
| 288 | CEACAM1 | Human | 103 | GCCCTGTCTTCACCTGTGG |
| 289 | CEACAM1 | Human | 111 | TCCTGCTGGCCCTGTCTTC |

TABLE 3-continued

| Oligo #/SEQ ID NO: | Target | Species | Target Site | Sequence 5'→3' |
|---|---|---|---|---|
| 290 | CEACAM1 | Human | 126 | GTGCCCCATGGTGTCTCCT |
| 291 | CEACAM1 | Human | 1021 | TGGCGTGGCAGGTATAGGA |
| 292 | CEACAM1 | Human | 1403 | GCCCCAGGTGAGAGGCCAT |
| 293 | CEACAM1 | Human | 1440 | AACCAGGGCCACTACTCCA |
| 294 | CEACAM1 | Human | 1463 | GCCAGGGCTACTGCTATCA |
| 295 | CEACAM1 | Human | 1851 | GGTTTCCTACAGACTCCCA |
| 296 | CEACAM1 | Human | 1908 | GTTCTGGTCCCTCTTTCCC |
| 297 | CEACAM1 | Human | 2230 | GGTGCTTAGACCCTGATCC |
| 298 | CEACAM1 | Human | 2396 | CTGCCTTGAACAGAGCCCA |
| 299 | CEACAM1 | Human | 2414 | AACCCCTCCCTCTCAGCAC |
| 300 | CEACAM1 | Human | 2436 | GCTGGTTCCCTCCTGAAGC |
| 301 | CEACAM1 | Human | 2473 | CCTTTCCCAAGTTCCTAGC |
| 302 | CEACAM1 | Human | 2489 | GGGCAGCTCTCTGATTCCT |
| 303 | CEACAM1 | Human | 2700 | GCTCCTGACCAAGGGACCT |
| 304 | CEACAM1 | Human | 2894 | AGCAGAGGCCAAGGTTTCC |
| 305 | CEACAM1 | Human | 2924 | CTCCCACTTCTCAAGGACC |
| 306 | CEACAM1 | Human | 3019 | TCACAGCCCCATTTCCCCA |
| 307 | CEACAM1 | Human | 3323 | GCACAGTCCGTGTCAGGGT |
| 308 | OX40 | Mouse | 20 | GTATGCAGAGTCCCATGAT |
| 309 | OX40 | Mouse | 121 | CCTTGCAGGGTGTGGCTAT |
| 310 | OX40 | Mouse | 161 | CCTTGTCTGCTTTCTGCCT |
| 311 | OX40 | Mouse | 270 | TGTGACCACTGGGGTAGGT |
| 312 | OX40 | Mouse | 495 | GAGGTTGGGTGCCTGGTCT |
| 313 | OX40 | Mouse | 509 | GCCGCTGTCCTGCCGAGGT |
| 314 | OX40 | Mouse | 544 | GGAGGGCAGGGAACACAGT |
| 315 | OX40 | Mouse | 572 | CTGGTTGTTGCCTGGAGAA |
| 316 | OX40 | Mouse | 593 | ATTGGTCCAGGGCTTGCAG |
| 317 | OX40 | Mouse | 642 | CCAAGCTGTCACTGGCTGG |
| 318 | OX40 | Mouse | 693 | GGGTCTCCCAGAGCAGTGT |
| 319 | OX40 | Mouse | 845 | AGTCAAGGGAGCCAGCAGG |
| 320 | OX40 | Mouse | 904 | GGTTTGGGAGTGTTAGGCA |
| 321 | OX40 | Mouse | 941 | CTCCTGGATCGGGGTCCTG |
| 322 | OX40 | Mouse | 1010 | GCCCCATAAAATCCACTCC |
| 323 | OX40 | Mouse | 1021 | GGGTTGTCCGTGCCCCATA |
| 324 | OX40 | Mouse | 1038 | GGCAGGCATCAGGATATGG |
| 325 | OX40 | Mouse | 1069 | GCCCAGCACCTAGAACGGT |
| 326 | OX40 | Mouse | 1080 | GCCCAGAGCCAGCCCAGCA |
| 327 | OX40 | Mouse | 1126 | TTAGGAGCACCACCAGGCA |

TABLE 3-continued

| Oligo #/SEQ ID NO: | Target | Species | Target Site | Sequence 5'→3' |
|---|---|---|---|---|
| 328 | OX40 | Human | 82 | CCCAGGAGGAGCAGAGCCG |
| 329 | OX40 | Human | 192 | TGCAGCGGCTCACCATCCC |
| 330 | OX40 | Human | 273 | AGGGCTTGCACGGCTTGGA |
| 331 | OX40 | Human | 300 | TCCCACTTCTGAGGTTACA |
| 332 | OX40 | Human | 312 | GCTTCCGCTCACTCCCACT |
| 333 | OX40 | Human | 342 | AGACTGTGTCCTGTGTGGC |
| 334 | OX40 | Human | 347 | GCGGCAGACTGTGTCCTGT |
| 335 | OX40 | Human | 401 | GGCACAGTCAACTCCAGGC |
| 336 | OX40 | Human | 462 | AGTTGGTCCAGGGCTTGCA |
| 337 | OX40 | Human | 485 | GGTGTGCTTCCCAGCCAAG |
| 338 | OX40 | Human | 746 | CCGGAGCAGGTACAGGGCC |
| 339 | OX40 | Human | 762 | GCAGCCTCTGGTCCCTCCG |
| 340 | OX40 | Human | 763 | GGCAGCCTCTGGTCCCTCC |
| 341 | OX40 | Human | 823 | TGCTCCTCTTGGATGGGGG |
| 342 | OX40 | Human | 865 | GGCCCAGGTCAGATCTTGG |
| 343 | OX40 | Human | 967 | GTTGGCCCAGGAGCGTGGC |
| 344 | OX40 | Human | 1036 | GCAGGAGGTATGCATGGCA |
| 345 | OX40 | Human | 1058 | GTTTTTATTGTGGTCCCGC |
| 346 | OX40 | Human | 1075 | GACTCCCGTCTGCCAAGGT |
| 347 | OX40L | Mouse | 141 | CCCTTCCCCTTCCATCTCT |
| 348 | OX40L | Mouse | 167 | TCCAGATTCTCATCCAGGG |
| 349 | OX40L | Mouse | 182 | GGCCTTGATCCGTTTTCCA |
| 350 | OX40L | Mouse | 218 | ACCACCAGCCTTAGCGTCT |
| 351 | OX40L | Mouse | 226 | TCCCAGAGACCACCAGCCT |
| 352 | OX40L | Mouse | 240 | CCCTGCTCCCTTGATCCCA |
| 353 | OX40L | Mouse | 303 | TGGAGGGTCCTTTGCCGGA |
| 354 | OX40L | Mouse | 399 | GTTCTGCACCTCCATAGTT |
| 355 | OX40L | Mouse | 454 | AGGAGCCCTTCAGGTAGAT |
| 356 | OX40L | Mouse | 565 | CCAAAGAGGCCACCACAGT |
| 357 | OX40L | Mouse | 650 | ACAATCAGCTCCCCATCAT |
| 358 | OX40L | Mouse | 753 | CCTGTGTCCCGTCCACCCT |
| 359 | OX40L | Mouse | 817 | AGGGTAGGCTCTGCATTCA |
| 360 | OX40L | Mouse | 895 | GCAGGCTCAAGGCAATCCT |
| 361 | OX40L | Mouse | 1069 | TGGACACCACCCTTTCCAT |
| 362 | OX40L | Mouse | 1157 | CCCCCATGAGATGAGAGAC |
| 363 | OX40L | Mouse | 1173 | AATCTTCTTTCCAAGCCCC |
| 364 | OX40L | Mouse | 1193 | AGTCCTGCTTTCCACGGGG |
| 365 | OX40L | Mouse | 1298 | GGTGGGTATCATAGTCCCT |

TABLE 3-continued

| Oligo #/SEQ ID NO: | Target | Species | Target Site | Sequence 5'→3' |
|---|---|---|---|---|
| 366 | OX40L | Mouse | 1439 | CCTTCTTGGCCTTTATCCT |
| 367 | OX40L | Human | 494 | GGGCTCCTCATCCTTCTGG |
| 368 | OX40L | Human | 712 | GTTCATGCTGGTGCCTGGT |
| 369 | OX40L | Human | 814 | GGGAGGGCCAGGATCTGCT |
| 370 | OX40L | Human | 1104 | CCTTCACTCCTTGCTCCTC |
| 371 | OX40L | Human | 1120 | GATTCATAACCCCACTCCT |
| 372 | OX40L | Human | 1139 | GTTCATACCACCTTTGGCA |
| 373 | OX40L | Human | 1276 | GGCTCTCTTCAAGTCCTGA |
| 374 | OX40L | Human | 1378 | CACATCCCCAGACAGTTCT |
| 375 | OX40L | Human | 1383 | AGCATCACATCCCCAGACA |
| 376 | OX40L | Human | 1492 | GTCCAGTTCCCTGCTATCC |
| 377 | OX40L | Human | 1569 | TGCTTTGCCTGTCTGTGGC |
| 378 | OX40L | Human | 1577 | GCATGTGTTGCTTTGCCTG |
| 379 | OX40L | Human | 1828 | ATTCCATTGAAGCCCTGGC |
| 380 | OX40L | Human | 2127 | CAGCCCTCCACCTTTCTGG |
| 381 | OX40L | Human | 2367 | GTCCACAGTAGGCCCTCCA |
| 382 | OX40L | Human | 2376 | CAGTGCCTGGTCCACAGTA |
| 383 | OX40L | Human | 2387 | AGTATTTAGCCCAGTGCCT |
| 384 | OX40L | Human | 2729 | CCCAAAGCGAGTGAGCACC |
| 385 | OX40L | Human | 2754 | ACATGGAAGAGCAGGCCA |
| 386 | OX40L | Human | 2808 | GGTGGAGTGAGGCTGGTGC |

Compound names for the 3$^{rd}$ generation antisense (3GA) compounds according to the invention are based on the target and oligonucleotide target site(s) as depicted Table 3. For example, "3GA 384" comprises two copies of Oligo # 384 linked at their 5' ends (e.g., 3'-CCACGAGTGAGC-GAAACCC-5'-X-5'-CCCAAAGCGAGTGAGCACC-3' (SEQ ID NOs: 384 and 384), wherein X represents a non-nucleotidic linker). Alternatively, a 3GA compound comprising two different oligonucleotides such as Oligo # 385 and Oligo # 386 (e.g., 3'-ACCGGACGAGAAGGG-TACA-5'-X-5'- GGTGGAGTGAGGCTGGTGC-3' (SEQ ID NOs: 385 and 386), wherein X represents a non-nucleotidic linker) will be referred to herein, for example, as "3GA 385/386".

Certain embodiments provide gene silencing compounds comprising two oligonucleotides independently selected from the oligonucleotides listed in Table 3. In certain embodiments, the gene silencing compounds comprise two oligonucleotides each, independently, comprising a portion of at least 12 contiguous nucleobases of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, or 386, or combinations thereof. In certain embodiments, the oligonucleotides of the gene silencing compound are the same. In certain embodiments, the oligonucleotides of the gene silencing compounds are different.

In certain embodiments, the gene silencing compounds comprise two oligonucleotides each, independently, comprising a portion of at least 12 contiguous nucleobases of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, or 386, and is at least 80% complimentary to its target site with SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, or SEQ ID NO: 406. In certain embodiments, the gene silencing compounds comprise two oligonucleotides each, independently, comprising a portion of at least 12 contiguous nucleobases of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, or 386, and is at least 85% complimentary to its target site with SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, or SEQ ID NO: 406. In certain embodiments, the gene silencing compounds comprise two oligonucleotides each, independently, comprising a portion of at least 12 contiguous nucleobases of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, or 386, and is at least 90% complimentary to its target site with SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, or SEQ ID NO: 406. In certain embodiments, the gene silencing compounds comprise two oligonucleotides each, independently, comprising a portion of at least 12 contiguous nucleobases of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, or 386, and is at least 95% complimentary to its target site with SEQ ID NO: 387, SEQ ID NO: 388, SEQ ID NO: 389, SEQ ID NO: 390, SEQ ID NO: 391, SEQ ID NO: 392, SEQ ID NO: 393, SEQ ID NO: 394, SEQ ID NO: 395, SEQ ID NO: 396, SEQ ID NO: 397, SEQ ID NO: 398, SEQ ID NO: 399, SEQ ID NO: 400, SEQ ID NO: 401, SEQ ID NO: 402, SEQ ID NO: 403, SEQ ID NO: 404, SEQ ID NO: 405, or SEQ ID NO: 406.

In certain embodiments, the gene silencing compounds comprise two oligonucleotides each, independently, comprising a portion of at least 12 contiguous nucleobases of SEQ ID NOs: 1, 2, 3, 4, 5, 6, 7, 8, 49, 50, 51, 52, 53, 54, 75, 76, 77, 78, 79, 80, 101, 102, 103, 104, 105, 106, 107, 108, 109, 110, 111, 112, 113, 114, 115, 116, 117, 118, 119, 120, 121, 122, 123, 124, 149, 150, 151, 152, 153, 154, 155, 156, 157, 158, 159, 160, 161, 162, 163, 164, 165, 166, 167, 168, 189, 190, 191, 192, 193, 194, 195, 196, 197, 198, 199, 200, 201, 202, 203, 204, 205, 206, 207, 208, 229, 230, 231, 232, 233, 234, 235, 236, 237, 238, 239, 240, 241, 242, 243, 244, 245, 246, 247, 248, 271, 272, 273, 274, 275, 276, 277, 278, 279, 280, 281, 282, 283, 284, 285, 286, 287, 308, 309, 310, 311, 312, 313, 314, 315, 316, 317, 318, 319, 320, 321, 322, 323, 324, 325, 326, 327, 347, 348, 349, 350, 351, 352, 353, 354, 355, 356, 357, 358, 359, 360, 361, 362, 363, 364, or 365, and is at least 80% complimentary to its target site with SEQ ID NO: 387, SEQ ID NO: 389, SEQ ID NO: 391, SEQ ID NO: 393, SEQ ID NO: 395, SEQ ID NO: 397, SEQ ID NO: 399, SEQ ID NO: 401, SEQ ID NO: 403, or SEQ ID NO: 405. In certain embodiments, the gene silencing compounds comprise two oligonucleotides each, independently, comprising a portion of at least 12 contiguous nucleobases of SEQ ID NOs: 1, 2, 3, 4, 5, 6, 7, 8, 49, 50, 51, 52, 53, 54, 75, 76, 77, 78, 79, 80, 101, 102, 103, 104, 105, 106, 107, 108, 109, 110, 111, 112, 113, 114, 115, 116, 117, 118, 119, 120, 121, 122, 123, 124, 149, 150, 151, 152, 153, 154, 155, 156, 157, 158, 159, 160, 161, 162, 163, 164, 165, 166, 167, 168, 189, 190, 191, 192, 193, 194, 195, 196, 197, 198, 199, 200, 201, 202, 203, 204, 205, 206, 207, 208, 229, 230, 231, 232, 233, 234, 235, 236, 237, 238, 239, 240, 241, 242, 243, 244, 245, 246, 247, 248, 271, 272, 273, 274, 275, 276, 277, 278, 279, 280, 281, 282, 283, 284, 285, 286, 287, 308, 309, 310, 311, 312, 313, 314, 315, 316, 317, 318, 319, 320, 321, 322, 323, 324, 325, 326, 327, 347, 348, 349, 350, 351, 352, 353, 354, 355, 356, 357, 358, 359, 360, 361, 362, 363, 364, or 365, and is at least 85% complimentary to its target site with SEQ ID NO: 387, SEQ ID NO: 389, SEQ ID NO: 391, SEQ ID NO: 393, SEQ ID NO: 395, SEQ ID NO: 397, SEQ ID NO: 399, SEQ ID NO: 401, SEQ ID NO: 403, or SEQ ID NO: 405. In certain embodiments, the gene silencing compounds comprise two oligonucleotides each, independently, comprising a portion of at least 12 contiguous nucleobases of SEQ ID NOs: 1, 2, 3, 4, 5, 6, 7, 8, 49, 50, 51, 52, 53, 54, 75, 76, 77, 78, 79, 80, 101, 102, 103, 104, 105, 106, 107, 108, 109, 110, 111, 112, 113, 114, 115, 116, 117, 118, 119, 120, 121, 122, 123, 124, 149, 150, 151, 152, 153, 154, 155, 156, 157, 158, 159, 160, 161, 162, 163, 164, 165, 166, 167, 168, 189, 190, 191, 192, 193, 194, 195, 196, 197, 198, 199, 200, 201, 202, 203, 204, 205, 206, 207, 208, 229, 230, 231, 232, 233, 234, 235, 236, 237, 238, 239, 240, 241, 242, 243, 244, 245, 246, 247, 248, 271, 272, 273, 274, 275, 276, 277, 278, 279, 280, 281, 282, 283, 284, 285, 286, 287, 308, 309, 310, 311, 312, 313, 314, 315, 316, 317, 318, 319, 320, 321, 322, 323, 324, 325, 326, 327, 347, 348, 349, 350, 351, 352, 353, 354, 355, 356, 357, 358, 359, 360, 361, 362, 363, 364, or 365, and is at least 90% complimentary to its target site with SEQ ID NO: 387, SEQ ID NO: 389, SEQ ID NO: 391, SEQ ID NO: 393, SEQ ID NO: 395, SEQ ID NO: 397, SEQ ID NO: 399, SEQ ID NO: 401, SEQ ID NO: 403, or SEQ ID NO: 405. In certain embodiments, the gene silencing compounds comprise two oligonucleotides each, independently, comprising a portion of at least 12 contiguous nucleobases of SEQ ID NOs: 1, 2, 3, 4, 5, 6, 7, 8, 49, 50, 51, 52, 53, 54, 75, 76, 77, 78, 79, 80, 101, 102, 103, 104, 105, 106, 107, 108, 109, 110, 111, 112, 113, 114, 115, 116, 117, 118, 119, 120, 121, 122, 123, 124, 149, 150, 151, 152, 153, 154, 155, 156, 157, 158, 159, 160, 161, 162, 163, 164, 165, 166, 167, 168, 189, 190, 191, 192, 193, 194, 195, 196, 197, 198, 199, 200, 201, 202, 203, 204, 205, 206, 207, 208, 229, 230, 231, 232, 233, 234, 235, 236, 237, 238, 239, 240, 241, 242, 243, 244, 245, 246, 247, 248, 271, 272, 273, 274, 275, 276, 277, 278, 279, 280, 281, 282, 283, 284, 285, 286, 287, 308, 309, 310, 311, 312, 313, 314, 315, 316, 317, 318, 319, 320, 321, 322, 323, 324, 325, 326, 327, 347, 348, 349, 350, 351, 352, 353, 354, 355, 356, 357, 358, 359, 360, 361, 362, 363, 364, or 365, and is at least 95% complimentary to its target site with SEQ ID NO: 387, SEQ ID NO: 389, SEQ ID NO: 391, SEQ ID NO: 393, SEQ ID NO: 395, SEQ ID NO: 397, SEQ ID NO: 399, SEQ ID NO: 401, SEQ ID NO: 403, or SEQ ID NO: 405.

In certain embodiments, the gene silencing compounds comprise two oligonucleotides each, independently, comprising a portion of at least 12 contiguous nucleobases of SEQ ID NOs: 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 55, 56, 57, 58, 59, 60, 61, 62, 63, 64, 65, 66, 67, 68, 69, 70, 71, 72, 73, 74, 81, 82, 83, 84, 85, 86, 87, 88, 89, 90, 91, 92, 93, 94, 95, 96, 97, 98, 99, 100, 125, 126, 127, 128, 129, 130, 131, 132, 133, 134, 135, 136, 137, 138, 139, 140, 141, 142, 143, 144, 145, 146, 147, 148, 169, 170, 171, 172, 173, 174, 175, 176, 177, 178, 179, 180, 181, 182, 183, 184, 185, 186, 187, 188, 209, 210, 211, 212, 213, 214, 215, 216, 217, 218, 219, 220, 221, 222, 223, 224, 225, 226, 227, 228, 249, 250, 251, 252, 253, 254, 255, 256, 257, 258, 259, 260, 261, 262, 263, 264, 265, 266, 267, 268, 269, 270, 288, 289, 290, 291, 292, 293, 294, 295, 296, 297, 298, 299, 300, 301, 302, 303, 304, 305, 306, 307, 328, 329, 330, 331, 332, 333, 334, 335, 336, 337, 338, 339, 340, 341, 342, 343, 344, 345, 346, 366, 367, 368, 369, 370, 371, 372, 373, 374, 375, 376, 377, 378, 379, 380, 381, 382, 383, 384, 385, or 386, and is at least 80% complimentary to its target site within SEQ ID NO: 388, SEQ ID NO: 390, SEQ ID NO: 392, SEQ ID NO: 394, SEQ ID NO: 396, SEQ ID NO: 398, SEQ ID NO: 400, SEQ ID NO: 402, SEQ ID NO: 404, or SEQ ID NO: 406. In certain embodiments, the gene silencing compounds comprise two oligonucleotides each, independently, comprising a portion of at least 12 contiguous nucleobases of SEQ ID NOs: 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 55, 56, 57, 58, 59, 60, 61, 62, 63, 64, 65, 66, 67, 68, 69, 70, 71, 72, 73, 74, 81, 82, 83, 84, 85, 86, 87, 88, 89, 90, 91, 92, 93, 94, 95, 96, 97, 98, 99, 100, 125, 126, 127, 128, 129, 130, 131, 132, 133, 134, 135, 136, 137, 138, 139, 140, 141, 142, 143, 144, 145, 146, 147, 148, 169, 170, 171, 172, 173, 174, 175, 176, 177, 178, 179, 180, 181, 182, 183, 184, 185, 186, 187, 188, 209, 210, 211, 212, 213, 214, 215, 216, 217, 218, 219, 220, 221, 222, 223, 224, 225, 226, 227, 228, 249, 250, 251, 252, 253, 254, 255, 256, 257, 258, 259, 260, 261, 262, 263, 264, 265, 266, 267, 268, 269, 270, 288, 289, 290, 291, 292, 293, 294, 295, 296, 297, 298, 299, 300, 301, 302, 303, 304, 305, 306, 307, 328, 329, 330, 331, 332, 333, 334, 335, 336, 337, 338, 339, 340, 341, 342, 343, 344, 345, 346, 366, 367, 368, 369, 370, 371, 372, 373, 374, 375, 376, 377, 378, 379, 380, 381, 382, 383, 384, 385, or 386, and is at least 85% complimentary to its target site within SEQ ID NO: 388, SEQ ID NO: 390, SEQ ID NO: 392, SEQ ID NO: 394, SEQ ID NO: 396, SEQ ID NO: 398, SEQ ID NO: 400, SEQ ID NO: 402, SEQ ID NO: 404, or SEQ ID NO: 406. In certain embodiments, the gene silencing compounds comprise two oligonucleotides each, independently, comprising a portion of at least 12 contiguous nucleobases of SEQ ID NOs: 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 55, 56, 57, 58, 59, 60, 61, 62, 63, 64, 65, 66, 67, 68, 69, 70, 71, 72, 73, 74, 81, 82, 83, 84, 85, 86, 87, 88, 89, 90, 91, 92, 93, 94, 95, 96, 97, 98, 99, 100, 125, 126, 127, 128, 129, 130, 131, 132, 133, 134, 135, 136, 137, 138, 139, 140, 141, 142, 143, 144, 145, 146, 147, 148, 169, 170, 171, 172, 173, 174, 175, 176, 177, 178, 179, 180, 181, 182, 183, 184, 185, 186, 187, 188, 209, 210, 211, 212, 213, 214, 215, 216, 217, 218, 219, 220, 221, 222, 223, 224, 225, 226, 227, 228, 249, 250, 251, 252, 253, 254, 255, 256, 257, 258, 259, 260, 261, 262, 263, 264, 265, 266, 267, 268, 269, 270, 288, 289, 290, 291, 292, 293, 294, 295, 296, 297, 298, 299, 300, 301, 302, 303, 304, 305, 306, 307, 328, 329, 330, 331, 332, 333, 334, 335, 336, 337, 338, 339, 340, 341, 342, 343, 344, 345, 346, 366, 367, 368, 369, 370, 371, 372, 373, 374, 375, 376, 377, 378, 379, 380, 381, 382, 383, 384, 385, or 386, and is at least 90% complimentary to its target site within SEQ ID NO: 388, SEQ ID NO: 390, SEQ ID NO: 392, SEQ ID NO: 394, SEQ ID NO: 396, SEQ ID NO: 398, SEQ ID NO: 400, SEQ ID NO: 402, SEQ ID NO: 404, or SEQ ID NO: 406. In certain embodiments, the gene silencing compounds comprise two oligonucleotides each, independently, comprising a portion of at least 12 contiguous nucleobases of SEQ ID NOs: 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 55, 56, 57, 58, 59, 60, 61, 62, 63, 64, 65, 66, 67, 68, 69, 70, 71, 72, 73, 74, 81, 82, 83, 84, 85, 86, 87, 88, 89, 90, 91, 92, 93, 94, 95, 96, 97, 98, 99, 100, 125, 126, 127, 128, 129, 130, 131, 132, 133, 134, 135, 136, 137, 138, 139, 140, 141, 142, 143, 144, 145, 146, 147, 148, 169, 170, 171, 172, 173, 174, 175, 176, 177, 178, 179, 180, 181, 182, 183, 184, 185, 186, 187, 188, 209, 210, 211, 212, 213, 214, 215, 216, 217, 218, 219, 220, 221, 222, 223, 224, 225, 226, 227, 228, 249, 250, 251, 252, 253, 254, 255, 256, 257, 258, 259, 260, 261, 262, 263, 264, 265, 266, 267, 268, 269, 270, 288, 289, 290, 291, 292, 293, 294, 295, 296, 297, 298, 299, 300, 301, 302, 303, 304, 305, 306, 307, 328, 329, 330, 331, 332, 333, 334, 335, 336, 337, 338, 339, 340, 341, 342, 343, 344, 345, 346, 366, 367, 368, 369, 370, 371, 372, 373, 374, 375, 376, 377, 378, 379, 380, 381, 382, 383, 384, 385, or 386, and is at least 95% complimentary to its target site within SEQ ID NO: 388, SEQ ID NO: 390, SEQ ID NO: 392, SEQ ID NO: 394, SEQ ID NO: 396, SEQ ID NO: 398, SEQ ID NO: 400, SEQ ID NO: 402, SEQ ID NO: 404, or SEQ ID NO: 406.

In certain embodiments, the gene silencing compounds comprise two oligonucleotides each, independently, comprising a portion of at least 12 contiguous nucleobases of SEQ ID NOs: 1, 2, 3, 4, 5, 6, 7, or 8, and is at least 80% complimentary to SEQ ID NO: 387.

In certain embodiments, the gene silencing compounds comprise two oligonucleotides each, independently, comprising a portion of at least 12 contiguous nucleobases of SEQ ID NOs: 1, 2, 3, 4, 5, 6, 7, or 8, and is at least 85% complimentary to SEQ ID NO: 387. In certain embodiments, the gene silencing compounds comprise two oligonucleotides each, independently, comprising a portion of at least 12 contiguous nucleobases of SEQ ID NOs: 1, 2, 3, 4, 5, 6, 7, or 8, and is at least 90% complimentary to SEQ ID NO: 387. In certain embodiments, the gene silencing compounds comprise two oligonucleotides each, independently, comprising a portion of at least 12 contiguous nucleobases of SEQ ID NOs: 1, 2, 3, 4, 5, 6, 7, or 8, and is at least 95% complimentary to SEQ ID NO: 387.

In certain embodiments, the gene silencing compounds comprise two oligonucleotides each, independently, comprising a portion of at least 12 contiguous nucleobases of SEQ ID NOs: 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, and is at least 80% complimentary to SEQ ID NO: 388. In certain embodiments, the gene silencing compounds comprise two oligonucleotides each, independently, comprising a portion of at least 12 contiguous nucleobases of SEQ ID NOs: 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, and is at least 85% complimentary to SEQ ID NO: 388. In certain embodiments, the gene silencing compounds comprise two oligonucleotides each, independently, comprising a portion of at least 12 contiguous nucleobases of SEQ ID NOs: 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, and is at least 90% complimentary to SEQ ID NO: 388. In certain embodiments, the gene silencing compounds comprise two oligonucleotides each, independently, comprising a portion of at least 12 contiguous nucleobases of SEQ ID NOs: 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, and is at least 95% complimentary to SEQ ID NO: 388.

In certain embodiments, the gene silencing compounds comprise two oligonucleotides each, independently, comprising a portion of at least 12 contiguous nucleobases of SEQ ID NOs: 49, 50, 51, 52, 53, 54, and is at least 80% complimentary to SEQ ID NO: 389. In certain embodiments, the gene silencing compounds comprise two oligonucleotides each, independently, comprising a portion of at least 12 contiguous nucleobases of SEQ ID NOs: 49, 50, 51, 52, 53, 54, and is at least 85% complimentary to SEQ ID NO: 389. In certain embodiments, the gene silencing compounds comprise two oligonucleotides each, independently, comprising a portion of at least 12 contiguous nucleobases of SEQ ID NOs: 49, 50, 51, 52, 53, 54, and is at least 90% complimentary to SEQ ID NO: 389. In certain embodiments, the gene silencing compounds comprise two oligonucleotides each, independently, comprising a portion of at least 12 contiguous nucleobases of SEQ ID NOs: 49, 50, 51, 52, 53, 54, and is at least 95% complimentary to SEQ ID NO: 389.

In certain embodiments, the gene silencing compounds comprise two oligonucleotides each, independently, comprising a portion of at least 12 contiguous nucleobases of SEQ ID NOs: 55, 56, 57, 58, 59, 60, 61, 62, 63, 64, 65, 66, 67, 68, 69, 70, 71, 72, 73, 74, and is at least 80% complimentary to SEQ ID NO: 390. In certain embodiments, the gene silencing compounds comprise two oligonucleotides each, independently, comprising a portion of at least 12 contiguous nucleobases of SEQ ID NOs: 55, 56, 57, 58, 59, 60, 61, 62, 63, 64, 65, 66, 67, 68, 69, 70, 71, 72, 73, 74, and is at least 85% complimentary to SEQ ID NO: 390. In certain embodiments, the gene silencing compounds comprise two oligonucleotides each, independently, comprising a portion of at least 12 contiguous nucleobases of SEQ ID NOs: 55, 56, 57, 58, 59, 60, 61, 62, 63, 64, 65, 66, 67, 68, 69, 70, 71, 72, 73, 74, and is at least 90% complimentary to SEQ ID NO: 390. In certain embodiments, the gene silencing compounds comprise two oligonucleotides each, independently, comprising a portion of at least 12 contiguous nucleobases of SEQ ID NOs: 55, 56, 57, 58, 59, 60, 61, 62, 63, 64, 65, 66, 67, 68, 69, 70, 71, 72, 73, 74, and is at least 95% complimentary to SEQ ID NO: 390.

In certain embodiments, the gene silencing compounds comprise two oligonucleotides each, independently, comprising a portion of at least 12 contiguous nucleobases of SEQ ID NOs: 75, 76, 77, 78, 79, 80, and is at least 80% complimentary to SEQ ID NO: 391. In certain embodiments, the gene silencing compounds comprise two oligonucleotides each, independently, comprising a portion of at least 12 contiguous nucleobases of SEQ ID NOs: 75, 76, 77, 78, 79, 80, and is at least 85% complimentary to SEQ ID NO: 391. In certain embodiments, the gene silencing compounds comprise two oligonucleotides each, independently, comprising a portion of at least 12 contiguous nucleobases of SEQ ID NOs: 75, 76, 77, 78, 79, 80, and is at least 90% complimentary to SEQ ID NO: 391. In certain embodiments, the gene silencing compounds comprise two oligonucleotides each, independently, comprising a portion of at least 12 contiguous nucleobases of SEQ ID NOs: 75, 76, 77, 78, 79, 80, and is at least 95% complimentary to SEQ ID NO: 391.

In certain embodiments, the gene silencing compounds comprise two oligonucleotides each, independently, comprising a portion of at least 12 contiguous nucleobases of SEQ ID NOs: 81, 82, 83, 84, 85, 86, 87, 88, 89, 90, 91, 92, 93, 94, 95, 96, 97, 98, 99, 100, and is at least 80% complimentary to SEQ ID NO: 392. In certain embodiments, the gene silencing compounds comprise two oligonucleotides each, independently, comprising a portion of at least 12 contiguous nucleobases of SEQ ID NOs: 81, 82, 83, 84, 85, 86, 87, 88, 89, 90, 91, 92, 93, 94, 95, 96, 97, 98, 99, 100, and is at least 85% complimentary to SEQ ID NO: 392. In certain embodiments, the gene silencing compounds comprise two oligonucleotides each, independently, comprising a portion of at least 12 contiguous nucleobases of SEQ ID NOs: 81, 82, 83, 84, 85, 86, 87, 88, 89, 90, 91, 92, 93, 94, 95, 96, 97, 98, 99, 100, and is at least 90% complimentary to SEQ ID NO: 392. In certain embodiments, the gene silencing compounds comprise two oligonucleotides each, independently, comprising a portion of at least 12 contiguous nucleobases of SEQ ID NOs: 81, 82, 83, 84, 85, 86, 87, 88, 89, 90, 91, 92, 93, 94, 95, 96, 97, 98, 99, 100, and is at least 95% complimentary to SEQ ID NO: 392.

In certain embodiments, the gene silencing compounds comprise two oligonucleotides each, independently, comprising a portion of at least 12 contiguous nucleobases of SEQ ID NOs: 101, 102, 103, 104, 105, 106, 107, 108, 109, 110, 111, 112, 113, 114, 115, 116, 117, 118, 119, 120, 121, 122, 123, 124, and is at least 80% complimentary to SEQ ID NO: 393. In certain embodiments, the gene silencing compounds comprise two oligonucleotides each, independently, comprising a portion of at least 12 contiguous nucleobases of SEQ ID NOs: 101, 102, 103, 104, 105, 106, 107, 108, 109, 110, 111, 112, 113, 114, 115, 116, 117, 118, 119, 120, 121, 122, 123, 124, and is at least 85% complimentary to SEQ ID NO: 393. In certain embodiments, the gene silencing compounds comprise two oligonucleotides each, independently, comprising a portion of at least 12 contiguous nucleobases of SEQ ID NOs: 101, 102, 103, 104, 105, 106, 107, 108, 109, 110, 111, 112, 113, 114, 115, 116, 117, 118, 119, 120, 121, 122, 123, 124, and is at least 90% complimentary to SEQ ID NO: 393. In certain embodiments, the gene silencing compounds comprise two oligonucleotides each, independently, comprising a portion of at least 12 contiguous nucleobases of SEQ ID NOs: 101, 102, 103, 104, 105, 106, 107, 108, 109, 110, 111, 112, 113, 114, 115, 116, 117, 118, 119, 120, 121, 122, 123, 124, and is at least 95% complimentary to SEQ ID NO: 393.

In certain embodiments, the gene silencing compounds comprise two oligonucleotides each, independently, comprising a portion of at least 12 contiguous nucleobases of SEQ ID NOs: 125, 126, 127, 128, 129, 130, 131, 132, 133, 134, 135, 136, 137, 138, 139, 140, 141, 142, 143, 144, 145, 146, 147, 148, and is at least 80% complimentary to SEQ ID NO: 394.

In certain embodiments, the gene silencing compounds comprise two oligonucleotides each, independently, comprising a portion of at least 12 contiguous nucleobases of SEQ ID NOs: 125, 126, 127, 128, 129, 130, 131, 132, 133, 134, 135, 136, 137, 138, 139, 140, 141, 142, 143, 144, 145, 146, 147, 148, and is at least 85% complimentary to SEQ ID NO: 394. In certain embodiments, the gene silencing compounds comprise two oligonucleotides each, independently, comprising a portion of at least 12 contiguous nucleobases of SEQ ID NOs: 125, 126, 127, 128, 129, 130, 131, 132, 133, 134, 135, 136, 137, 138, 139, 140, 141, 142, 143, 144, 145, 146, 147, 148, and is at least 90% complimentary to SEQ ID NO: 394. In certain embodiments, the gene silencing compounds comprise two oligonucleotides each, independently, comprising a portion of at least 12 contiguous nucleobases of SEQ ID NOs: 125, 126, 127, 128, 129, 130, 131, 132, 133, 134, 135, 136, 137, 138, 139, 140, 141, 142, 143, 144, 145, 146, 147, 148, and is at least 95% complimentary to SEQ ID NO: 394.

In certain embodiments, the gene silencing compounds comprise two oligonucleotides each, independently, comprising a portion of at least 12 contiguous nucleobases of SEQ ID NOs: 149, 150, 151, 152, 153, 154, 155, 156, 157, 158, 159, 160, 161, 162, 163, 164, 165, 166, 167, 168, and is at least 80% complimentary to SEQ ID NO: 395. In certain embodiments, the gene silencing compounds comprise two oligonucleotides each, independently, comprising a portion of at least 12 contiguous nucleobases of SEQ ID NOs: 149, 150, 151, 152, 153, 154, 155, 156, 157, 158, 159, 160, 161, 162, 163, 164, 165, 166, 167, 168, and is at least 85% complimentary to SEQ ID NO: 395. In certain embodiments, the gene silencing compounds comprise two oligonucleotides each, independently, comprising a portion of at least 12 contiguous nucleobases of SEQ ID NOs: 149, 150, 151, 152, 153, 154, 155, 156, 157, 158, 159, 160, 161, 162, 163, 164, 165, 166, 167, 168, and is at least 90% complimentary to SEQ ID NO: 395. In certain embodiments, the gene silencing compounds comprise two oligonucleotides each, independently, comprising a portion of at least 12 contiguous nucleobases of SEQ ID NOs: 149, 150, 151, 152, 153, 154, 155, 156, 157, 158, 159, 160, 161, 162, 163, 164, 165, 166, 167, 168, and is at least 95% complimentary to SEQ ID NO: 395.

In certain embodiments, the gene silencing compounds comprise two oligonucleotides each, independently, comprising a portion of at least 12 contiguous nucleobases of SEQ ID NOs: 169, 170, 171, 172, 173, 174, 175, 176, 177, 178, 179, 180, 181, 182, 183, 184, 185, 186, 187, 188, and is at least 80% complimentary to SEQ ID NO: 396. In certain embodiments, the gene silencing compounds comprise two oligonucleotides each, independently, comprising a portion of at least 12 contiguous nucleobases of SEQ ID NOs: 169, 170, 171, 172, 173, 174, 175, 176, 177, 178, 179, 180, 181, 182, 183, 184, 185, 186, 187, 188, and is at least 85% complimentary to SEQ ID NO: 396. In certain embodiments, the gene silencing compounds comprise two oligonucleotides each, independently, comprising a portion of at least 12 contiguous nucleobases of SEQ ID NOs: 169, 170, 171, 172, 173, 174, 175, 176, 177, 178, 179, 180, 181, 182, 183, 184, 185, 186, 187, 188, and is at least 90% complimentary to SEQ ID NO: 396. In certain embodiments, the gene silencing compounds comprise two oligonucleotides each, independently, comprising a portion of at least 12 contiguous nucleobases of SEQ ID NOs: 169, 170, 171, 172, 173, 174, 175, 176, 177, 178, 179, 180, 181, 182, 183, 184, 185, 186, 187, 188, and is at least 95% complimentary to SEQ ID NO: 396.

In certain embodiments, the gene silencing compounds comprise two oligonucleotides each, independently, comprising a portion of at least 12 contiguous nucleobases of SEQ ID NOs: 189, 190, 191, 192, 193, 194, 195, 196, 197, 198, 199, 200, 201, 202, 203, 204, 205, 206, 207, 208, and is at least 80% complimentary to SEQ ID NO: 397. In certain embodiments, the gene silencing compounds comprise two oligonucleotides each, independently, comprising a portion of at least 12 contiguous nucleobases of SEQ ID NOs: 189, 190, 191, 192, 193, 194, 195, 196, 197, 198, 199, 200, 201, 202, 203, 204, 205, 206, 207, 208, and is at least 85% complimentary to SEQ ID NO: 397. In certain embodiments, the gene silencing compounds comprise two oligonucleotides each, independently, comprising a portion of at least 12 contiguous nucleobases of SEQ ID NOs: 189, 190, 191, 192, 193, 194, 195, 196, 197, 198, 199, 200, 201, 202, 203, 204, 205, 206, 207, 208, and is at least 90% complimentary to SEQ ID NO: 397. In certain embodiments, the gene silencing compounds comprise two oligonucleotides each, independently, comprising a portion of at least 12 contiguous nucleobases of SEQ ID NOs: 189, 190, 191, 192, 193, 194, 195, 196, 197, 198, 199, 200, 201, 202, 203, 204, 205, 206, 207, 208, and is at least 95% complimentary to SEQ ID NO: 397.

In certain embodiments, the gene silencing compounds comprise two oligonucleotides each, independently, comprising a portion of at least 12 contiguous nucleobases of SEQ ID NOs: 209, 210, 211, 212, 213, 214, 215, 216, 217, 218, 219, 220, 221, 222, 223, 224, 225, 226, 227, 228, and is at least 80% complimentary to SEQ ID NO: 398. In certain embodiments, the gene silencing compounds comprise two oligonucleotides each, independently, comprising a portion of at least 12 contiguous nucleobases of SEQ ID NOs: 209, 210, 211, 212, 213, 214, 215, 216, 217, 218, 219, 220, 221, 222, 223, 224, 225, 226, 227, 228, and is at least 85% complimentary to SEQ ID NO: 398. In certain embodiments, the gene silencing compounds comprise two oligonucleotides each, independently, comprising a portion of at least 12 contiguous nucleobases of SEQ ID NOs: 209, 210, 211, 212, 213, 214, 215, 216, 217, 218, 219, 220, 221, 222, 223, 224, 225, 226, 227, 228, and is at least 90% complimentary to SEQ ID NO: 398. In certain embodiments, the gene silencing compounds comprise two oligonucleotides each, independently, comprising a portion of at least 12 contiguous nucleobases of SEQ ID NOs: 209, 210, 211, 212, 213, 214, 215, 216, 217, 218, 219, 220, 221, 222, 223, 224, 225, 226, 227, 228, and is at least 95% complimentary to SEQ ID NO: 398.

In certain embodiments, the gene silencing compounds comprise two oligonucleotides each, independently, comprising a portion of at least 12 contiguous nucleobases of SEQ ID NOs: 229, 230, 231, 232, 233, 234, 235, 236, 237, 238, 239, 240, 241, 242, 243, 244, 245, 246, 247, 248, and is at least 80% complimentary to SEQ ID NO: 399. In certain embodiments, the gene silencing compounds comprise two oligonucleotides each, independently, comprising a portion of at least 12 contiguous nucleobases of SEQ ID NOs: 229, 230, 231, 232, 233, 234, 235, 236, 237, 238, 239, 240, 241, 242, 243, 244, 245, 246, 247, 248, and is at least 85% complimentary to SEQ ID NO: 399. In certain embodiments, the gene silencing compounds comprise two oligonucleotides each, independently, comprising a portion of at least 12 contiguous nucleobases of SEQ ID NOs: 229, 230, 231, 232, 233, 234, 235, 236, 237, 238, 239, 240, 241, 242, 243, 244, 245, 246, 247, 248, and is at least 90% complimentary to SEQ ID NO: 399. In certain embodiments, the gene silencing compounds comprise two oligonucleotides each, independently, comprising a portion of at least 12 contiguous nucleobases of SEQ ID NOs: 229, 230, 231, 232, 233, 234, 235, 236, 237, 238, 239, 240, 241, 242, 243, 244, 245, 246, 247, 248, and is at least 95% complimentary to SEQ ID NO: 399.

In certain embodiments, the gene silencing compounds comprise two oligonucleotides each, independently, comprising a portion of at least 12 contiguous nucleobases of SEQ ID NOs: 249, 250, 251, 252, 253, 254, 255, 256, 257, 258, 259, 260, 261, 262, 263, 264, 265, 266, 267, 268, 269, 270, and is at least 80% complimentary to SEQ ID NO: 400. In certain embodiments, the gene silencing compounds comprise two oligonucleotides each, independently, comprising a portion of at least 12 contiguous nucleobases of SEQ ID NOs: 249, 250, 251, 252, 253, 254, 255, 256, 257, 258, 259, 260, 261, 262, 263, 264, 265, 266, 267, 268, 269, 270, and is at least 85% complimentary to SEQ ID NO: 400. In certain embodiments, the gene silencing compounds comprise two oligonucleotides each, independently, comprising a portion of at least 12 contiguous nucleobases of SEQ ID NOs: 249, 250, 251, 252, 253, 254, 255, 256, 257, 258, 259, 260, 261, 262, 263, 264, 265, 266, 267, 268, 269, 270, and is at least 90% complimentary to SEQ ID NO: 400. In certain embodiments, the gene silencing compounds comprise two oligonucleotides each, independently, comprising a portion of at least 12 contiguous nucleobases of SEQ ID NOs: 249, 250, 251, 252, 253, 254, 255, 256, 257, 258, 259, 260, 261, 262, 263, 264, 265, 266, 267, 268, 269, 270, and is at least 95% complimentary to SEQ ID NO: 400.

In certain embodiments, the gene silencing compounds comprise two oligonucleotides each, independently, comprising a portion of at least 12 contiguous nucleobases of SEQ ID NOs: 271, 272, 273, 274, 275, 276, 277, 278, 279, 280, 281, 282, 283, 284, 285, 286, 287, and is at least 80% complimentary to SEQ ID NO: 401. In certain embodiments, the gene silencing compounds comprise two oligonucleotides each, independently, comprising a portion of at least 12 contiguous nucleobases of SEQ ID NOs: 271, 272, 273, 274, 275, 276, 277, 278, 279, 280, 281, 282, 283, 284, 285, 286, 287, and is at least 85% complimentary to SEQ ID NO: 401. In certain embodiments, the gene silencing compounds comprise two oligonucleotides each, independently, comprising a portion of at least 12 contiguous nucleobases of SEQ ID NOs: 271, 272, 273, 274, 275, 276, 277, 278, 279, 280, 281, 282, 283, 284, 285, 286, 287, and is at least 90% complimentary to SEQ ID NO: 401. In certain embodiments, the gene silencing compounds comprise two oligonucleotides each, independently, comprising a portion of at least 12 contiguous nucleobases of SEQ ID NOs: 271, 272, 273, 274, 275, 276, 277, 278, 279, 280, 281, 282, 283, 284, 285, 286, 287, and is at least 95% complimentary to SEQ ID NO: 401.

In certain embodiments, the gene silencing compounds comprise two oligonucleotides each, independently, comprising a portion of at least 12 contiguous nucleobases of SEQ ID NOs: 288, 289, 290, 291, 292, 293, 294, 295, 296, 297, 298, 299, 300, 301, 302, 303, 304, 305, 306, 307, and is at least 80% complimentary to SEQ ID NO: 402. In certain embodiments, the gene silencing compounds comprise two oligonucleotides each, independently, comprising a portion of at least 12 contiguous nucleobases of SEQ ID NOs: 288, 289, 290, 291, 292, 293, 294, 295, 296, 297, 298, 299, 300, 301, 302, 303, 304, 305, 306, 307, and is at least 85% complimentary to SEQ ID NO: 402. In certain embodiments, the gene silencing compounds comprise two oligonucleotides each, independently, comprising a portion of at least 12 contiguous nucleobases of SEQ ID NOs: 288, 289, 290, 291, 292, 293, 294, 295, 296, 297, 298, 299, 300, 301, 302, 303, 304, 305, 306, 307, and is at least 90% complimentary to SEQ ID NO: 402. In certain embodiments, the gene silencing compounds comprise two oligonucleotides each, independently, comprising a portion of at least 12 contiguous nucleobases of SEQ ID NOs: 288, 289, 290, 291, 292, 293, 294, 295, 296, 297, 298, 299, 300, 301, 302, 303, 304, 305, 306, 307, and is at least 95% complimentary to SEQ ID NO: 402.

In certain embodiments, the gene silencing compounds comprise two oligonucleotides each, independently, comprising a portion of at least 12 contiguous nucleobases of SEQ ID NOs: 308, 309, 310, 311, 312, 313, 314, 315, 316, 317, 318, 319, 320, 321, 322, 323, 324, 325, 326, 327, and is at least 80% complimentary to SEQ ID NO: 403. In certain embodiments, the gene silencing compounds comprise two oligonucleotides each, independently, comprising a portion of at least 12 contiguous nucleobases of SEQ ID NOs: 308, 309, 310, 311, 312, 313, 314, 315, 316, 317, 318, 319, 320, 321, 322, 323, 324, 325, 326, 327, and is at least 85% complimentary to SEQ ID NO: 403. In certain embodiments, the gene silencing compounds comprise two oligonucleotides each, independently, comprising a portion of at least 12 contiguous nucleobases of SEQ ID NOs: 308, 309, 310, 311, 312, 313, 314, 315, 316, 317, 318, 319, 320, 321, 322, 323, 324, 325, 326, 327, and is at least 90% complimentary to SEQ ID NO: 403. In certain embodiments, the gene silencing compounds comprise two oligonucleotides each, independently, comprising a portion of at least 12 contiguous nucleobases of SEQ ID NOs: 308, 309, 310, 311, 312, 313, 314, 315, 316, 317, 318, 319, 320, 321, 322, 323, 324, 325, 326, 327, and is at least 95% complimentary to SEQ ID NO: 403.

In certain embodiments, the gene silencing compounds comprise two oligonucleotides each, independently, comprising a portion of at least 12 contiguous nucleobases of SEQ ID NOs: 328, 329, 330, 331, 332, 333, 334, 335, 336, 337, 338, 339, 340, 341, 342, 343, 344, 345, 346, and is at least 80% complimentary to SEQ ID NO: 404. In certain embodiments, the gene silencing compounds comprise two oligonucleotides each, independently, comprising a portion of at least 12 contiguous nucleobases of SEQ ID NOs: 328, 329, 330, 331, 332, 333, 334, 335, 336, 337, 338, 339, 340, 341, 342, 343, 344, 345, 346, and is at least 85% complimentary to SEQ ID NO: 404. In certain embodiments, the gene silencing compounds comprise two oligonucleotides each, independently, comprising a portion of at least 12 contiguous nucleobases of SEQ ID NOs: 328, 329, 330, 331, 332, 333, 334, 335, 336, 337, 338, 339, 340, 341, 342, 343, 344, 345, 346, and is at least 90% complimentary to SEQ ID NO: 404. In certain embodiments, the gene silencing compounds comprise two oligonucleotides each, independently, comprising a portion of at least 12 contiguous nucleobases of SEQ ID NOs: 328, 329, 330, 331, 332, 333, 334, 335, 336, 337, 338, 339, 340, 341, 342, 343, 344, 345, 346, and is at least 95% complimentary to SEQ ID NO: 404.

In certain embodiments, the gene silencing compounds comprise two oligonucleotides each, independently, comprising a portion of at least 12 contiguous nucleobases of SEQ ID NOs: 347, 348, 349, 350, 351, 352, 353, 354, 355, 356, 357, 358, 359, 360, 361, 362, 363, 364, 365, and is at least 80% complimentary to SEQ ID NO: 405. In certain embodiments, the gene silencing compounds comprise two oligonucleotides each, independently, comprising a portion of at least 12 contiguous nucleobases of SEQ ID NOs: 347, 348, 349, 350, 351, 352, 353, 354, 355, 356, 357, 358, 359, 360, 361, 362, 363, 364, 365, and is at least 85% complimentary to SEQ ID NO: 405. In certain embodiments, the gene silencing compounds comprise two oligonucleotides each, independently, comprising a portion of at least 12 contiguous nucleobases of SEQ ID NOs: 347, 348, 349, 350, 351, 352, 353, 354, 355, 356, 357, 358, 359, 360, 361, 362, 363, 364, 365, and is at least 90% complimentary to SEQ ID NO: 405. In certain embodiments, the gene silencing compounds comprise two oligonucleotides each, independently, comprising a portion of at least 12 contiguous nucleobases of SEQ ID NOs: 347, 348, 349, 350, 351, 352, 353, 354, 355, 356, 357, 358, 359, 360, 361, 362, 363, 364, 365, and is at least 95% complimentary to SEQ ID NO: 405.

In certain embodiments, the gene silencing compounds comprise two oligonucleotides each, independently, comprising a portion of at least 12 contiguous nucleobases of SEQ ID NOs: 366, 367, 368, 369, 370, 371, 372, 373, 374, 375, 376, 377, 378, 379, 380, 381, 382, 383, 384, 385, or 386, and is at least 80% complimentary to SEQ ID NO: 406. In certain embodiments, the gene silencing compounds comprise two oligonucleotides each, independently, comprising a portion of at least 12 contiguous nucleobases of SEQ ID NOs: 366, 367, 368, 369, 370, 371, 372, 373, 374, 375, 376, 377, 378, 379, 380, 381, 382, 383, 384, 385, or 386, and is at least 85% complimentary to SEQ ID NO: 406. In certain embodiments, the gene silencing compounds comprise two oligonucleotides each, independently, comprising a portion of at least 12 contiguous nucleobases of SEQ ID NOs: 366, 367, 368, 369, 370, 371, 372, 373, 374, 375, 376, 377, 378, 379, 380, 381, 382, 383, 384, 385, or 386, and is at least 90% complimentary to SEQ ID NO: 406.

In certain embodiments, the gene silencing compounds comprise two oligonucleotides each, independently, comprising a portion of at least 12 contiguous nucleobases of SEQ ID NOs: 366, 367, 368, 369, 370, 371, 372, 373, 374, 375, 376, 377, 378, 379, 380, 381, 382, 383, 384, 385, or 386, and is at least 95% complimentary to SEQ ID NO: 406.

In certain embodiments, the invention provides a composition comprising a 3GA compound according to the invention and one or more vaccines, antigens, antibodies, cytotoxic agents, chemotherapeutic agents (both traditional chemotherapy and modern targeted therapies), kinase inhibitors, allergens, antibiotics, agonist, antagonist, antisense oligonucleotides, ribozymes, RNAi molecules, siRNA molecules, miRNA molecules, aptamers, proteins, gene therapy vectors, DNA vaccines, adjuvants, co-stimulatory molecules or combinations thereof.

In certain embodiments, the invention provides a method for inhibiting PD1, PDL1, IDO1, LAG3, TIM3, CTLA4, IDO2, CEACAM1, OX40, and/or OX40L mRNA or protein expression, the method comprising contacting a cell with a gene silencing compound according to the invention. In certain embodiments, the cell can be contacted with two or more gene silencing compounds targeting different regions of the same checkpoint. In certain embodiments, the cell can be contacted with two or more gene silencing compounds targeting different checkpoints.

Certain embodiments further provide a method to reduce PD1, PDL1, IDO1, LAG3, TIM3, CTLA4, IDO2, CEACAM1, OX40, and/or or OX40L mRNA or protein expression in an animal comprising administering to the animal a gene silencing compound or composition as described herein to reduce PD1, PDL1, IDO1, LAG3, TIM3, CTLA4, IDO2, CEACAM1, OX40, or OX40L mRNA or protein expression in the animal. In certain embodiments, the animal is a human. In certain embodiments, reducing PD1, PDL1, IDO1, LAG3, TIM3, CTLA4, IDO2, CEACAM1, OX40, or OX40L mRNA or protein expression prevents, treats, ameliorates, or slows progression of disease. In certain embodiments reducing PD1, PDL1, IDO1, LAG3, TIM3, CTLA4, IDO2, CEACAM1, OX40, or OX40L mRNA or protein expression inhibits immune system tolerance. In certain embodiments two or more gene silencing compounds targeting different regions of the same checkpoint can be administered. In certain embodiments two or more gene silencing compounds targeting different checkpoints can be administered.

In certain embodiments provided are methods for inhibiting immune system tolerance to tumors comprising administering to the animal a gene silencing compound or composition as described herein to reduce PD1, PDL1, IDO1, LAG3, TIM3, CTLA4, IDO2, CEACAM1, OX40, and/or OX40L mRNA or protein expression in the animal. In certain embodiments, the animal is a human. In certain embodiments, the gene silencing compound or composition as described herein is administered intratumorally. Thus, the inhibition of PD1, PDL1, IDO1, LAG3, TIM3, CTLA4, IDO2, CEACAM1, OX40, or OX40L mRNA or protein expression may provide a potentially useful immunotherapy strategy for patients with cancer. In certain embodiments two or more gene silencing compounds targeting different regions of the same checkpoint can be administered. In certain embodiments two or more gene silencing compounds targeting different checkpoints can be administered.

In certain embodiments provided are methods for preventing tumor growth and tumor volume. In certain embodiments provided are methods for reducing tumor growth and tumor volume.

In certain embodiments provided are methods, compounds, and compositions for the treatment, prevention, or amelioration of diseases, disorders, and conditions associated with PD1, PDL1, IDO1, LAG3, TIM3, CTLA4, IDO2, CEACAM1, OX40, or OX40L in an individual in need thereof. Also contemplated are methods and compounds for the preparation of a medicament for the treatment, prevention, or amelioration of a disease, disorder, or condition associated with PD1, PDL1, IDO1, LAG3, TIM3, CTLA4, IDO2, CEACAM1, OX40, or OX40L. In certain embodiments two or more gene silencing compounds targeting different regions of the same checkpoint can be administered. In certain embodiments two or more gene silencing compounds targeting different checkpoints can be administered.

PD1, PDL1, IDO1, LAG3, TIM3, CTLA4, IDO2, CEACAM1, OX40, or OX40L associated diseases, disorders, and conditions include hyperproliferative diseases, e.g., cancer, carcinomas, sarcomas, lymphomas, and leukemias as well as associated malignancies and metastases. PD1, PDL1, IDO1, LAG3, TIM3, CTLA4, IDO2, CEACAM1, OX40, or OX40L associated diseases, disorders, and conditions can also include autoimmune diseases and disorders.

In certain embodiments provided are PD1, PDL1, IDO1, LAG3, TIM3, CTLA4, IDO2, CEACAM1, OX40, or OX40L gene silencing compounds for use in treating, preventing, or ameliorating a PD1, PDL1, IDO1, LAG3, TIM3, CTLA4, IDO2, CEACAM1, OX40, or OX40L associated disease. In certain embodiments, PD1, PDL1, IDO1, LAG3, TIM3, CTLA4, IDO2, CEACAM1, OX40, or OX40L gene silencing compounds are capable of inhibiting the expression of PD1, PDL1, IDO1, LAG3, TIM3, CTLA4, IDO2, CEACAM1, OX40, or OX40L mRNA and/or PD1, PDL1, IDO1, LAG3, TIM3, CTLA4, IDO2, CEACAM1, OX40, or OX40L protein in a cell, tissue, or animal.

Certain embodiments provide methods comprising administering to an animal a gene silencing compounds as described herein. In certain embodiments two or more gene silencing compounds targeting different regions of the same checkpoint can be administered. In certain embodiments two or more gene silencing compounds targeting different checkpoints can be administered.

Also provided are methods and gene silencing compounds for the preparation of a medicament for the treatment, prevention, or amelioration of disease.

Certain embodiments provide the use of gene silencing compounds as described herein in the manufacture of a medicament for treating, ameliorating, or preventing disease.

Certain embodiments provide gene silencing compounds as described herein for use in treating, preventing, or ameliorating disease as described herein by combination therapy with an additional agent or therapy as described herein. Agents or therapies can be co-administered or administered concomitantly.

Certain embodiments provide the use of a gene silencing compound as described herein in the manufacture of a medicament for treating, preventing, or ameliorating disease as described herein by combination therapy with an additional agent or therapy as described herein. Agents or therapies can be co-administered or administered concomitantly.

Certain embodiments provide the use of a gene silencing compound as described herein in the manufacture of a medicament for treating, preventing, or ameliorating disease as described herein in a patient who is subsequently administered an additional agent or therapy as described herein.

In any of the methods according to the invention, the gene silencing compound according to the invention can variously act by producing direct gene expression modulation effects alone and/or in combination with any other agent useful for treating or preventing the disease or condition that does not diminish the gene expression modulation effect of the gene silencing compound according to the invention. In any of the methods according to the invention, the agent(s) useful for treating or preventing the disease or condition includes, but is not limited to, vaccines, antigens, antibodies, preferably monoclonal antibodies, cytotoxic agents, kinase inhibitors, allergens, antibiotics, siRNA molecules, antisense oligonucleotides, TLR antagonist (e.g. antagonists of TLR3 and/or TLR7 and/or antagonists of TLR8 and/or antagonists of TLR9), chemotherapeutic agents (both traditional chemotherapy and modern targeted therapies), targeted therapeutic agents, activated cells, peptides, proteins, gene therapy vectors, peptide vaccines, protein vaccines, DNA vaccines, adjuvants, and co-stimulatory molecules (e.g. cytokines, chemokines, protein ligands, trans-activating factors, peptides or peptides comprising modified amino acids), or combinations thereof. For example, in the treatment of cancer, it is contemplated that the oligonucleotide-based compound according to the invention may be administered in combination with one or more chemotherapeutic compound, targeted therapeutic agent and/or monoclonal antibody. Alternatively, the agent can include DNA vectors encoding for antigen or allergen. Alternatively, the gene silencing compound according to the invention can be administered in combination with other compounds (for example lipids or liposomes) to enhance the specificity or magnitude of the gene expression modulation of the oligonucleotide-based compound according to the invention.

In any of the methods according to the invention, administration of gene silencing compounds according to the invention, alone or in combination with any other agent, can be by any suitable route, including, without limitation, parenteral, mucosal, oral, sublingual, intratumoral, transdermal, topical, inhalation, intrathecal, intranasal, aerosol, intraocular, intratracheal, intrarectal, vaginal, by gene gun, dermal patch or in eye drop or mouthwash form. In any of the methods according to the invention, administration of gene silencing compounds according to the invention, alone or in combination with any other agent, can be directly to a tissue or organ such as, but not limited to, the bladder, liver, lung, kidney or lung. In certain embodiments, administration of gene silencing compounds according to the invention, alone or in combination with any other agent, is by intratumoral administration. In certain embodiments, administration of gene silencing compounds according to the invention, alone or in combination with any other agent, is by mucosal administration. In certain embodiments, administration of gene silencing compounds according to the invention, alone or in combination with any other agent, is by oral administration. In certain embodiments, administration of gene silencing compounds according to the invention, alone or in combination with any other agent, is by intrarectal administration. In certain embodiments, administration of gene silencing compounds according to the invention, alone or in combination with any other agent, is by intrathecal administration. In certain embodiments, administration of gene silencing compounds according to the invention, alone or in combination with any other agent, is directly to the bladder. In certain embodiments, administration of gene silencing compounds according to the invention, alone or in combination with any other agent, is directly to the lung.

Administration of the therapeutic compositions of gene silencing compounds according to the invention can be carried out using known procedures using an effective amount and for periods of time effective to reduce symptoms or surrogate markers of the disease. For example, an effective amount of a gene silencing compound according to the invention for treating a disease and/or disorder could be that amount necessary to alleviate or reduce the symptoms, or delay or ameliorate the disease and/or disorder. In the context of administering a composition that modulates gene expression, an effective amount of a gene silencing compound according to the invention is an amount sufficient to achieve the desired modulation as compared to the gene expression in the absence of the gene silencing compound according to the invention. The effective amount for any particular application can vary depending on such factors as the disease or condition being treated, the particular compound being administered, the size of the subject, or the severity of the disease or condition. One of ordinary skill in the art can empirically determine the effective amount of a particular compound without necessitating undue experimentation.

When administered systemically, the therapeutic composition is preferably administered at a sufficient dosage to attain a blood level of gene silencing compound according to the invention from about 0.0001 micromolar to about 10 micromolar. For localized administration, much lower concentrations than this may be effective, and much higher concentrations may be tolerated. Preferably, a total dosage of gene silencing compound according to the invention ranges from about 0.001 mg per patient per day to about 200 mg per kg body weight per day. In certain embodiments, the total dosage may be 0.08, 0.16, 0.32, 0.48, 0.32, 0.64, 1, 10 or 30 mg/kg body weight administered daily, twice weekly or weekly. It may be desirable to administer simultaneously, or sequentially a therapeutically effective amount of one or more of the therapeutic compositions of the invention to an individual as a single treatment episode.

The methods according to this aspect of the invention are useful for model studies of gene expression. The methods are also useful for the prophylactic or therapeutic treatment of human or animal disease. For example, the methods are useful for pediatric and veterinary inhibition of gene expression applications.

The examples below are intended to further illustrate certain preferred embodiments of the invention, and are not intended to limit the scope of the invention.

EXAMPLE 1

Preparation of Oligonucleotide-based Compounds

The oligonucleotide-based compounds of the invention were chemically synthesized using phosphoramidite chemistry on automated DNA/RNA synthesizer. TAC protected (Except U) 2'—O-TBDMS RNA monomers, A, G, C and U, were purchased from Sigma-Aldrich. 7-deaza-G, inosine and loxoribine monomers were purchased from ChemGenes Corporation. 0.25M 5-ethylthio-1H-tetrazole, PAC-anhydride Cap A and Cap B were purchased from Glen Research. 3% trichloroacetic acid (TCA) in dichloromethane (DCM) and 5% 3H-1,2-Benzodithiole-3-one-1,1-dioxide (Beaucage reagent) were made in house.

Oligonucleotide-based compounds of the invention were synthesized at 1-2 μM scale using a standard RNA synthesis protocol.

Cleavage and Base Deprotection

Oligonucleotide-based compounds of the invention were cleaved from solid support and the solution was further heated at 65° C. to removing protecting groups of exo cyclic-amines. The resulting solution was dried completely in a SpeedVac.

IE HPLC Purification

Oligonucleotide-based compounds of the invention were purified by ion exchange HPLC.

Column: Dionex DNAPac 100 column (22×250)
Column Heater: ChromTech TL-105 HPLC column heater, temperature is set to 80° C.
Buffer A: 20 mM Tris-HCl, pH 7.0, 20% acetonitrile
Buffer B: 3.0 M NaCl, 20 mM Tris-HCl, pH 7.0, 20% acetonitrile
Flow rate: 10 ml/min
Gradient:

| |
|---|
| 0-2 min: 0% B |
| 2-11 min: 0% B to 35% B |
| 11-41 min: 35% B to 90% B |
| 41-45 min: 100% B |

Crude solution of oligonucleotide-based compounds of the invention was injected into HPLC. Above gradient is performed and the fractions were collected. All fractions containing more than 90% desired product were mixed, and then the solution was concentrated to almost dry by RotoVap. RNAse-free water was added to make final volume of 10 ml.

C-18 Reversed Phase Desalting

CC-18 Sep-Pak cartridge purchased from Waters was first conditioned with 10 ml of acetonitrile followed by 10 ml of 0.5 M sodium acetate. 10 ml of the solution of oligonucleotide-based compounds of the invention was loaded. 15 ml of water was then used to wash out the salt. The oligonucleotide-based compounds of the invention was eluted out by 1 ml of 50% acetonitrile in water.

The solution is placed in SpeedVac for 30 minutes. The remaining solution was filter through a 0.2 micro filter and then was lyophilized to dryness. The solid was then re-dissolved in water to make the desired concentration.

The final solution was stored below 0° C.

Capillary Electrophoresis

Oligonucleotide-based compounds of the invention were analyzed by capillary electrophoresis according to the following conditions.

Instrument: Beckman 5010
Capillary: 62 cm ssDNA capillary
Sample preparation: 0.2 OD of oligonucleotide-based composition according to the
  invention was dissolved in 200 ul of RNAse-free water.
Injection: electro-kinetic injection at 5 KV for 5 seconds.
Running condition: 14 KV for 50 minutes at 30° C.

Ion Exchange HPLC analysis

Oligonucleotide-based compounds of the invention were analyzed by ion exchange HPLC according to the following conditions:

Column: Dionex DNAPac guard column (22×250)
Column Heater: ChromTech TL-105 HPLC column heater, temperature is set to 80° C.
Buffer A: 100 mM Tris-HCl, pH 8.0, 20% acetonitrile
Buffer B: 2.0 M LiCl, 100 mM Tris-HCl, pH 8.0, 20% acetonitrile
Flow rate: 2 ml/min
Gradient:

| |
|---|
| 0-2 min: 0% B |
| 2-10 min: 0% B to 100% B |
| 10-15 min: 100% B |

PAGE Analysis 0.3 OD of oligonucleotide-based compounds of the invention was loaded on 20% polyacrylamide gel and was running at constant power of 4 watts for approximately 5 hours. The gel was viewed under short wavelength UV light.

Dual Luciferase Reporter System Assay

Hepa 1-6 cells are co-transfected with GSO and target plasmid simultaneously using LIPOFECTAMINE® 2000 on day one (20,000 c/well). RLuc siRNA was used as the positive control and GSO mu/hu universal control was used as the negative control. On day two (24 hours post-transfection), luminescence measurements for both reporter genes are taken separately: Firefly luciferase: expression serves as the normalizer for the assay; Renilla luciferase: substrate includes a "stop" reagent to quench luminescence from firefly. Separate luminescence measurements are taken to correspond to renilla-target transcript expression. Substrate includes DTT to lyse cells. Results are shown in Table 4A and Table 4B.

TABLE 4A

| 3GA # | GSO sequence | Each of the sequences are disclosed as SEQ ID NO: | % KD Luciferase Screen (25 nM) |
|---|---|---|---|
| 1 | 3'-GACCGTACACCCAGGCCG-5'-X-5'-GCCGGACCCACATGCCCAG-3' | 1 | 72.80 |
| 2 | 3'-ACACCCAGGCCGTCCATGG-5'-X-5'-GGTACCTGCCGGACCCACA-3' | 2 | 74.00 |
| 3 | 3'-TCGACCGTTAGTCCCACCG-5'-X-5'-GCCACCCTGATTGCCAGCT-3' | 3 | 73.10 |
| 4 | 3'-TCTCCCTCGTTTACGGTGG-5'-X-5'-GGTGGCATTTGCTCCCTCT-3' | 4 | 62.60 |
| 5 | 3'-TCCCTGCTCTCTTCTGTGG-5'-X-5'-GGTGTCTTCTCTCGTCCCT-3' | 5 | 20.80 |
| 6 | 3'-ACCCTGCATCCCCGAGTCG-5'-X-5'-GCTGAGCCCCTACGTCCCA-3' | 6 | 52.80 |
| 7 | 3'-TGTTCCACGTCTCGACCCC-5'-X-5'-CCCCAGCTCTGCACCTTGT-3' | 7 | 76.50 |
| 8 | 3'-TCCCTTGGTCGTCTCGATC-5'-X-5'-CTAGCTCTGCTGGTTCCCT-3' | 8 | 71.50 |
| 9 | 3'-TACGTCTAGGGTGTCCGCG-5'-X-5'-GCGCCTGTGGGATCTGCAT-3' | 9 | 76.32 |
| 10 | 3'-CACGATGTTGACCCGACCG-5'-X-5'-GCCAGCCCAGTTGTAGCAC-3' | 10 | 80.51 |
| 11 | 3'-TCGTTGGTCTGCCTGTTCG-5'-X-5'-GCTTGTCCGTCTGGTTGCT-3' | 11 | 64.70 |

TABLE 4A-continued

| 3GA # | GSO sequence | Each of the sequences are disclosed as SEQ ID NO: | % KD Luciferase Screen (25 nM) |
|---|---|---|---|
| 12 | 3'-TCCCACTGTCTCTCTTCCC-5'-X-5'-CCCTTCTCTCTGTCACCCT-3' | 12 | 63.00 |
| 13 | 3'-CCCACTGTCTCTCTTCCCG-5'-X-5'-GCCCTTCTCTCTGTCACCC-3' | 13 | 71.30 |
| 14 | 3'-CCACTGTCTCTCTTCCCGT-5'-X-5'-TGCCCTTCTCTCTGTCACC-3' | 14 | 61.91 |
| 15 | 3'-ACGATCAGACCCAGGACCG-5'-X-5'-GCCAGGACCCAGACTAGCA-3' | 15 | 53.22 |
| 16 | 3'-TCAGACCCAGGACCGGCAG-5'-X-5'-GACGGCCAGGACCCAGACT-3' | 16 | 73.38 |
| 17 | 3'-GTGACTCCGGACTCCTACC-5'-X-5'-CCATCCTCAGGCCTCAGTG-3' | 17 | 53.02 |
| 18 | 3'-GACTCCGGACTCCTACCTG-5'-X-5'-GTCCATCCTCAGGCCTCAG-3' | 18 | 51.62 |
| 19 | 3'-CTCCGGACTCCTACCTGTG-5'-X-5'-GTGTCCATCCTCAGGCCTC-3' | 19 | 56.13 |
| 20 | 3'CCGGACTCCTACCTGTGAC-5'-X-5'-CAGTGTCCATCCTCAGGCC-3' | 20 | 46.22 |
| 21 | 3'-CCTCTTCGTCCGTCCCACG-5'-X-5'-GCACCCTGCCTGCTTCTCC-3' | 21 | 68.62 |
| 22 | 3'-TCTTCGTCCGTCCCACGTC-5'-X-5'-CTGCACCCTGCCTGCTTCT-3' | 22 | 73.88 |
| 23 | 3'-GGGTCCGTCGTCCACAGTG-5'-X-5'-GTGACACCTGCTGCCTGGG-3' | 23 | 61.92 |
| 24 | 3'-GGATGTCCCTCCCGGTCTA-5'-X-5'-ATCTGGCCCTCCCTGTAGG-3' | 24 | 40.93 |
| 25 | 3'-ATGTCCCTCCCGGTCTACG-5'-X-5'-GCATCTGGCCCTCCCTGTA-3' | 25 | 41.82 |
| 26 | 3'-GTCCCTCCCGGTCTACGTC-5'-X-5'-CTGCATCTGGCCCTCCCTG-3' | 26 | 57.94 |
| 27 | 3'-CCCTCCCGGTCTACGTCAG-5'-X-5'-GACTGCATCTGGCCCTCCC-3' | 27 | 58.14 |
| 28 | 3'-CTCCCGGTCTACGTCAGTG-5'-X-5'-GTGACTGCATCTGGCCCTC-3' | 28 | 63.13 |
| 29 | 3'-GGTTCTGACCCGTGTCCTC-5'-X-5'-CTCCTGTGCCCAGTCTTGG-3' | 29 | 59.63 |
| 30 | 3'-TCGAGGACCGACACCACCC-5'-X-5'-CCCACCACAGCCAGGAGCT-3' | 30 | 77.64 |
| 31 | 3'-CGAGGACCGACACCACCCG-5'-X-5'-GCCCACCACAGCCAGGAGC-3' | 31 | 80.53 |
| 32 | 3'-GGGTCCGTCGTGGAGTCCG-5'-X-5'-GCCTGAGGTGCTGCCTGGG-3' | 32 | 62.62 |
| 33 | 3'-CCGTCCCTTCGACTCCGTC-5'-X-5'-CTGCCTCAGCTTCCCTGCC-3' | 33 | 73.27 |
| 34 | 3'-CGTCCCTTCGACTCCGTCA-5'-X-5'-ACTGCCTCAGCTTCCCTGC-3' | 34 | 78.22 |
| 35 | 3'-CCCGTCCGTCTCGACCTCC-5'-X-5'-CCTCCAGCTCTGCCTGCCC-3' | 35 | 60.58 |
| 36 | 3'-CCGTCCGTCTCGACCTCCG-5'-X-5'-GCCTCCAGCTCTGCCTGCC-3' | 36 | 54.52 |
| 37 | 3'-CAGGGTTCCAGTCCTCCCG-5'-X-5'-GCCCTCCTGACCTTGGGAC-3' | 37 | 71.63 |
| 38 | 3'-GGGTTCCAGTCCTCCCGTC-5'-X-5'-CTGCCCTCCTGACCTTGGG-3' | 38 | 69.94 |
| 39 | 3'-GTTCCAGTCCTCCCGTCCC-5'-X-5'-CCCTGCCCTCCTGACCTTG-3' | 39 | 71.58 |
| 40 | 3'-GTCCCGGACCCACCCTTCC-5'-X-5'-CCTTCCCACCCAGGCCCTG-3' | 40 | 57.15 |
| 41 | 3'-CCCGGACCCACCCTTCCAT-5'-X-5'-TACCTTCCCACCCAGGCCC-3' | 41 | 51.93 |
| 42 | 3'-CGGACCCACCCTTCCATGT-5'-X-5'-TGTACCTTCCCACCCAGGC-3' | 42 | 31.04 |
| 43 | 3'GACCCACCCTTCCATGTCC-5'-X-5'-CCTGTACCTTCCCACCCAG-3' | 43 | 44.89 |
| 44 | 3'-GTCCCGGTGGTCGTAGGTC-5'-X-5'-CTGGATGCTGGTGGCCCTG-3' | 44 | 61.72 |
| 45 | 3'-TCCCGGTGGTCGTAGGTCC-5'-X-5'-CCTGGATGCTGGTGGCCCT-3' | 45 | 52.12 |
| 46 | 3'TCCGTGGACTCACCGACCC-5'-X-5'-CCCAGCCACTCAGGTGCCT-3' | 46 | 76.87 |
| 47 | 3'-CTCACCGACCCTGTTCCCT-5'-X-5'-TCCCTTGTCCCAGCCACTC-3' | 47 | 68.50 |
| 48 | 3'-CACCGACCCTGTTCCCTAG-5'-X-5'-GATCCCTTGTCCCAGCCAC-3' | 48 | 74.30 |
| 49 | 3'-GCCCTCGACCTGGACGAAC-5'-X-5'-CAAGCAGGTCCAGCTCCCG-3' | 49 | 67.80 |
| 50 | 3'-TGTCGTTGAAGTCCCCCTC-5'-X-5'-CTCCCCCTGAAGTTGCTGT-3' | 50 | 76.40 |
| 51 | 3'-TGCCACCACGCCTGATGTT-5'-X-5'-TTGTAGTCCGCACCACCGT-3' | 51 | 84.40 |
| 52 | 3'-TCCCTTGTGTCTCCAGTGG-5'-X-5'-GGTGACCTCTGTGTTCCCT-3' | 52 | 58.30 |
| 53 | 3'-ATCCCTCCGTCTCCGTCCG-5'-X-5'-GCCTGCCTCTGCCTCCCTA-3' | 53 | 76.10 |
| 54 | 3'-GACTTCCTTGTCCGACCCG-5'-X-5'-GCCCAGCCTGTTCCTTCAG-3' | 54 | 70.30 |

Where X is glycerol

TABLE 4B

| 3GA # | % KD Luciferase Screen (25 nM) |
|---|---|
| 55 | 72.55 |
| 56 | 16.18 |
| 57 | 68.59 |
| 58 | 82.08 |

TABLE 4B-continued

| 3GA # | % KD Luciferase Screen (25 nM) |
|---|---|
| 59 | 64.04 |
| 60 | 61.19 |
| 61 | 55.65 |
| 62 | 29.88 |
| 63 | 44.00 |
| 64 | 73.27 |
| 65 | 69.04 |
| 66 | 76.39 |
| 67 | 67.30 |
| 68 | 84.30 |
| 69 | 61.65 |
| 70 | 59.28 |
| 71 | 60.44 |
| 72 | 49.61 |
| 73 | 65.21 |
| 74 | 52.34 |
| 75 | 82.43 |
| 76 | 68.25 |
| 77 | 83.97 |
| 78 | 82.25 |
| 79 | 67.84 |
| 80 | 41.54 |
| 81 | 80.09 |
| 82 | 53.95 |
| 83 | 74.05 |
| 84 | 2.78 |
| 85 | 53.89 |
| 86 | 53.70 |
| 87 | 34.15 |
| 88 | 77.07 |
| 89 | 23.27 |
| 90 | 41.99 |
| 91 | 41.36 |
| 92 | 60.45 |
| 93 | 58.99 |
| 94 | 74.51 |
| 95 | 10.33 |
| 96 | 9.46 |
| 97 | 42.36 |
| 98 | 27.05 |
| 99 | 24.30 |
| 100 | 10.54 |
| 101 | 85.55 |
| 102 | 60.69 |
| 103 | 63.04 |
| 104 | 59.83 |
| 105 | 57.80 |
| 106 | 71.35 |
| 107 | 74.39 |
| 108 | 74.04 |
| 109 | 80.27 |
| 110 | 89.98 |
| 111 | 86.33 |
| 112 | 88.35 |
| 113 | 84.67 |
| 114 | 57.13 |
| 115 | 56.03 |
| 116 | 77.36 |
| 117 | 72.63 |
| 118 | 74.24 |
| 119 | 79.93 |
| 120 | 86.42 |
| 121 | 57.13 |
| 122 | 49.63 |
| 123 | 65.62 |
| 124 | 72.63 |
| 125 | 96.00 |
| 126 | 71.45 |
| 127 | −0.08 |
| 128 | 4.49 |
| 129 | 60.37 |
| 130 | 67.01 |
| 131 | 10.42 |
| 132 | 72.11 |
| 133 | 66.46 |
| 134 | 58.22 |
| 135 | 40.56 |
| 136 | 75.82 |
| 137 | 69.22 |
| 138 | 69.06 |
| 139 | 79.03 |
| 140 | 10.17 |
| 141 | 25.50 |
| 142 | 84.19 |
| 143 | 81.61 |
| 144 | 70.57 |
| 145 | 78.67 |
| 146 | 66.46 |
| 147 | 58.98 |
| 148 | 69.06 |
| 149 | 97.18 |
| 150 | 81.25 |
| 151 | 30.14 |
| 152 | 73.42 |
| 153 | 79.87 |
| 154 | 63.67 |
| 155 | 71.18 |
| 156 | 64.26 |
| 157 | 84.39 |
| 158 | 91.96 |
| 159 | 87.62 |
| 160 | 85.37 |
| 161 | 90.51 |
| 162 | 90.48 |
| 163 | 88.20 |
| 164 | 82.16 |
| 165 | 79.86 |
| 166 | 88.55 |
| 167 | 91.35 |
| 168 | 81.98 |
| 169 | 94.67 |
| 170 | 84.41 |
| 171 | 82.59 |
| 172 | 31.12 |
| 173 | 67.25 |
| 174 | 36.58 |
| 175 | 55.38 |
| 176 | 73.10 |
| 177 | 77.05 |
| 178 | 91.25 |
| 179 | 83.86 |
| 180 | 85.21 |
| 181 | 72.85 |
| 182 | 61.27 |
| 183 | 81.35 |
| 184 | 68.97 |
| 185 | 67.13 |
| 186 | 57.30 |
| 187 | 79.41 |
| 188 | 41.38 |
| 189 | 50.80 |
| 190 | 52.18 |
| 191 | 63.14 |
| 192 | 82.52 |
| 193 | 41.99 |
| 194 | 73.39 |
| 195 | 76.17 |
| 196 | 85.66 |
| 197 | 98.60 |
| 198 | 47.11 |
| 199 | 42.47 |
| 200 | 87.17 |
| 201 | 74.36 |
| 202 | 58.24 |
| 203 | 59.21 |
| 204 | 42.36 |
| 205 | 74.17 |
| 206 | 76.54 |
| 207 | 30.41 |
| 208 | 68.55 |

TABLE 4B-continued

| 3GA # | % KD Luciferase Screen (25 nM) |
|---|---|
| 209 | 69.73 |
| 210 | 59.73 |
| 211 | 54.92 |
| 212 | 56.90 |
| 213 | 69.09 |
| 214 | 77.40 |
| 215 | 39.73 |
| 216 | 39.23 |
| 217 | 41.13 |
| 218 | 23.48 |
| 219 | 79.92 |
| 220 | 29.57 |
| 221 | 64.50 |
| 222 | 73.89 |
| 223 | 81.38 |
| 224 | 70.29 |
| 225 | 69.92 |
| 226 | 81.70 |
| 227 | 59.46 |
| 228 | 81.39 |
| 229 | 88.01 |
| 230 | 75.84 |
| 231 | 58.18 |
| 232 | 29.33 |
| 233 | 61.77 |
| 234 | 72.38 |
| 235 | 45.83 |
| 236 | 39.94 |
| 237 | 66.24 |
| 238 | 49.78 |
| 239 | 23.03 |
| 240 | 59.57 |
| 241 | 41.65 |
| 242 | 44.50 |
| 243 | 18.23 |
| 244 | 37.51 |
| 245 | 58.43 |
| 246 | 70.66 |
| 247 | 74.80 |
| 248 | 70.32 |
| 249 | 90.70 |
| 250 | 73.19 |
| 251 | 81.50 |
| 252 | 87.92 |
| 253 | 76.82 |
| 254 | 55.60 |
| 255 | 42.30 |
| 256 | 44.52 |
| 257 | 81.17 |
| 258 | 64.45 |
| 259 | 79.46 |
| 260 | 41.81 |
| 261 | 46.85 |
| 262 | 83.04 |
| 263 | 78.00 |
| 264 | 69.88 |
| 265 | 59.09 |
| 266 | 39.05 |
| 267 | 34.97 |
| 268 | 83.20 |
| 269 | 86.16 |
| 270 | 49.03 |
| 271 | 70.17 |
| 272 | 86.40 |
| 273 | 67.96 |
| 274 | 44.65 |
| 275 | 65.68 |
| 276 | 66.68 |
| 277 | 76.67 |
| 278 | 39.46 |
| 279 | 69.63 |
| 280 | 68.44 |
| 281 | 57.77 |
| 282 | 67.85 |
| 283 | 61.74 |
| 284 | 69.87 |
| 285 | 58.11 |
| 286 | 41.07 |
| 287 | 42.40 |
| 288 | 42.09* |
| 289 | 61.77* |
| 290 | 33.46* |
| 291 | 49.08* |
| 292 | 43.43* |
| 293 | 40.08* |
| 294 | 57.06* |
| 295 | 87.34* |
| 296 | 76.54* |
| 297 | 36.96* |
| 298 | 96.71* |
| 299 | 70.53* |
| 300 | 88.21* |
| 301 | 76.86* |
| 302 | 85.21* |
| 303 | 74.25* |
| 304 | 70.61* |
| 305 | 83.52* |
| 306 | 65.18* |
| 307 | 84.36* |
| 308 | 91.72 |
| 309 | 93.78 |
| 310 | 86.49 |
| 311 | 79.67 |
| 312 | 78.18 |
| 313 | 68.73 |
| 314 | 49.06 |
| 315 | 51.92 |
| 316 | 64.80 |
| 317 | 49.86 |
| 318 | 60.88 |
| 319 | 54.14 |
| 320 | 54.27 |
| 321 | 64.20 |
| 322 | 57.54 |
| 323 | 64.73 |
| 324 | 24.73 |
| 325 | −3.86 |
| 326 | 58.29 |
| 327 | 85.58 |
| 328 | 38.27 |
| 329 | 54.35 |
| 330 | 37.69 |
| 331 | 42.71 |
| 332 | 77.86 |
| 333 | 34.95 |
| 334 | 29.20 |
| 335 | 41.76 |
| 336 | 55.25 |
| 337 | 56.23 |
| 338 | 44.34 |
| 339 | 42.26 |
| 340 | 33.54 |
| 341 | 32.88 |
| 342 | 46.91 |
| 343 | 25.39 |
| 344 | 53.54 |
| 345 | 68.08 |
| 346 | 65.26 |
| 347 | 70.49 |
| 348 | 33.62 |
| 349 | 78.29 |
| 350 | 87.30 |
| 351 | 92.56 |
| 352 | 82.30 |
| 353 | 62.64 |
| 354 | 84.10 |
| 355 | 72.48 |
| 356 | 87.25 |
| 357 | 68.93 |
| 358 | 77.23 |

TABLE 4B-continued

| 3GA # | % KD Luciferase Screen (25 nM) |
|---|---|
| 359 | 74.70 |
| 360 | 43.71 |
| 361 | 86.31 |
| 362 | 52.57 |
| 363 | 38.62 |
| 364 | 64.49 |
| 365 | 66.70 |
| 366 | 77.24 |
| 367 | 89.81 |
| 368 | 77.82 |
| 369 | 62.31 |
| 370 | 80.21 |
| 371 | 58.76 |
| 372 | 71.34 |
| 373 | 65.23 |
| 374 | 65.58 |
| 375 | 78.67 |
| 376 | 67.01 |
| 377 | 32.15 |
| 378 | 49.07 |
| 379 | 53.07 |
| 380 | 58.24 |
| 381 | 72.09 |
| 382 | 63.90 |
| 383 | 68.54 |
| 384 | 15.69 |
| 385 | 25.43 |
| 386 | 40.49 |

For 3GA compounds numbers 55 through 386 listed in Table 4B, glycerol is the non-nucleotidic linker.

Flow Cytometric Analysis

Whole blood samples with anticoagulant EDTA from mice in study were stained for 30 minutes in the dark at room temperature with the following labeled antibodies from BD Biosciences in the presence of mouse Fc blocker (Affymetrix eBioscience, 14-0161): rat anti-mouse CD3-Alexa Fluor 647 (557869), rat anti-mouse CD4-Alexa Fluor 647 (557681), rat anti-mouse CD8-Alexa Fluor 488 (557668) or the corresponding isotype controls. Red blood cells were lysed with freshly prepared 1×RBC lysis buffer (eBioscience, 00-4300) and washed with flow cytometry staining buffer (BD Biosciences, 554657). Resuspended cell suspensions in the flow cytometry staining buffer were run on BD Accuri C6 to acquire data and analyzed by FLOWJO (TreeStar).

IC50 Analysis

Hepa 1-6 cells are co-transfected with 3GA and target plasmid simultaneously using LIPOFECTAMINE® 2000 on day one (20,000 c/well). Concentration of 3GAs were ranging from 0.019 to 41.7 nM with a 3-fold increment. RLuc siRNA was used as the positive control and 3GA mu/hu universal control was used as the negative control. On day two (24 hours post-transfection), luminescence measurements for both reporter genes are taken separately: Firefly luciferase: expression serves as the normalizer for the assay; Renilla luciferase: substrate includes a "stop" reagent to quench luminescence from firefly. Separate luminescence measurements are taken to correspond to renilla-target transcript expression. Substrate includes DTT to lyse cells. IC50 of 3GAs was calculated using GraphPad Prism 6. Results are shown in Table 5.

TABLE 5

| 3GA #/SEQ ID NO: | target | Target Site | GSO Sequence 5' to 3' | $IC_{50}$ (nM) |
|---|---|---|---|---|
| 75 | mIDO1 | 138 | CTAGCCACAAGGACCCAGG | 33.1 |
| 81 | hIDO1 | 172 | GCAGAGCAAAGCCCACTTC | 3.49 |
| 92 | | 1239 | GCCTCCAGTTCCTTTGGCT | 1.53 |
| 3 | mPD1 | 115 | GCCACCCTGATTGCCAGCT | 59.0 |
| 10 | hPD1 | 108 | GCCAGCCCAGTTGTAGCAC | 3.87 |
| 33 | | 1591 | CTGCCTCAGCTTCCCTGCC | 1.57 |
| 46 | | 2024 | CCCAGCCACTCAGGTGCCT | 3.16 |
| 54 | mPD-L1 | 3311 | GCCCAGCCTGTTCCTTCAG | 14.4 |
| 55 | hPD-L1 | 571 | GGTAGCCCTCAGCCTGACA | 5.00 |
| 58 | | 1080 | CCCACATTGCCTGCATCCC | 2.42 |
| 64 | | 1855 | TCTGTTTGCTTCCTCAGCT | 2.51 |
| 158 | mTIM3 | 1425 | ACTTATCACCCTCCTGCCT | 5.55 |
| 169 | hTIM3 | 59 | CTGCCAGGTCTACAGTCAC | 13.8 |
| 180 | | 1506 | CAGCACCCAGTTTTCCCTA | 6.10 |
| 183 | | 1716 | ATCCCAGCCACTCAGGAGG | 32.7 |
| 110 | mLAG3 | 1108 | GCTCCAGACCCAGAACCTT | 6.49 |
| 124 | hLAG3 | 1356/1369 | GACAGTGGCATTGAGCTGC | 11.9 |
| 122 | | 1822/1841 | GCTCCAGCTCCTCTATCTT | 9.10 |

TABLE 5-continued

| 3GA #/SEQ ID NO: | target | Target Site | GSO Sequence 5' to 3' | $IC_{50}$ (nM) |
|---|---|---|---|---|
| 143 | | 1848 | GGTTCTTGCTCCAGCTCCT | 5.03 |
| 195 | mCTLA4 | 563 | GTTGCCCATGCCCACAAAG | 19.6 |
| 225 | hCTLA4 | 1822 | GCCTTCTTCTGTCCATGGC | 1.71 |
| 247 | mIDO2 | 2748 | GGTGACTTCCAGGTCTGCA | 0.247 |
| 249 | hIDO2 | 156 | GGTGTCCATTGCCTTCTGT | 2.73 |
| 259 | | 1137 | AGTCACCACTTTCCTTGCT | 3.36 |
| 262 | | 1363 | GGCTTCCCATGCTTTGCCT | 1.28 |
| 361 | mOX40L | 1069 | TGGACACCACCCTTTCCAT | 0.673 |
| 368 | hOX40L | 712 | GTTCATGCTGGTGCCTGGT | 0.553 |
| 370 | | 1104 | CCTTCACTCCTTGCTCCTC | 5.01 |

In Vivo Mouse Tumor Model

Colon tumor can be implanted in BALB/c mice by subcutaneous injection of $10^6$ CT26.WT cells at right flank (Tumor 1) and $10^6$ CT26.CL25 cells at left flank (Tumor 2) on day 0. Treatment can be initiated on day 6 or when tumor size reached to 70 to 80 mm$^3$ by intra-tumor injection of gene silencing compound according to the invention at various dosages (e.g., 2 mg/kg, 5 mg/kg, 12.5 mg/kg, or 25 mg/kg) on day 6, 10, 13, 16, 20, and 22.

Tumor growth can be monitored twice per week throughout the study period. The study can be terminated with blood, spleen and tumor tissues collected for further evaluation. T lymphocyte population in blood and spleen samples were detected and analyzed by flow cytometry. Spleen IFN-γ-producing cells were detected with ELISPOT assay after culture of spleen cells for 24 hours with tumor antigen beta-gal or AH1 peptide. Tumor tissues were analyzed for gene expression by RT-PCR.

EQUIVALENTS

Those skilled in the art will recognize, or be able to ascertain, using no more than routine experimentation, numerous equivalents to the specific substances and procedures described herein. For example, antisense oligonucleotides that overlap with the oligonucleotides may be used. Such equivalents are considered to be within the scope of this invention, and are covered by the following claims.

What is claimed is:

1. A 3rd generation antisense (3GA) compound comprising two oligonucleotides linked at their 5' ends, each oligonucleotide, independently, consisting of 12 to 30 nucleotides having at least 12 contiguous nucleobases complementary to an equal length portion of SEQ ID NO: 397, or SEQ ID NO: 398.

2. The 3GA compound according to claim 1, wherein each oligonucleotide, independently, consists of 12 to 30 nucleotides having at least 12 contiguous nucleobases complementary to an equal length portion of SEQ ID NO: 398.

3. The 3GA compound according to claim 1, wherein the nucleobase sequence of each oligonucleotide is, independently, at least 90% complementary over its entire length to a nucleobase sequence of SEQ ID NO: 397 or 398.

4. The 3GA compound according to claim 3, wherein the nucleobase sequence of each oligonucleotide is, independently, at least 90% complementary over its entire length to a nucleobase sequence of SEQ ID NO: 398.

5. The 3GA compound according to claim 1, wherein each oligonucleotide, independently, comprises at least 12 contiguous nucleobases of SEQ ID NO: 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, or 228.

6. The 3GA compound according to claim 5, wherein each oligonucleotide, independently, comprises at least 12 contiguous nucleobases of SEQ ID NOs: 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, or 228, and is at least 80% complimentary to its target sequence within SEQ ID NO: SEQ ID NO: 397 or SEQ ID NO: 398.

7. The 3GA compound according to claim 6, wherein each oligonucleotide, independently, comprises at least 12 contiguous nucleobases of SEQ ID NOs: 209, 210, 211, 212, 213, 214, 215, 216, 217, 218, 219, 220, 221, 222, 223, 224, 225, 226, 227, or 228, and is at least 80% complimentary to its target sequence within SEQ ID NO: 398.

8. A composition comprising a 3GA compound according to claim 1 and a pharmaceutically acceptable carrier.

9. A method for inhibiting CTLA4 mRNA or protein expression, the method comprising contacting a cell with at least one 3GA compound according to claim 1.

10. The method according to claim 9, wherein the cell is contacted with two or more 3GA compounds targeting different regions of CTLA4.

11. A method for inhibiting immune system tolerance to tumors comprising administering to an animal at least one 3GA compound according to claim 1 or composition according to claim 8 to reduce CTLA4 mRNA or protein expression.

12. A method for the treatment of a disease, disorder, or condition associated with CTLA4 in an individual in need thereof, the method comprising administering at least one 3GA compound according to claim 1.

13. The method according to claim 12, wherein the disease, disorder, or condition is a hyperproliferative disease or an autoimmune disease.

14. The method according to claim 13, wherein the hyperproliferative disease is selected from cancer, carcinoma, sarcoma, lymphoma, leukemia, or an associated malignancy or metastasis.

15. The method according to claim 11, wherein the 3GA compound is administered intratumorally.

16. The 3GA compound according to claim 1, wherein each oligonucleotide, independently, is SEQ ID NO: 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, or 228.

17. The 3GA compound according to claim 16, wherein the two oligonucleotides have the same sequence.

* * * * *

SEQUENCE LISTING

<160> NUMBER OF SEQ ID NOS: 406

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 1
gccggaccca catgcccag                                                  19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 2
ggtacctgcc ggacccaca                                                  19

<210> SEQ ID NO 3
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 3
gccaccctga ttgccagct                                                    19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggtggcattt gctccctct                                                    19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggtgtcttct ctcgtccct                                                    19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gctgagcccc tacgtccca                                                    19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccccagctct gcaccttgt                                                    19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctagctctgc tggttccct                                                    19

<210> SEQ ID NO 9
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 9
gcgcctgtgg gatctgcat                                               19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gccagcccag ttgtagcac                                               19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcttgtccgt ctggttgct                                               19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cccttctctc tgtcaccct                                               19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcccttctct ctgtcaccc                                               19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgcccttctc tctgtcacc                                               19

<210> SEQ ID NO 15
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 15
gccaggaccc agactagca                                                19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gacggccagg acccagact                                                19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccatcctcag gcctcagtg                                                19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtccatcctc aggcctcag                                                19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtgtccatcc tcaggcctc                                                19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cagtgtccat cctcaggcc                                                19

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 21
gcaccctgcc tgcttctcc                                          19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctgcaccctg cctgcttct                                          19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtgacacctg ctgcctggg                                          19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
atctggccct ccctgtagg                                          19

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcatctggcc ctccctgta                                          19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ctgcatctgg ccctccctg                                          19

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gactgcatct ggccctccc                                                19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtgactgcat ctggccctc                                                19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctcctgtgcc cagtcttgg                                                19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cccaccacag ccaggagct                                                19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcccaccaca gccaggagc                                                19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcctgaggtg ctgcctggg                                                19

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 33
ctgcctcagc ttccctgcc                                                19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
actgcctcag cttccctgc                                                19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cctccagctc tgcctgccc                                                19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcctccagct ctgcctgcc                                                19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gccctcctga ccttgggac                                                19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ctgccctcct gaccttggg                                                19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
```

```
ccctgccctc ctgaccttg                                                    19
```

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40

```
ccttcccacc caggccctg                                                    19
```

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41

```
taccttccca cccaggccc                                                    19
```

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42

```
tgtaccttcc cacccaggc                                                    19
```

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43

```
cctgtaccTT cccacccag                                                    19
```

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
ctggatgctg gtggccctg                                                    19
```

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cctggatgct ggtggccct                                                19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cccagccact caggtgcct                                                19

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tcccttgtcc cagccactc                                                19

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gatcccttgt cccagccac                                                19

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
caagcaggtc cagctcccg                                                19

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50 ctcccctga agttgctgt                                                 19

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ttgtagtccg caccaccgt                                                19

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ggtgacctct gtgttccct                                              19

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gcctgcctct gcctccta                                              19

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gcccagcctg ttccttcag                                              19

<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggtagccctc agcctgaca                                              19

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ccatcattct ccctttct                                              19

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
attgcctgca tcccacggg                                              19

```
<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
cccacattgc ctgcatccc                                                 19

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ttcagtgctt gggcctttt                                                 19

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggctccctgt ttgactcca                                                 19

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gtatcaaggt ctccctcca                                                 19

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tcctttctcc ctgtcacag                                                 19

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
attctcaacc cgtcttcct                                                 19
```

```
<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tctgtttgct tcctcagct                                                    19

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gggtggcagt ctgaggtct                                                    19

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ggacagtggg tggcagtct                                                    19

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ttcccctcgc atcatcctt                                                    19

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tcccagacca cattggcct                                                    19

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tgcaccctgg agagcccat                                                    19

<210> SEQ ID NO 70
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gctggtggca ttcaagggt                                                19

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cgaaacctcc aggaagcct                                                19

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gatctcccag ggcatctga                                                19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gccttgctca gccacaatt                                                19

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
tatgtgcctt gctcagcca                                                19

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ctagccacaa ggacccagg                                                19

<210> SEQ ID NO 76
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
atgtacccca gggccaggt                                              19

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
atcccctcgg ttccacaca                                              19

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cccttgtcgc agtccccac                                              19

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gaagatgctg ctctggcct                                              19

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
cagtccctct gctttccac                                              19

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gcagagcaaa gcccacttc                                              19

<210> SEQ ID NO 82
<211> LENGTH: 19
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 82
cctgtggatt tggcagagc                                                  19

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ctccatgacc tttgccccca                                                 19

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84 cttttcttc cagtttgcc                                                   19

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cagctgctat ttccaccaa                                                  19

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gttgcctttc cagccagac                                                  19

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gctgggggtt gcctttcca                                                  19

<210> SEQ ID NO 88
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 88
cccttcatac accagaccg                                                       19

<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tgtcctccac cagcagtct                                                       19

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gcagatggta gctcctcag                                                       19

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tcctttggct gctggcttg                                                       19

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gcctccagtt cctttggct                                                       19

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
aatcagtgcc tccagttcc                                                       19

<210> SEQ ID NO 94
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 94
gtgctcttgt tgggttaca                                                19

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gcctcggcct cccaaagtg                                                19

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tagctgggac tacaggtgc                                                19

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tctcctgcct cagcctccc                                                19

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
acgccattct cctgcctca                                                19

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gctccgcctc ccaggttca                                                19

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 100
ggcacaatct tggctcact                                                19

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gctcctccag acccagtcc                                                19

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ggcctcccca gccctccaa                                                19

<210> SEQ ID NO 103
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ggagcaggtc ctccctcat                                                19

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
agctctttcc caggccctg                                                19

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cccctggtga aggtcaagg                                                19

<210> SEQ ID NO 106
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ggcatcccct ggtgaaggt                                                19

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gtctaggcga gggcatccc                                                19

<210> SEQ ID NO 108
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
ggcactcggt tctggccct                                                19

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gacacagccc caggtccca                                                19

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gctccagacc cagaacctt                                                19

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gggcagctcc accctagaa                                                19

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 112
gccactcttt ccagccacg                                                19

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gccagaccca cagcctcaa                                                19

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
caggtgtagg tcccagcct                                                19

<210> SEQ ID NO 115
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gcattgagct gctgtccct                                                19

<210> SEQ ID NO 116
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ggcctcctga atctccagc                                                19

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gcctctggcc ctcgtacag                                                19

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
```
ccagctcctc tatcttcct                                                19

<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ctgcctcggc tccaggtca                                                19

<210> SEQ ID NO 120
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gctgctgaga cctgctggc                                                19

<210> SEQ ID NO 121
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
aggtgtaggt cccagcctg                                                19

<210> SEQ ID NO 122
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gctccagctc ctctatctt                                                19

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gccatctctg taggtgagg                                                19

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124

```
gacagtggca ttgagctgc                                              19
```

<210> SEQ ID NO 125
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125

```
tctctgggcc ttcacccct                                              19
```

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126

```
ctgggcagat caggcagcc                                              19
```

<210> SEQ ID NO 127
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127

```
gggagggatg accagaggc                                              19
```

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128

```
gggaggtgga ggaaggggt                                              19
```

<210> SEQ ID NO 129
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129

```
ctgagcctcc cacatctct                                              19
```

<210> SEQ ID NO 130
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130

```
gcttcactgg agccaccca                                              19
```

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ggctgagatc ctggagggg                                                 19

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gctgccaagt gacccctgc                                                 19

<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ggacccacgc tcagcaccg                                                 19

<210> SEQ ID NO 134
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
ccatagcgag aagtccccg                                                 19

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tggcccaggc gcagacgga                                                 19

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ccatggggct gacttgggg                                                 19

<210> SEQ ID NO 137
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ttgagctgct gttcctgca                                                        19

<210> SEQ ID NO 138
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gcagcttccc cagggatcc                                                        19

<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gggatggggt gtccagaga                                                        19

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
tgggaaagga gctgggcct                                                        19

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
agaagcctct cccctggt                                                         19

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ggcacctggg ctagacagc                                                        19

<210> SEQ ID NO 143
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
ggttcttgct ccagctcct                    19

<210> SEQ ID NO 144
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 144
gctgagatct gctggctgc                    19

<210> SEQ ID NO 145
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 145
gctgctgaca gggagttta                    19

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 146
acgctcagca ccgtgtagc                    19

<210> SEQ ID NO 147
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 147
aggaggagtc cacttggca                    19

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 148
agtggcattg agctgctgt                    19

<210> SEQ ID NO 149

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
aatcccttgc cccagcaca                                              19

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gagatcgccc tttagctgg                                              19

<210> SEQ ID NO 151
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tgcagcagta ggtcccatg                                              19

<210> SEQ ID NO 152
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ggagtgacct tggctgctt                                              19

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
cccagcagag actcccact                                              19

<210> SEQ ID NO 154
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
catttgccaa ccctcctgg                                              19

<210> SEQ ID NO 155
<211> LENGTH: 19
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
gctggctgtt gacgtagca                                              19

<210> SEQ ID NO 156
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ttagcccttt attccccct                                              19

<210> SEQ ID NO 157
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
cctcctgcct aaggttccc                                              19

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
acttatcacc ctcctgcct                                              19

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gagcctcatc tccagcctc                                              19

<210> SEQ ID NO 160
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tcactgtccg agcctcatc                                              19

<210> SEQ ID NO 161
<211> LENGTH: 19
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 161
ctgactgcac gcaagcccc                                                   19

<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
gagcagagga caaccccca                                                   19

<210> SEQ ID NO 163
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ctgctctgcc atgctccca                                                   19

<210> SEQ ID NO 164
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gtcagttccc cttgagcac                                                   19

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ctgccttcgt atgtcccag                                                   19

<210> SEQ ID NO 166
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
cacagttgct ccccaatgc                                                   19

<210> SEQ ID NO 167
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
agccaggacc tccacagct                                                      19

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
gtctcccttc catacccac                                                      19

<210> SEQ ID NO 169
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ctgccaggtc tacagtcac                                                      19

<210> SEQ ID NO 170
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
cagcagcagc agcaggaca                                                      19

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ggcattctga ccgacctcc                                                      19

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tccctttcat cagtcctga                                                      19

<210> SEQ ID NO 173
<211> LENGTH: 19
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 173
gaggctcccc agtgtctgt                                                     19

<210> SEQ ID NO 174
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ggccaatcta gagtcccgt                                                     19

<210> SEQ ID NO 175
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gtgagggttg ctgcctgct                                                     19

<210> SEQ ID NO 176
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gcagtggaca gaacctcca                                                     19

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
cagtgcaggt cccagttca                                                     19

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gagctccaga gaccccacg                                                     19

<210> SEQ ID NO 179
<211> LENGTH: 19
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 179
gcccgaattt cctggagct                                                    19

<210> SEQ ID NO 180
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cagcacccag ttttccta                                                     19

<210> SEQ ID NO 181
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
gcccctttag actttctgt                                                    19

<210> SEQ ID NO 182
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tgccattgca ctccagcct                                                    19

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
atcccagcca ctcaggagg                                                    19

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
atgcctgtaa tcccagcca                                                    19

<210> SEQ ID NO 185
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 185
gctcacgcct gtaatccca                                                19

<210> SEQ ID NO 186
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ggctggatgt ggtggctca                                                19

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gccacatctc agccctgca                                                19

<210> SEQ ID NO 188
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gcctttgcct tctttccac                                                19

<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ggtcctcagg gagcagagt                                                19

<210> SEQ ID NO 190
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
aggccaagtc ctagaaggc                                                19

<210> SEQ ID NO 191
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 191
tgggtcacct gtatggctt                                              19

<210> SEQ ID NO 192
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
agtcacccgg acctcatca                                              19

<210> SEQ ID NO 193
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
gcccactgta ttcttctct                                              19

<210> SEQ ID NO 194
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gtcaacagct ctcagtcct                                              19

<210> SEQ ID NO 195
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gttgcccatg cccacaaag                                              19

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
tcccgttgcc catgcccac                                              19

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
```
ccccaagcta actgcgaca                                                19

<210> SEQ ID NO 198
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
tcacatagac ccctgttgt                                                19

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
cattctggct ctgttgggg                                                19

<210> SEQ ID NO 200
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ccttgacccc acaccataa                                                19

<210> SEQ ID NO 201
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
ctcttccttc accccttc                                                 19

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ctccccagcc aaacctccc                                                19

<210> SEQ ID NO 203
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
agctccccag ccaaacctc                                                   19

<210> SEQ ID NO 204
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
gacctcgagt ccaacctga                                                   19

<210> SEQ ID NO 205
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gccagttggt gcaggacct                                                   19

<210> SEQ ID NO 206
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
actccatcac catcggttt                                                   19

<210> SEQ ID NO 207
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
cccagtttac actccatca                                                   19

<210> SEQ ID NO 208
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
tcccatccta ccatctgct                                                   19

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gggagcggtg ttcaggtct                                                   19

<210> SEQ ID NO 210
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 210
aggagagtgc agggccagg                                               19

<210> SEQ ID NO 211
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 211
cggacctcag tggctttgc                                               19

<210> SEQ ID NO 212
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 212
ccatggccct cagtccttg                                               19

<210> SEQ ID NO 213
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 213
ccgttgccta tgcccaggt                                               19

<210> SEQ ID NO 214
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 214
gggttccgca tccaacttt                                               19

<210> SEQ ID NO 215
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 215
catcccagct ctgtctttc                                               19

<210> SEQ ID NO 216
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gcatccccat attaatccc                                                    19

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
ctccctgcct tttccttct                                                    19

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
acctttagca tcactggct                                                    19

<210> SEQ ID NO 219
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
agtgtcctga gctcctcca                                                    19

<210> SEQ ID NO 220
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ccttgtgttc tacctggtg                                                    19

<210> SEQ ID NO 221
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
cctcatccag tttccaagc                                                    19

```
<210> SEQ ID NO 222
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
ctcagcacaa ttccacgca                                                19

<210> SEQ ID NO 223
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
agccccaaag cacatgtca                                                19

<210> SEQ ID NO 224
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
atacctgtgg gtctcctgg                                                19

<210> SEQ ID NO 225
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
gccttcttct gtccatggc                                                19

<210> SEQ ID NO 226
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gcaccccatt ctgccacct                                                19

<210> SEQ ID NO 227
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
tcacatagac ccctgttgt                                                19

<210> SEQ ID NO 228
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ttgggctgtg ccattccct                                                       19

<210> SEQ ID NO 229
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
tgccccagag gaatgccca                                                       19

<210> SEQ ID NO 230
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gtggtatctc cccaaggac                                                       19

<210> SEQ ID NO 231
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
cagtccagga gaggcatcc                                                       19

<210> SEQ ID NO 232
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
ggagtcccaa gttcctgga                                                       19

<210> SEQ ID NO 233
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tccaacggtc cttctgggt                                                       19

<210> SEQ ID NO 234
<211> LENGTH: 19
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
gcctccattc cctgaacca                                                19

<210> SEQ ID NO 235
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ggattgtcct tccacccag                                                19

<210> SEQ ID NO 236
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
gctgcacttc ctccagagt                                                19

<210> SEQ ID NO 237
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
gcggcatgta gtccctcat                                                19

<210> SEQ ID NO 238
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ccaggaccag aggccagta                                                19

<210> SEQ ID NO 239
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239 gtaccccag tgcccctgt                                                 19

<210> SEQ ID NO 240
<211> LENGTH: 19
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 240
caccaggaca caggagggc                                                19

<210> SEQ ID NO 241
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
gctcccacgg gacctgact                                                19

<210> SEQ ID NO 242
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
tgaggaggtc atggctgca                                                19

<210> SEQ ID NO 243
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
gggacgaggg aggtaggga                                                19

<210> SEQ ID NO 244
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
gtttgaggcc catcagacc                                                19

<210> SEQ ID NO 245
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
gctcagtggc tcatccctg                                                19

<210> SEQ ID NO 246
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 246
ggctgtccca ggtcacaga                                                   19

<210> SEQ ID NO 247
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
ggtgacttcc aggtctgca                                                   19

<210> SEQ ID NO 248
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
cccgtgctgg tgacttcca                                                   19

<210> SEQ ID NO 249
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
ggtgtccatt gccttctgt                                                   19

<210> SEQ ID NO 250
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
gcctggtggg tgaagtgtc                                                   19

<210> SEQ ID NO 251
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
ttgtggtggc ctggtgggt                                                   19

<210> SEQ ID NO 252
<211> LENGTH: 19
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 252
attcggtctg tggggctcc                                               19

<210> SEQ ID NO 253
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
ctccttcctg ccagacata                                               19

<210> SEQ ID NO 254
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gccccaagtt cctggagac                                               19

<210> SEQ ID NO 255
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
cccaatttcc aggaatccg                                               19

<210> SEQ ID NO 256
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
ctccaggttc ccaatttcc                                               19

<210> SEQ ID NO 257
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tgcaggctct ctcccccag                                               19

<210> SEQ ID NO 258
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 258
ggcactgctt ctttctcta                                              19

<210> SEQ ID NO 259
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
agtcaccact ttccttgct                                              19

<210> SEQ ID NO 260
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ggtgctgagt ggatgtctt                                              19

<210> SEQ ID NO 261
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
cagcaagtgg tcctgtcca                                              19

<210> SEQ ID NO 262
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
ggcttcccat gctttgcct                                              19

<210> SEQ ID NO 263
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
tccacctgtg ccctgtct                                               19

<210> SEQ ID NO 264
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
actccaaggt cttatccct                                            19

<210> SEQ ID NO 265
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
tgatcccagg cagaaccct                                            19

<210> SEQ ID NO 266
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
gggctgagat ccttcctgg                                            19

<210> SEQ ID NO 267
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
tgggggttct gcatgagga                                            19

<210> SEQ ID NO 268
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
actcctctgg gggttctgc                                            19

<210> SEQ ID NO 269
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
agtaatgtat ccccaggca                                            19

<210> SEQ ID NO 270
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 270
aagagggctg gtctgggac                                               19

<210> SEQ ID NO 271
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gtagtgtttc ccttgtacc                                               19

<210> SEQ ID NO 272
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gccgtagtgt ttcccttgt                                               19

<210> SEQ ID NO 273
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
ctatagccgt agtgtttcc                                               19

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gtgaggaaca gaatccggg                                               19

<210> SEQ ID NO 275
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ttcctgcttc tggtttgtt                                               19

<210> SEQ ID NO 276
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
```
ccatttcctg cttctggtt                                                19

<210> SEQ ID NO 277
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gccatttcct gcttctggt                                                19

<210> SEQ ID NO 278
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ccatgctgga actctgtct                                                19

<210> SEQ ID NO 279
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ctgcacaggc tccatgctg                                                19

<210> SEQ ID NO 280
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
cctgcacagg ctccatgct                                                19

<210> SEQ ID NO 281
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ctgtgggatt gaaacctgc                                                19

<210> SEQ ID NO 282
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
ggtgttactg tgggattga                                                 19

<210> SEQ ID NO 283
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
gcagaaggtg ttactgtgg                                                 19

<210> SEQ ID NO 284
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
gtctgagcag gtggggtgc                                                 19

<210> SEQ ID NO 285
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
gcagtctgag caggtgggg                                                 19

<210> SEQ ID NO 286
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
tgtccaggta gccaggcct                                                 19

<210> SEQ ID NO 287
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
aatgtccagg tagccaggc                                                 19

<210> SEQ ID NO 288
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
gccctgtctt cacctgtgg                                                 19

<210> SEQ ID NO 289
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 289
tcctgctggc cctgtcttc                                              19

<210> SEQ ID NO 290
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 290
gtgccccatg gtgtctcct                                              19

<210> SEQ ID NO 291
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 291
tggcgtggca ggtatagga                                              19

<210> SEQ ID NO 292
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 292
gccccaggtg agaggccat                                              19

<210> SEQ ID NO 293
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 293
aaccagggcc actactcca                                              19

<210> SEQ ID NO 294
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 294
gccagggcta ctgctatca                                              19

<210> SEQ ID NO 295
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 295
ggtttcctac agactccca                    19

<210> SEQ ID NO 296
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 296
gttctggtcc ctctttccc                    19

<210> SEQ ID NO 297
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 297
ggtgcttaga ccctgatcc                    19

<210> SEQ ID NO 298
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 298
ctgccttgaa cagagccca                    19

<210> SEQ ID NO 299
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 299
aacccctccc tctcagcac                    19

<210> SEQ ID NO 300
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 300
gctggttccc tcctgaagc                    19

```
<210> SEQ ID NO 301
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
cctttcccaa gttcctagc                                                    19

<210> SEQ ID NO 302
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
gggcagctct ctgattcct                                                    19

<210> SEQ ID NO 303
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
gctcctgacc aagggacct                                                    19

<210> SEQ ID NO 304
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
agcagaggcc aaggtttcc                                                    19

<210> SEQ ID NO 305
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
ctcccacttc tcaaggacc                                                    19

<210> SEQ ID NO 306
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
tcacagcccc atttcccca                                                    19

<210> SEQ ID NO 307
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
gcacagtccg tgtcagggt                                                19

<210> SEQ ID NO 308
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
gtatgcagag tcccatgat                                                19

<210> SEQ ID NO 309
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
ccttgcaggg tgtggctat                                                19

<210> SEQ ID NO 310
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
ccttgtctgc tttctgcct                                                19

<210> SEQ ID NO 311
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
tgtgaccact ggggtaggt                                                19

<210> SEQ ID NO 312
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gaggttgggt gcctggtct                                                19

<210> SEQ ID NO 313
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
gccgctgtcc tgccgaggt                                               19

<210> SEQ ID NO 314
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
ggagggcagg gaacacagt                                               19

<210> SEQ ID NO 315
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
ctggttgttg cctggagaa                                               19

<210> SEQ ID NO 316
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
attggtccag ggcttgcag                                               19

<210> SEQ ID NO 317
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
ccaagctgtc actggctgg                                               19

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
gggtctccca gagcagtgt                                               19

<210> SEQ ID NO 319
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 319
agtcaaggga gccagcagg                                                    19

<210> SEQ ID NO 320
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
ggtttgggag tgttaggca                                                    19

<210> SEQ ID NO 321
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
ctcctggatc ggggtcctg                                                    19

<210> SEQ ID NO 322
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gccccataaa atccactcc                                                    19

<210> SEQ ID NO 323
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gggttgtccg tgccccata                                                    19

<210> SEQ ID NO 324
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
ggcaggcatc aggatatgg                                                    19

<210> SEQ ID NO 325
<211> LENGTH: 19
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 325
gcccagcacc tagaacggt                                                19

<210> SEQ ID NO 326
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
gcccagagcc agcccagca                                                19

<210> SEQ ID NO 327
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ttaggagcac caccaggca                                                19

<210> SEQ ID NO 328
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
cccaggagga gcagagccg                                                19

<210> SEQ ID NO 329
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
tgcagcggct caccatccc                                                19

<210> SEQ ID NO 330
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
agggcttgca cggcttgga                                                19

<210> SEQ ID NO 331
<211> LENGTH: 19
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 331
tcccacttct gaggttaca                                              19

<210> SEQ ID NO 332
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 332
gcttccgctc actcccact                                              19

<210> SEQ ID NO 333
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 333
agactgtgtc ctgtgtggc                                              19

<210> SEQ ID NO 334
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 334
gcggcagact gtgtcctgt                                              19

<210> SEQ ID NO 335
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 335
ggcacagtca actccaggc                                              19

<210> SEQ ID NO 336
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 336
agttggtcca gggcttgca                                              19

<210> SEQ ID NO 337
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 337
ggtgtgcttc ccagccaag                                                19

<210> SEQ ID NO 338
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
ccggagcagg tacagggcc                                                19

<210> SEQ ID NO 339
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gcagcctctg gtccctccg                                                19

<210> SEQ ID NO 340
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
ggcagcctct ggtccctcc                                                19

<210> SEQ ID NO 341
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
tgctcctctt ggatgggggg                                               19

<210> SEQ ID NO 342
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
ggcccaggtc agatcttgg                                                19

<210> SEQ ID NO 343
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
gttggcccag gagcgtggc					19

<210> SEQ ID NO 344
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gcaggaggta tgcatggca					19

<210> SEQ ID NO 345
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
gtttttattg tggtcccgc					19

<210> SEQ ID NO 346
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
gactcccgtc tgccaaggt					19

<210> SEQ ID NO 347
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
cccttcccct tccatctct					19

<210> SEQ ID NO 348
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
tccagattct catccaggg					19

<210> SEQ ID NO 349
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 349
ggccttgatc cgttttcca                                                19

<210> SEQ ID NO 350
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
accaccagcc ttagcgtct                                                19

<210> SEQ ID NO 351
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
tcccagagac caccagcct                                                19

<210> SEQ ID NO 352
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ccctgctccc ttgatccca                                                19

<210> SEQ ID NO 353
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
tggagggtcc tttgccgga                                                19

<210> SEQ ID NO 354
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
gttctgcacc tccatagtt                                                19

<210> SEQ ID NO 355
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
```
aggagccctt caggtagat                                              19

<210> SEQ ID NO 356
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
ccaaagaggc caccacagt                                              19

<210> SEQ ID NO 357
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
acaatcagct ccccatcat                                              19

<210> SEQ ID NO 358
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
cctgtgtccc gtccaccct                                              19

<210> SEQ ID NO 359
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
agggtaggct ctgcattca                                              19

<210> SEQ ID NO 360
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
gcaggctcaa ggcaatcct                                              19

<210> SEQ ID NO 361
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
tggacaccac cctttccat                                                    19

<210> SEQ ID NO 362
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
cccccatgag atgagagac                                                    19

<210> SEQ ID NO 363
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
aatcttcttt ccaagcccc                                                    19

<210> SEQ ID NO 364
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
agtcctgctt tccacgggg                                                    19

<210> SEQ ID NO 365
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
ggtgggtatc atagtccct                                                    19

<210> SEQ ID NO 366
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
ccttcttggc ctttatcct                                                    19

<210> SEQ ID NO 367
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
gggctcctca tccttctgg                                                    19

<210> SEQ ID NO 368
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
gttcatgctg gtgcctggt                                                19

<210> SEQ ID NO 369
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
gggagggcca ggatctgct                                                19

<210> SEQ ID NO 370
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
ccttcactcc ttgctcctc                                                19

<210> SEQ ID NO 371
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
gattcataac cccactcct                                                19

<210> SEQ ID NO 372
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
gttcatacca cctttggca                                                19

<210> SEQ ID NO 373
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
ggctctcttc aagtcctga                                                19

<210> SEQ ID NO 374
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 374
cacatcccca gacagttct					19

<210> SEQ ID NO 375
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 375
agcatcacat ccccagaca					19

<210> SEQ ID NO 376
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 376
gtccagttcc ctgctatcc					19

<210> SEQ ID NO 377
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 377
tgctttgcct gtctgtggc					19

<210> SEQ ID NO 378
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 378
gcatgtgttg ctttgcctg					19

<210> SEQ ID NO 379
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 379
attccattga agccctggc					19

```
<210> SEQ ID NO 380
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
cagccctcca cctttctgg                                                19

<210> SEQ ID NO 381
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
gtccacagta ggccctcca                                                19

<210> SEQ ID NO 382
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
cagtgcctgg tccacagta                                                19

<210> SEQ ID NO 383
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
agtatttagc ccagtgcct                                                19

<210> SEQ ID NO 384
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
cccaaagcga gtgagcacc                                                19

<210> SEQ ID NO 385
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
acatgggaag agcaggcca                                                19

<210> SEQ ID NO 386
```

<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 386
ggtggagtga ggctggtgc    19

<210> SEQ ID NO 387
<211> LENGTH: 1972
<212> TYPE: DNA
<213> ORGANISM: Mus musculus

<400> SEQUENCE: 387

```
tgagcagcgg ggaggaggaa gaggagactg ctactgaagg cgacactgcc aggggctctg      60
ggcatgtggg tccggcaggt accctggtca ttcacttggg ctgtgctgca gttgagctgg     120
caatcagggt ggcttctaga ggtccccaat gggccctgga ggtccctcac cttctaccca     180
gcctggctca cagtgtcaga gggagcaaat gccaccttca cctgcagctt gtccaactgg     240
tcggaggatc ttatgctgaa ctggaaccgc ctgagtccca gcaaccagac tgaaaaacag     300
gccgccttct gtaatggttt gagccaaccc gtccaggatg cccgcttcca gatcatacag     360
ctgcccaaca ggcatgactt ccacatgaac atccttgaca cacggcgcaa tgacagtggc     420
atctacctct gtggggccat ctccctgcac cccaaggcaa aaatcgagga gagccctgga     480
gcagagctcg tggtaacaga gagaatcctg gagacctcaa caagatatcc cagcccctcg     540
cccaaaccag aaggccggtt tcaaggcatg gtcattggta tcatgagtgc cctagtgggt     600
atccctgtat tgctgctgct ggcctgggcc tagctgtgtct tctgctcaac aagtatgtca     660
gaggccagag gagctggaag caaggacgac actctgaagg aggagccttc agcagcacct     720
gtccctagtg tggcctatga ggagctggac ttccagggac gagagaagac accagagctc     780
cctaccgcct gtgtgcacac agaatatgcc accattgtct tcactgaagg gctgggtgcc     840
tcggccatgg gacgtagggg ctcagctgat ggcctgcagg gtcctcggcc tccaagacat     900
gaggatggac attgttcttg gcctctttga ccagattctt cagccattag catgctgcag     960
accctccaca gagagcaccg gtccgtccct cagtcaagag gagcatgcag gctacagttc    1020
agccaaggct cccagggtct gagctagctg gagtgacagc ccagcgcctg caccaattcc    1080
agcacatgca ctgttgagtg agagctcact tcaggtttac cacaagctgg gagcagcagg    1140
cttcccggtt tcctattgtc acaaggtgca gagctgggc ctaagcctat gtctcctgaa    1200
tcctactgtt gggcacttct agggacttga gacactatag ccaatggcct ctgtgggttc    1260
tgtgcctgga aatggagaga tctgagtaca gcctgctttg aatggccctg tgaggcaacc    1320
ccaaagcaag ggggtccagg tatactatgg gcccagcacc taaagccacc cttgggagat    1380
gatactcagg tggaaaattc gtagactggg ggactgaacc aatcccaaga tctgaaaaag    1440
ttttgatgaa gacttgaaaa gctcctagct tcggggggtct gggaagcatg agcacttacc    1500
aggcaaaagc tccgtgagcg tatctgctgt ccttctgcat gcccaggtac ctcagttttt    1560
ttcaacagca aggaaactag ggcaataaag ggaaccagca gagctagagc cacccacaca    1620
tccaggggggc acttgactct ccctactcct cctaggaacc aaaaggacaa agtccatgtt    1680
gacagcaggg aaggaaaggg ggatataacc ttgacgcaaa ccaacactgg ggtgttagaa    1740
tctcctcatt cactctgtcc tggagttggg ttctggctct ccttcacacc taggactctg    1800
```

```
aaatgagcaa gcacttcaga cagtcagggt agcaagagtc tagctgtctg gtgggcaccc      1860
aaaatgacca gggcttaagt ccctttcctt tggtttaagc ccgttataat taaatggtac      1920
caaaagcttt aaaaaaaaaa aaaaaaaaa  aaaaaaaaaa aaaaaaaaa  aa              1972

<210> SEQ ID NO 388
<211> LENGTH: 2115
<212> TYPE: DNA
<213> ORGANISM: Homo sapiens

<400> SEQUENCE: 388 agtttcccctt ccgctcacct ccgcctgagc agtggagaag gcggcactct ggtggggctg      60
ctccaggcat gcagatccca caggcgccct ggccagtcgt ctgggcggtg ctacaactgg     120
gctggcggcc aggatggttc ttagactccc cagacaggcc ctggaacccc ccaccttct      180 ccccagccct gctcgtggtg accgaagggg acaacgccac cttcacctgc agcttctcca     240
acacatcgga gagcttcgtg ctaaaactggt accgcatgag ccccagcaac cagacggaca     300
agctggccgc cttccccgag gaccgcagcc agccccggcca ggactgccgc ttccgtgtca     360
cacaactgcc caacgggcgt gacttccaca tgagcgtggt cagggcccgg cgcaatgaca     420
gcggcaccta cctctgtggg gccatctccc tggcccccaa ggcgcagatc aaagagagcc     480
tgcgggcaga gctcagggtg acagagagaa gggcagaagt gcccacagcc accccagcc     540 cctcacccag gccagccggc cagttccaaa ccctggtggt tggtgtcgtg gcggcctgc     600 tgggcagcct ggtgctgcta gtctgggtcc tggccgtcat ctgctcccgg gccgcacgag     660
ggacaatagg agccaggcgc accggccagc ccctgaagga ggacccctca gccgtgcctg     720
tgttctctgt ggactatggg gagctggatt ccagtggcg agagaagacc ccggagcccc     780
ccgtgccctg tgtccctgag cagacggagt atgccaccat tgtctttcct agcggaatgg     840
gcacctcatc ccccgcccgc aggggctcag ctgacggccc tcggagtgcc cagccactga     900
ggcctgagga tggacactgc tcttggcccc tctgaccggc ttccttggcc accagtgttc     960
tgcagaccct ccaccatgag cccgggtcag cgcatttcct caggagaagc aggcagggtg    1020
caggccattg caggccgtcc aggggctgag ctgcctgggg cgaccgggg ctccagcctg     1080 cacctgcacc aggcacagcc ccaccacagg actcatgtct caatgcccac agtgagccca    1140
ggcagcaggt gtcaccgtcc cctacaggga gggccagatg cagtcactgc ttcaggtcct    1200
gccagcacag agctgcctgc gtccagctcc ctgaatctct gctgctgctg ctgctgctgc    1260
tgctgctgcc tgcggcccgg ggctgaaggc gccgtggccc tgcctgacgc cccggagcct    1320
cctgcctgaa cttgggggct ggttggagat ggccttggag cagccaaggt gcccctggca    1380
gtggcatccc gaaacgccct ggacgcaggg cccaagactg gcacaggag tgggaggtac     1440 atggggctgg ggactcccca ggagttatct gctccctgca ggcctagaga agtttcaggg    1500
aaggtcagaa gagctcctgg ctgtggtggg cagggcagga aaccccctcca cctttacaca    1560 tgcccaggca gcacctcagg ccctttgtgg ggcagggaag ctgaggcagt aagcgggcag    1620
gcagagctgg aggcctttca ggcccagcca gcactctggc ctcctgccgc cgcattccac    1680
cccagcccct cacaccactc gggagaggga catcctacgg tccaaggtc aggagggcag     1740 ggctggggtt gactcaggcc cctcccagct gtggccacct gggtgttggg agggcagaag    1800
tgcaggcacc tagggccccc catgtgccca ccctgggagc tctccttgga acccattcct    1860
gaaattattt aaaggggttg gccgggctcc caccagggcc tgggtgggaa ggtacaggcg    1920
ttcccccggg gcctagtacc cccgccgtgg cctatccact cctcacatcc acacactgca    1980
```

```
cccccactcc tggggcaggg ccaccagcat ccaggcggcc agcaggcacc tgagtggctg   2040
ggacaaggga tccccttcc ctgtggttct attatattat aattataatt aaatatgaga   2100
gcatgctaag gaaaa                                                    2115

<210> SEQ ID NO 389
<211> LENGTH: 3653
<212> TYPE: DNA
<213> ORGANISM: Mus musculus

<400> SEQUENCE: 389
gaaatcgtgg tccccaagcc tcatgccagg ctgcacttgc acgtcgcggg ccagtctcct     60
cgcctgcaga tagttcccaa acatgagga tatttgctgg cattatattc acagcctgct    120
gtcacttgct acgggcgttt actatcacgg ctccaaagga cttgtacgtg gtggagtatg    180
gcagcaacgt cacgatggag tgcagattcc ctgtagaacg ggagctggac ctgcttgcgt    240
tagtggtgta ctgggaaaag gaagatgagc aagtgattca gtttgtggca ggagaggagg    300
accttaagcc tcagcacagc aacttcaggg ggagagcctc gctgccaaag gaccagcttt    360
tgaagggaaa tgctgccctt cagatcacag acgtcaagct gcaggacgca ggcgtttact    420
gctgcataat cagctacggt ggtgcggact acaagcgaat cacgctgaaa gtcaatgccc    480
cataccgcaa aatcaaccag agaatttccg tggatccagc cacttctgag catgaactaa    540
tatgtcaggc cgagggttat ccagaagctg aggtaatctg acaaacagt gaccaccaac     600 ccgtgagtgg aagagaagt gtcaccactt cccggacaga ggggatgctt ctcaatgtga     660
ccagcagtct gagggtcaac gccacagcga atgatgtttt ctactgtacg ttttggagat    720
cacagccagg gcaaaaccac acagcggagc tgatcatccc agaactgcct gcaacacatc    780
ctccacagaa caggactcac tgggtgcttc tgggatccat cctgttgttc ctcattgtag    840
tgtccacggt cctcctcttc ttgagaaaac aagtgagaat gctagatgtg agaaatgtg     900 gcgttgaaga tacaagctca aaaaaccgaa atgatacaca attcgaggag acgtaagcag    960
tgttgaaccc tctgatcgtc gattggcagc ttgtggtctg tgaaagaaag ggcccatggg   1020
acatgagtcc aaagactcaa gatggaacct gagggagaga accaagaaag tgttgggaga   1080
ggagcctgga acaacggaca ttttttccag ggagacactg ctaagcaagt tgcccatcag   1140
tcgtcttggg aaatggattg agggttcctg gcttagcagc tggtccttgc acagtgacct   1200
tttcctctgc tcagtgccgg gatgagagat ggagtcatga gtgttgaaga ataagtgcct   1260
tctatttatt ttgagtctgt gtgttctcac tttgggcatg taattatgac tggtgaattc   1320
tgacgacatg atagatctta agatgtagtc accaaactca actgctgctt agcatcctcc   1380
gtaactactg atacaagcag ggaacacaga ggtcacctgc ttggtttgac aggctcttgc   1440
tgtctgactc aaataatctt tattttcag tcctcaaggc tcttcgatag cagttgttct     1500
gtatcagcct tataggtgtc aggtatagca ctcaacatct catctcatta caatagcaac   1560
cctcatcacc atagcaacag ctaacctctg ttatcctcac ttcatagcca ggaagctgag   1620
cgactaagtc acttgcccac agagtatcag ctctccagatt tctgttcttc agccactgtc   1680
ctttcaggat agaatttgtc gttaagaaat taatttaaaa actgattatt gagtagcatt   1740
gtatatcaat cacaacatgc cttgtgcact gtgctggcct ctgagcataa agatgtacgc   1800
cggagtaccg gtcggacatg tttatgtgtg ttaaatactc agagaaatgt tcattaacaa   1860
ggagcttgca ttttagagac actggaaagt aactccagtt cattgtctag cattacattt   1920
```

| | |
|---|---:|
| acctcatttg ctatccttgc catacagtct cttgttctcc atgaagtgtc atgaatcttg | 1980 |
| ttgaatagtt cttttatttt ttaaatgttt ctatttaaat gatattgaca tctgaggcga | 2040 |
| tagctcagtt ggtaaaaccc tttcctcaca agtgtgaaac cctgagtctt atccctagaa | 2100 |
| cccacataaa aaacagttgc gtatgttttgt gcatgctttt gatcccagca ctagggaggc | 2160 |
| agaggcaggc agatcctgag ctctcattga ccacccagcc tagcctacat ggttagctcc | 2220 |
| aggcctacag gagctggcag agcctgaaaa acgatgccta gacacacaca cacacacaca | 2280 |
| cacacacaca cacacacaca cacaccatgt actcatagac ctaagtgcac cctcctacac | 2340 |
| atgcacacac atacaattca aacacaaatc aacagggaat tgtctcagaa tggtccccaa | 2400 |
| gacaaagaag aagaaaaaca ccaaaccagc tctattccct cagcctatcc tctctactcc | 2460 |
| ttcctagaag caactactat tgttttttgta tataaattta cccaacgaca gttaatatgt | 2520 |
| agaatatata ttaaagtgtc tgtcaatata tattatctct ttctttcttt cttcctttct | 2580 |
| ttctttcttt ctttctttct ttctttcttt ctttctttct ttcttccttc ttccttcct | 2640 |
| tccttccttc cttccttcct ttctttcttt ctttcttttt ttctgtctat ctgtacctaa | 2700 |
| atggttgctc actatgcatt ttctgtgctc ttcgcccttt ttatttaatg tatggatatt | 2760 |
| tatgctgctt ccagaatgga tctaaagctc tttgttccta ggttttctcc cccatccttc | 2820 |
| taggcatctc tcacactgtc taggccagac accatgtctg ctgcctgaat ctgtagacac | 2880 |
| catttataaa gcacgtactc accgagtttg tatttggctt gttctgtgtc tgattaaagg | 2940 |
| gagaccatga gtccccaggg tacactgagt taccccagta ccaaggggga gccttgtttg | 3000 |
| tgtctccatg gcagaagcag gcctggagcc attttggttt cttccttgac ttctctcaaa | 3060 |
| cacagacgcc tcacttgctc attacaggtt ctcctttggg aatgtcagca ttgctccttg | 3120 |
| actgctggct gccctggaag gagcccatta gctctgtgtg agcccttgac agctactgcc | 3180 |
| tctccttacc acaggggcct ctaagatact gttacctaga ggtcttgagg atctgtgttc | 3240 |
| tctgggggga ggaaaggagg aggaacccag aactttctta cagttttcct tgttctgtca | 3300 |
| catgtcaaga ctgaaggaac aggctgggct acgtagtgag atcctgtctc aaaggaaaga | 3360 |
| cgagcatagc cgaaccccg gtggaacccc tctgttacc tgttcacaca gcttattga | 3420 |
| tgagtctcat gttaatgtct tgtttgtatg aagtttaaga aaatatcggg ttgggcaaca | 3480 |
| cattctattt attcatttta tttgaaatct taatgccatc tcatggtgtt ggattggtgt | 3540 |
| ggcactttat tcttttgtgt tgtgtataac cataaatttt attttgcatc agattgtcaa | 3600 |
| tgtattgcat taatttaata aatatttta tttattaaaa aaaaaaaaa aaa | 3653 |

<210> SEQ ID NO 390
<211> LENGTH: 3691
<212> TYPE: DNA
<213> ORGANISM: Homo sapiens

<400> SEQUENCE: 390

| | |
|---|---:|
| ggcgcaacgc tgagcagctg gcgcgtcccg cgcggcccca gttctgcgca gcttcccgag | 60 |
| gctccgcacc agccgcgctt ctgtccgcct gcagggcatt ccagaaagat gaggatattt | 120 |
| gctgtctttta tattcatgac ctactggcat ttgctgaacg catttactgt cacggttccc | 180 |
| aaggacctat atgtggtaga gtatggtagc aatatgacaa ttgaatgcaa attcccagta | 240 |
| gaaaaacaat tagacctggc tgcactaatt gtctattggg aaatggagga taagaacatt | 300 |
| attcaatttg tgcatggaga ggaagacctg aaggttcagc atagtagcta cagacagagg | 360 |
| gcccggctgt tgaaggacca gctctccctg ggaaatgctg cacttcagat cacagatgtg | 420 |

```
aaattgcagg atgcaggggt gtaccgctgc atgatcagct atggtggtgc cgactacaag    480
cgaattactg tgaaagtcaa tgccccatac aacaaaatca accaaagaat tttggttgtg    540
gatccagtca cctctgaaca tgaactgaca tgtcaggctg agggctaccc caaggccgaa    600
gtcatctgga caagcagtga ccatcaagtc ctgagtggta agaccaccac caccaattcc    660
aagagagagg agaagctttt caatgtgacc agcacactga gaatcaacac aacaactaat    720
gagattttct actgcacttt taggagatta gatcctgagg aaaaccatac agctgaattg    780
gtcatcccag aactacctct ggcacatcct ccaaatgaaa ggactcactt ggtaattctg    840
ggagccatct tattatgcct tggtgtagca ctgacattca tcttccgttt aagaaaaggg    900
agaatgatgg atgtgaaaaa atgtggcatc caagatacaa actcaaagaa gcaaagtgat    960
acacatttgg aggagacgta atccagcatt ggaacttctg atcttcaagc agggattctc   1020
aacctgtggt ttaggggttc atcggggctg agcgtgacaa gaggaaggaa tgggcccgtg   1080
ggatgcaggc aatgtgggac ttaaaaggcc caagcactga aatggaaacc tggcgaaagc   1140
agaggaggag aatgaagaaa gatggagtca acagggagc ctggagggag accttgatac   1200
tttcaaatgc ctgaggggct catcgacgcc tgtgacaggg agaaaggata cttctgaaca   1260
aggagcctcc aagcaaatca tccattgctc atcctaggaa gacgggttga gaatccctaa   1320 tttgaggggtc agttcctgca gaagtgccct tgcctccac tcaatgcctc aatttgtttt   1380
ctgcatgact gagagtctca gtgttggaac gggacagtat ttatgtatga gttttttccta   1440 tttatttttga gtctgtgagg tcttcttgtc atgtgagtgt ggttgtgaat gatttcttttt   1500 gaagatatat tgtagtagat gttacaattt tgtcgccaaa ctaaacttgc tgcttaatga   1560
tttgctcaca tctagtaaaa catggagtat ttgtaaggtg cttggtctcc tctataacta   1620
caagtataca ttggaagcat aaagatcaaa ccgttggttg cataggatgt caccttatt   1680 taacccatta atactctggt tgacctaatc ttattctcag acctcaagtg tctgtgcagt   1740
atctgttcca tttaaatatc agctttacaa ttatgtggta gcctacacac ataatctcat   1800
ttcatcgctg taaccaccct gttgtgataa ccactattat tttacccatc gtacagctga   1860
ggaagcaaac agattaagta acttgcccaa accagtaaat agcagacctc agactgccac   1920
ccactgtcct tttataatac aatttacagc tatattttac tttaagcaat tcttttattc   1980
aaaaaccatt tattaagtgc ccttgcaata tcaatcgctg tgccaggcat tgaatctaca   2040
gatgtgagca agacaaagta cctgtcctca aggagctcat agtataatga ggagattaac   2100
aagaaaatgt attattacaa tttagtccag tgtcatagca taaggatgat gcgaggggaa   2160
aacccgagca gtgttgccaa gaggaggaaa taggccaatg tggtctggga cggttggata   2220
tacttaaaca tcttaataat cagagtaatt ttcatttaca aagagaggtc ggtacttaaa   2280
ataaccctga aaaataacac tggaattcct tttctagcat tatatttatt cctgatttgc   2340
ctttgccata taatctaatg cttgtttata tagtgtctgg tattgtttaa cagttctgtc   2400
ttttctattt aaatgccact aaattttaaa ttcataccttt tccatgattc aaaattcaaa   2460
agatcccatg ggagatggtt ggaaaatctc cacttcatcc tccaagccat tcaagtttcc   2520
tttccagaag caactgctac tgcctttcat tcatatgttc ttctaaagat agtctacatt   2580
tggaaatgta tgttaaaagc acgtattttt aaaatttttt tcctaaatag taacacattg   2640
tatgtctgct gtgtactttg ctatttttat ttatttttagt gtttcttata tagcagatgg   2700
aatgaatttg aagttcccag ggctgaggat ccatgccttc tttgtttcta agttatcttt   2760
```

| | |
|---|---|
| cccatagctt tcattatct tcatatgat ccagtatatg ttaaatatgt cctacatata | 2820 |
| catttagaca accaccatt gttaagtatt tgctctagga cagagtttgg atttgtttat | 2880 |
| gtttgctcaa aaggagaccc atgggctctc cagggtgcac tgagtcaatc tagtcctaaa | 2940 |
| aagcaatctt attattaact ctgtatgaca gaatcatgtc tggaactttt gttttctgct | 3000 |
| ttctgtcaag tataaacttc actttgatgc tgtacttgca aaatcacatt ttctttctgg | 3060 |
| aaattccggc agtgtacctt gactgctagc taccctgtgc cagaaaagcc tcattcgttg | 3120 |
| tgcttgaacc cttgaatgcc accagctgtc atcactacac agccctccta agaggcttcc | 3180 |
| tggaggtttc gagattcaga tgccctggga gatcccagag tttcctttcc ctcttggcca | 3240 |
| tattctggtg tcaatgacaa ggagtacctt ggctttgcca catgtcaagg ctgaagaaac | 3300 |
| agtgtctcca acagagctcc ttgtgttatc tgtttgtaca tgtgcatttg tacagtaatt | 3360 |
| ggtgtgacag tgttctttgt gtgaattaca ggcaagaatt gtggctgagc aaggcacata | 3420 |
| gtctactcag tctattccta agtcctaact cctccttgtg gtgttggatt tgtaaggcac | 3480 |
| tttatccctt ttgtctcatg tttcatcgta aatggcatag gcagagatga tacctaattc | 3540 |
| tgcatttgat tgtcactttt tgtacctgca ttaatttaat aaaatattct tatttatttt | 3600 |
| gttacttggt acaccagcat gtccatttc ttgtttattt tgtgtttaat aaaatgttca | 3660 |
| gtttaacatc ccagtggaga aagttaaaaa a | 3691 |

<210> SEQ ID NO 391  
<211> LENGTH: 1506  
<212> TYPE: DNA  
<213> ORGANISM: Mus musculus

<400> SEQUENCE: 391

| | |
|---|---|
| ggagtagaca gcaatggcac tcagtaaaat atctcctaca gaaggttcta gaaggatcct | 60 |
| tgaagaccac cacatagatg aagatgtggg ctttgctcta ccacatccac tggtggagct | 120 |
| gcccgacgca tacagcccct gggtccttgt ggctagaaat ctgcctgtgc tgattgagaa | 180 |
| cgggcagctt cgagaagaag ttgaaaagct gcccacactg agcacggacg gactgagagg | 240 |
| acacaggtta cagcgcctgg cacacctggc cctggggtac atcaccatgg cgtatgtgtg | 300 |
| gaaccgaggg gatgacgatg ttcgaaaggt gctgccccgc aatattgctg ttccctactg | 360 |
| cgagctctca gagaagttgg gcctgcctcc tattctgtct tatgcagact gtgtcctggc | 420 |
| aaactggaag aaaaaggacc ccaatgggcc catgacatac gagaacatgg acattctgtt | 480 |
| ctcatttcct ggtggggact gcgacaaggg cttcttcctc gtctctctat tggtggaaat | 540 |
| cgcagcttct cctgcaatca aagcaatccc cactgtatcc agtgcagtag agcgtcaaga | 600 |
| cctgaaagca ttggaaaagg cactgcacga catagctacc agtctggaga agccaaggga | 660 |
| aattttaag aggatgcgtg actttgtgga cccagacacg ttttccacg ttctccgcat | 720 |
| atatctgtct ggctggaaat gcagctccaa gctgccagaa ggtctgctgt atgagggggt | 780 |
| ctgggacacc ccaaaaatgt tttcagggg cagtgcaggc cagagcagca tcttccagag | 840 |
| tcttgatgtc cttctgggaa taaaacacga ggctggcaaa gaatctcctg cagaattcct | 900 |
| ccaggaaatg agagagtaca tgcctccagc ccaccggaac ttccttttct tcttagagtc | 960 |
| agctccccca gtccgtgagt tgtcatttc aagacacaat gaagacttga cgaaagctta | 1020 |
| taacgagtgt gtgaatggtc tggtctctgt gagaaagttc cacctcgcaa tagtagatac | 1080 |
| ttacattatg aaaccttcga gaagaagcc cactgatggc gacaagtcgg aagagccctc | 1140 |
| aaatgtggaa agcagaggga ctgggggtac gaatcccatg actttcctaa ggagtgtgaa | 1200 |

```
agatacaacc gagaaagctc ttctgagttg gccttagtgt agcaagctcc acttctatca    1260
gggcacagaa aacaccttca tcctgtcata gctcattaaa tcagatccac caagtaagac    1320
tatagaataa tttgcctgtt gtatattatg tagatttcaa aaatcatctg tgcattccct    1380
gtaggaaaat aatcaagctg aactatttaa tgatattaaa atgatataag aaataatata    1440
aaatatattt atgattgaaa tacaacaatg agacccagta aataaaagtt attgtgaagt    1500
tgacta                                                                1506
```

<210> SEQ ID NO 392
<211> LENGTH: 1944
<212> TYPE: DNA
<213> ORGANISM: Homo sapiens

<400> SEQUENCE: 392

```
aatttctcac tgcccctgtg ataaactgtg gtcactggct gtggcagcaa ctattataag     60
atgctctgaa aactcttcag acactgaggg gcaccagagg agcagactac aagaatggca    120
cacgctatgg aaaactcctg acaatcagt aaagagtacc atattgatga agaagtgggc     180
tttgctctgc caaatccaca ggaaaatcta cctgattttt ataatgactg atgttcatt     240 gctaaacatc tgcctgatct catagagtct ggccagcttc gagaaagagt tgagaagtta    300
aacatgctca gcattgatca tctcacagac cacaagtcac agcgccttgc acgtctagtt    360
ctgggatgca tcaccatggc atatgtgtgg ggcaaaggtc atggagatgt ccgtaaggtc    420
ttgccaagaa atattgctgt tccttactgc caactctcca agaaactgga actgcctcct    480
attttggttt atgcagactg tgtcttggca aactggaaga aaaaggatcc taataagccc    540
ctgacttatg agaacatgga cgttttgttc tcatttcgtg atggagactg cagtaaagga    600
ttcttcctgg tctctctatt ggtggaaata gcagctgctt ctgcaatcaa agtaattcct    660
actgtattca aggcaatgca aatgcaagaa cgggacactt tgctaaaggc gctgttggaa    720
atagcttctt gcttggagaa agcccttcaa gtgtttcacc aaatccacga tcatgtgaac    780
ccaaaagcat ttttcagtgt tcttcgcata tatttgtctg gctggaaagg caaccccccag   840 ctatcagacg gtctggtgta tgaagggttc tgggaagacc caaggagtt tgcagggggc     900 agtgcaggcc aaagcagcgt cttttcagtgc tttgacgtcc tgctgggcat ccagcagact    960
gctggtggag acatgctgc tcagttcctc caggacatga agatatat gccaccagct     1020 cacaggaact tcctgtgctc attagagtca atccctcag tccgtgagtt tgtcctttca    1080
aaaggtgatg ctggcctgcg ggaagcttat gacgcctgtg tgaaagctct ggtctccctg    1140
aggagctacc atctgcaaat cgtgactaag tacatcctga ttcctgcaag ccagcagcca    1200
aaggagaata gacctctga agaccttca aaactggaag ccaaaggaac tggaggcact    1260
gatttaatga atttcctgaa gactgtaaga agtacaactg agaaatccct tttgaaggaa    1320
ggttaatgta acccaacaag agcacatttt atcatagcag agacatctgt atgcattcct    1380
gtcattaccc attgtaacag agccacaaac taatactatg caatgttta ccaataatgc     1440 aatacaaaag acctcaaaat acctgtgcat ttcttgtagg aaaacaacaa aaggtaatta    1500
tgtgtaatta tactagaagt tttgtaatct gtatcttatc attggaataa atgacattc    1560 aataaataaa aatgcataag atatattctg tcggctgggc gcggtggctc acgcctgtaa    1620
tcccagcact ttgggaggcc gaggcgggcg gatcacaagg tcaggagatc gagaccatct    1680
tggctaacac ggtgaaaccc cgtctctact aaaaatacaa aaattagcc gggcgcggtg    1740
```

```
gcgggcacct gtagtcccag ctactcggga ggctgaggca ggagaatggc gtgaacctgg    1800
gaggcggagc ttgcagtgag ccaagattgt gccactgcaa tccggcctgg gctaaagagc    1860
gggactccgt ctcaaaaaaa aaaaaaaaaa gatatattct gtcataataa ataaaaatgc    1920
ataagatata aaaaaaaaaa aaaa                                           1944

<210> SEQ ID NO 393
<211> LENGTH: 2020
<212> TYPE: DNA
<213> ORGANISM: Mus musculus

<400> SEQUENCE: 393
gggcagtggg gaggagaagc agaaggactg ggtctggagg agcagctcaa gttctagcta     60
gctgcagtgg gtttgcctgc actctgctct gggtcccagc ccgggcctct gatcattatc    120
catcctgctg tctccagtcc ccactcctgg ggcgtcctct tcaccctaca ttctttccct    180
ccgcctcacc tcctccttgt agaacttctc tctctctctc tctctctctc tctctctctc    240
tctctctctc tctgtgtgtg tgtgtgtgtc tgtctgtctg tctgtctctc tctcctccca    300
ggacctttt ctaacctccc ttggagggct ggggaggccc gggccataga ggagatgagg     360
gaggacctgc tccttggctt tttgcttctg ggactgcttt gggaagctcc agttgtgtct    420
tcagggcctg ggaaagagct ccccgtggtg tgggcccagg agggagctcc cgtccatctt    480
ccctgcagcc tcaaatcccc caacctggat cctaactttc tacgaagagg aggggttatc    540
tggcaacatc aaccagacag tggccaaccc actcccatcc cggcccttga ccttcaccag    600
gggatgccct cgcctagaca acccgcaccc ggtcgctaca cggtgctgag cgtggctcca    660
ggaggcctgc gcagcgggag gcagcccctg catccccacg tgcagctgga ggagcgcggc    720
ctccagcgcg gggacttctc tctgtggttg cgcccagctc tgcgcaccga tgcgggcgag    780
taccacgcca ccgtgcgcct cccgaaccgc gccctctcct gcagtctccg cctgcgcgtc    840
ggccaggcct cgatgattgc tagtccctca ggagtcctca agctgtctga ttgggtcctt    900
ttgaactgct ccttcagccg tcctgaccgc ccagtctctg tgcactggtt ccagggccag    960
aaccgagtgc ctgtctacaa ctcaccgcgt catttttag ctgaaacttt cctgttactg    1020
ccccaagtca gcccctggaa ctctgggacc tggggctgtg tcctcaccta cagagatggc    1080
ttcaatgtct ccatcacgta caacctcaag gttctgggtc tggagcccgt agcccctctg    1140
acagtgtacg ctgctgaagg ttctagggtg gagctgccct gtcatttgcc cccaggagtg    1200
gggaccccctt ctttgctcat tgccaagtgg actcctcctg gaggaggtcc tgagctcccc    1260
gtggctggaa agagtggcaa ttttacccct caccttgagg ctgtgggtct ggcacaggct    1320
gggacctaca cctgtagcat ccatctgcag ggacagcagc tcaatgccac tgtcacgttg    1380
gcggtcatca cagtgactcc caaatccttc gggttacctg gctcccgggg gaagctgttg    1440
tgtgaggtaa ccccggcatc tggaaaggaa agatttgtgt ggcgtcccct gaacaatctg    1500
tccaggagtt gccggggccc tgtgctggag attcaggagg ccaggctcct tgctgagcga    1560
tggcagtgtc agctgtacga gggccagagg cttcttggag cgacagtgta cgccgcagag    1620
tctagctcag gcgcccacag tgctaggaga atctcaggtg accttaaagg aggccatctc    1680
gttctcgttc tcatccttgg tgccctctcc ctgttccttt tggtggccgg ggcctttggc    1740
tttcactggt ggagaaaaca gttgctactg agaagatttt ctgccttaga acatgggatt    1800
cagccatttc cggctcagag gaagatagag gagctggagc gagaactgga gacggagatg    1860
ggacaggagc cggagcccga gccggagcca cagctggagc cagagcccag gcagctctga    1920
```

| | |
|---|---|
| cctggagccg aggcagccag caggtctcag cagctccgcc cgcccgcccg cccgcccgaa | 1980 |
| taaactccct gtcagcagca tcaaaaaaaa aaaaaaaaaa | 2020 |

<210> SEQ ID NO 394
<211> LENGTH: 1995
<212> TYPE: DNA
<213> ORGANISM: Homo sapiens

<400> SEQUENCE: 394

| | |
|---|---|
| acagggtga aggcccagag accagcagaa cggcatccca gccacgacgg ccactttgct | 60 |
| ctgtctgctc tccgccacgg ccctgctctg ttccctggga cacccccgcc cccacctcct | 120 |
| caggctgcct gatctgccca gcttccagc tttcctctgg attccggcct ctggtcatcc | 180 |
| ctccccaccc tctctccaag gccctctcct ggtctccctt cttctagaac cccttcctcc | 240 |
| acctccctct ctgcagaact tctccttttac cccccacccc ccaccactgc cccctttcct | 300 |
| tttctgacct ccttttggag ggctcagcgc tgcccagacc ataggagaga tgtgggaggc | 360 |
| tcagttcctg ggcttgctgt ttctgcagcc gctttgggtg gctccagtga agcctctcca | 420 |
| gccaggggct gaggtcccgg tggtgtgggc ccaggagggg gctcctgccc agctcccctg | 480 |
| cagccccaca atcccctcc aggatctcag ccttctgcga agagcagggg tcacttggca | 540 |
| gcatcagcca gacagtggcc cgccgctgc cgccccggc catccctgg ccccggccc | 600 |
| tcacccggcg gcgccctcct cctggggcc caggccccgc cgctacacgg tgctgagcgt | 660 |
| gggtcccgga ggcctgcgca gcggaggct gcccctgcag cccgcgtcc agctggatga | 720 |
| gcgcggccgg cagcgcgggg acttctcgct atggctgcgc ccagcccggc gcgcggacgc | 780 |
| cggcgagtac cgcgccgcgg tgcacctcag ggaccgcgcc ctctcctgcc gcctccgtct | 840 |
| gcgcctgggc caggcctcga tgactgccag cccccagga tctctcagag cctccgactg | 900 |
| ggtcattttg aactgctcct tcagccgccc tgaccgccca gcctctgtgc attggttccg | 960 |
| gaaccggggc cagggccgag tccctgtccg ggagtccccc catcaccact tagcggaaag | 1020 |
| cttcctcttc ctgccccaag tcagcccat ggactctggg ccctggggct gcatcctcac | 1080 |
| ctacagagat ggcttcaacg tctccatcat gtataacctc actgttctgg gtctggagcc | 1140 |
| cccaactccc ttgacagtgt acgctggagc aggttccagg gtggggctgc cctgccgcct | 1200 |
| gcctgctggt gtggggaccc ggtctttcct cactgccaag tggactcctc ctgggggagg | 1260 |
| ccctgacctc ctggtgactg gagacaatgg cgactttacc cttcgactag aggatgtgag | 1320 |
| ccaggcccag gctgggacct acacctgcca tatccatctg caggaacagc agctcaatgc | 1380 |
| cactgtcaca ttggcaatca tcacagtgac tcccaaatcc tttgggtcac ctggatccct | 1440 |
| ggggaagctg ctttgtgagg tgactccagt atctggacaa gaacgctttg tgtgagctc | 1500 |
| tctggacacc ccatcccaga ggagtttctc aggaccttgg ctggaggcac aggaggccca | 1560 |
| gctcctttcc cagccttggc aatgccagct gtaccagggg gagaggcttc ttggagcagc | 1620 |
| agtgtacttc acagagctgt ctagcccagg tgcccaacgc tctgggagag cccaggtgc | 1680 |
| cctcccagca ggccacctcc tgctgttttct catccttggt gtcctttctc tgctcctttt | 1740 |
| ggtgactgga gcctttggct ttcacctttg gagaagacag tggcgaccaa gacgattttc | 1800 |
| tgccttagag caaggggattc accctccgca ggctcagagc aagatagagg agctggagca | 1860 |
| agaaccggag ccggagccgg agccggaacc ggagcccgag cccgagcccg agccggagca | 1920 |
| gctctgacct ggagctgagg cagccagcag atctcagcag cccagtccaa ataaactccc | 1980 |

-continued

```
tgtcagcagc aaaaa                                              1995

<210> SEQ ID NO 395
<211> LENGTH: 2725
<212> TYPE: DNA
<213> ORGANISM: Mus musculus

<400> SEQUENCE: 395
accattttaa ccgaggagct aaagctatcc ctacacagag ctgtccttgg atttcccctg    60
ccaagtactc atgttttcag gtcttaccct caactgtgtc ctgctgctgc tgcaactact   120
acttgcaagg tcattggaaa atgcttatgt gtttgaggtt ggtaagaatg cctatctgcc   180
ctgcagttac actctatcta cacctggggc acttgtgcct atgtgctggg gcaagggatt   240
ctgtccttgg tcacagtgta ccaacgagtt gctcagaact gatgaaagaa atgtgacata   300
tcagaaatcc agcagatacc agctaaaggg cgatctcaac aaaggagacg tgtctctgat   360
cataaagaat gtgactctgg atgaccatgg gacctactgc tgcaggatac agttccctgg   420
tcttatgaat gataaaaaat tagaactgaa attagacatc aaagcagcca aggtcactcc   480
agctcagact gcccatgggg actctactac agcttctcca agaaccctaa ccacggagag   540
aaatggttca gagacacaga cactggtgac cctccataat aacaatggaa caaaaatttc   600
cacatgggct gatgaaatta aggactctgg agaaacgatc agaactgcta tccacattgg   660
agtgggagtc tctgctgggt tgaccctggc acttatcatt ggtgtcttaa tccttaaatg   720
gtattcctgt aagaaaaaga agttatcgag tttgagcctt attacactgg ccaacttgcc   780
tccaggaggg ttggcaaatg caggagcagt caggattcgc tctgaggaaa atatctacac   840
catcgaggag aacgtatatg aagtggagaa ttcaaatgag tactactgct acgtcaacag   900
ccagcagcca tcctgaccgc ctctggactg ccacttttaa aggctcgcct tcatttctga   960
ctttggtatt tccctttttg aaaactatgt gatatgtcac ttggcaacct cattggaggt  1020
tctgaccaca gccactgaga aaagagttcc agttttctgg ggataattaa ctcacaaggg  1080
gattcgactg taactcatgc tacattgaaa tgctccattt tatccctgag tttcagggat  1140
cggatctccc actccagaga cttcaatcat gcgtgttgaa gctcactcgt gctttcatac  1200
attaggaatg gttagtgtga tgtctttgag acatagaggt ttgtggtata tctgcaaagc  1260
tcctgaacag gtaggggaa taaagggcta agataggaag gtgaggttct ttgttgatgt   1320
tgaaaatcta agaagttgg tagcttttct agagatttct gaccttgaaa gattaagaaa   1380
aagccaggtg gcatatgctt aacactatat aacttgggaa ccttaggcag gagggtgata  1440
agttcaaggt cagccagggc tatgctggta agactgtctc aaaatccaaa gacgaaaata  1500
aacatagaga cagcaggagg ctggagatga ggctcggaca gtgaggtgca ttttgtacaa  1560
gcacgaggaa tctatatttg atcgtagacc ccacatgaaa aagctaggcc tggtagagca  1620
tgcttgtaga ctcaagagat ggagaggtaa aggcacaaca gatccccggg gcttgcgtgc  1680
agtcagctta gcctaggtgc tgagttccaa gtccacaaga gtccctgtct caaagtaaga  1740
tggactgagt atctggcgaa tgtccatggg ggttgtcctc tgctctcaga agagacatgc  1800
acatgaacct gcacacacac acacacacac acacacacac acacacacac acacacacac  1860
acacacatga aatgaaggtt ctctctgtgc ctgctacctc tctataacat gtatctctac  1920
aggactctcc tctgcctctg ttaagacatg agtgggagca tggcagagca gtccagtaat  1980
taattccagc actcagaagg ctggagcaga agcgtggaga gttcaggagc actgtgccca  2040
acactgccag actcttctta cagaagaaaa aggttacccg caagcagcct gctgtctgta  2100
```

| | |
|---|---|
| aaaggaaacc ctgcgaaagg caaactttga ctgttgtgtg ctcaaggga actgactcag | 2160 |
| acaacttctc cattcctgga ggaaactgga gctgtttctg acagaagaac aaccggtgac | 2220 |
| tgggacatac gaaggcagag ctcttgcagc aatctatata gtcagcaaaa tattctttgg | 2280 |
| gaggacagtc gtcaccaaat tgattttcaa gccggtggac ctcagtttca tctggcttac | 2340 |
| agctgcctgc ccagtgccct tgatctgtgc tggctcccat ctataacaga atcaaattaa | 2400 |
| atagaccccg agtgaaaata ttaagtgagc agaaaggtag ctttgttcaa agatttttt | 2460 |
| gcattgggga gcaactgtgt acatcagagg acatctgtta gtgaggacac caaaacctgt | 2520 |
| ggtaccgttt tttcatgtat gaattttgtt gtttaggttg cttctagcta gctgtggagg | 2580 |
| tcctggcttt cttaggtggg tatggaaggg agaccatcta acaaaatcca ttagagataa | 2640 |
| cagctctcat gcagaaggga aaactaatct caaatgtttt aaagtaataa aactgtactg | 2700 |
| gcaaagtact ttgagcatat ttaaa | 2725 |

<210> SEQ ID NO 396
<211> LENGTH: 2448
<212> TYPE: DNA
<213> ORGANISM: Homo sapiens

<400> SEQUENCE: 396

| | |
|---|---|
| agaacactta caggatgtgt gtagtgtggc atgacagaga actttggttt cctttaatgt | 60 |
| gactgtagac ctggcagtgt tactataaga atcactggca atcagacacc cgggtgtgct | 120 |
| gagctagcac tcagtggggg cggctactgc tcatgtgatt gtggagtaga cagttggaag | 180 |
| aagtacccag tccatttgga gagttaaaac tgtgcctaac agaggtgtcc tctgactttt | 240 |
| cttctgcaag ctccatgttt tcacatcttc cctttgactg tgtcctgctg ctgctgctgc | 300 |
| tactacttac aaggtcctca gaagtggaat acagagcgga ggtcggtcag aatgcctatc | 360 |
| tgccctgctt ctacaccca gccgcccag ggaacctcgt gcccgtctgc tggggcaaag | 420 |
| gagcctgtcc tgtgtttgaa tgtggcaacg tggtgctcag gactgatgaa agggatgtga | 480 |
| attattggac atccagatac tggctaaatg gggatttccg caaggagat gtgtccctga | 540 |
| ccatagagaa tgtgactcta gcagacagtg ggatctactg ctgccggatc caaatcccag | 600 |
| gcataatgaa tgatgaaaaa tttaacctga gttggtcat caaaccagcc aaggtcaccc | 660 |
| ctgcaccgac tcggcagaga gacttcactg cagccttcc aaggatgctt accaccaggg | 720 |
| gacatggccc agcagagaca cagacactgg ggagcctccc tgatataaat ctaacacaaa | 780 |
| tatccacatt ggccaatgag ttacgggact ctagattggc caatgactta cgggactctg | 840 |
| gagcaaccat cagaataggc atctacatcg agcagggat ctgtgctggg ctggctctgg | 900 |
| ctcttatctt cggcgcttta atttcaaat ggtattctca tagcaaagag aagatacaga | 960 |
| atttaagcct catctctttg gccaacctcc ctccctcagg attggcaaat gcagtagcag | 1020 |
| agggaattcg ctcagaagaa acatctata ccattgaaga gaacgtatat gaagtggagg | 1080 |
| agcccaatga gtattattgc tatgtcagca gcaggcagca accctcacaa cctttgggtt | 1140 |
| gtcgctttgc aatgccatag atccaaccac cttatttttg agcttggtgt tttgtctttt | 1200 |
| tcagaaacta tgagctgtgt cacctgactg gttttggagg ttctgtccac tgctatggag | 1260 |
| cagagttttc ccattttcag aagataatga ctcacatggg aattgaactg ggacctgcac | 1320 |
| tgaacttaaa caggcatgtc attgcctctg tatttaagcc aacagagtta cccaacccag | 1380 |
| agactgttaa tcatggatgt tagagctcaa acgggctttt atatacacta ggaattcttg | 1440 |

```
acgtggggtc tctggagctc caggaaattc gggcacatca tatgtccatg aaacttcaga    1500
taaactaggg aaaactgggt gctgaggtga aagcataact tttttggcac agaaagtcta    1560
aaggggccac tgattttcaa agagatctgt gatccctttt tgttttttgt ttttgagatg    1620
gagtcttgct ctgttgccca ggctggagtg caatggcaca atctcggctc actgcaagct    1680
ccgcctcctg ggttcaagcg attctcctgc ctcagcctcc tgagtggctg ggattacagg    1740
catgcaccac catgcccagc taatttgttg tattttagt agagacaggg tttcaccatg      1800
ttggccagtg tggtctcaaa ctcctgacct catgatttgc ctgcctcggc ctcccaaagc    1860
actgggatta caggcgtgag ccaccacatc cagccagtga tccttaaaag attaagagat    1920
gactggacca ggtctacctt gatcttgaag attcccttgg aatgttgaga tttaggctta    1980
tttgagcact gcctgcccaa ctgtcagtgc cagtgcatag cccttctttt gtctccctta    2040
tgaagactgc cctgcagggc tgagatgtgg caggagctcc cagggaaaaa cgaagtgcat    2100
ttgattggtg tgtattggcc aagttttgct tgttgtgtgc ttgaaagaaa atatctctga    2160
ccaacttctg tattcgtgga ccaaactgaa gctatatttt tcacagaaga agaagcagtg    2220
acggggacac aaaattctgtt gcctggtgga aagaaggcaa aggccttcag caatctatat    2280
taccagcgct ggatccttg acagagagtg gtccctaaac ttaaatttca agacggtata    2340
ggcttgatct gtcttgctta ttgttgcccc ctgcgcctag cacaattctg acacacaatt    2400
ggaacttact aaaaattttt ttttactgtt aaaaaaaaa aaaaaaaa                  2448

<210> SEQ ID NO 397
<211> LENGTH: 1933
<212> TYPE: DNA
<213> ORGANISM: Mus musculus

<400> SEQUENCE: 397
ctacacatat gtagcacgta ccttggatca aagctgtcta tataaagtcc ccgagtctgt      60
gtgggttcaa acacatctca aggcttctgg atcctgttgg gttttactct gctccctgag     120
gacctcagca catttgcccc ccagccatgg cttgtcttgg actccggagg tacaaagctc     180
aactgcagct gccttctagg acttggcctt ttgtagccct gctcactctt cttttcatcc     240
cagtcttctc tgaagccata caggtgaccc aaccttcagt ggtgttggct agcagccatg     300
gtgtcgccag cttccatgt gaatattcac catcacacaa cactgatgag gtccgggtga      360
ctgtgctgcg gcagacaaat gaccaaatga ctgaggtctg tgccacgaca ttcacagaga     420
agaatacagt gggcttccta gattacccct tctgcagtgg tacctttaat gaaagcagag     480
tgaacctcac catccaagga ctgagagctg ttgacacggg actgtacctc tgcaaggtgg     540
aactcatgta cccaccgcca tactttgtgg gcatgggcaa cgggacgcag atttatgtca     600
ttgatccaga accatgcccg gattctgact tcctcctttg gatccttgtc gcagttagct     660
tggggttgtt ttttttacagt ttcctggtca ctgctgtttc tttgagcaag atgctaaaga    720
aaagaagtcc tcttacaaca ggggtctatg tgaaaatgcc cccaacagag ccagaatgtg     780
aaaagcaatt tcagccttat tttattccca tcaactgaaa ggccgtttat gaagaagaag     840
gagcatactt cagtctctaa aagctgaggc aatttcaact ttcctttct ctccagctat      900 tttttacctgt ttgtatattt taaggagagt atgcctctct ttaatagaaa gctggatgca    960
aaattccaat taagcatact acaatttaaa gctaaggagc atgaacagag agctgggata   1020
tttctgttgt gtcagaacca ttttactaaa agcatcactt ggaagcagca taaggatata   1080
gcattatggt gtggggtcaa gggaacatta gggaatggca cagcccaaag aaaggaaggg   1140
```

```
ggtgaaggaa gagattatat tgtacacatc ttgtatttac ctgagagatg tttatgactt    1200
aaataatttt taaattttc atgctgttat tttctttaac aatgtataat tacacgaagg    1260
tttaaacatt tattcacaga gctatgtgac atagccagtg gttccaaagg ttgtagtgtt    1320
ccaagatgta tttttaagta atattgtaca tgggtgtttc atgtgctgtt gtgtatttgc    1380
tggtggtttg aatataaaca ctatgtatca gtgtcgtccc acagtgggtc ctggggaggt    1440
ttggctgggg agcttaggac actaatccat caggttggac tcgaggtcct gcaccaactg    1500
gcttggaaac tagatgaggc tgtcacaggg ctcagttgca taaaccgatg gtgatggagt    1560
gtaaactggg tctttacact cattttattt tttgtttctg cttttgtttt cttcaatgat    1620
ttgcaaggaa accaaaagct ggcagtgttt gtatgaacct gacagaacac tgtcttcaag    1680
gaaatgcctc attcctgaga ccagtaggtt tgttttttta ggaagttcca atactaggac    1740
cccctacaag tactatggct cctcgaaaac acaaagttaa tgccacagga agcagcagat    1800
ggtaggatgg gatgcacaag agttcctgaa aactaacact gttagtgttt ttttttttaac    1860 tcaatatttt ccatgaaaat gcaaccacat gtataatatt tttaattaaa taaaagtttc    1920
ttgtgattgt ttt                                                      1933

<210> SEQ ID NO 398
<211> LENGTH: 2033
<212> TYPE: DNA
<213> ORGANISM: Homo sapiens

<400> SEQUENCE: 398
cttctgtgtg tgcacatgtg taatacatat ctgggatcaa agctatctat ataaagtcct     60
tgattctgtg tgggttcaaa cacatttcaa agcttcagga tcctgaaagg ttttgctcta    120
cttcctgaag acctgaacac cgctcccata aagccatggc ttgccttgga tttcagcggc    180
acaaggctca gctgaacctg gctaccagga cctggccctg cactctcctg ttttttcttc    240
tcttcatccc tgtcttctgc aaagcaatgc acgtggccca gcctgctgtg gtactggcca    300
gcagccgagg catcgccagc tttgtgtgtg agtatgcatc tccaggcaaa gccactgagg    360
tccgggtgac agtgcttcgg caggctgaca gccaggtgac tgaagtctgt gcggcaacct    420
acatgatggg gaatgagttg accttcctag atgattccat ctgcacgggc acctccagtg    480
gaaatcaagt gaacctcact atccaaggac tgagggccca ggcacgggga ctctacatct    540
gcaaggtgga gctcatgtac ccaccgccat actacctggg cataggcaac ggaacccaga    600
tttatgtaat tgatccagaa ccgtgcccag attctgactt cctcctctgg atccttgcag    660
cagttagttc ggggttgttt tttatagct ttctcctcac agctgtttct ttgagcaaaa    720
tgctaaagaa aagaagccct cttacaacag gggtctatgt gaaaatgccc ccaacagagc    780
cagaatgtga aaagcaattt cagccttatt ttattcccat caattgagaa accattatga    840
agaagagagt ccatatttca atttccaaga gctgaggcaa ttctaacttt tttgctatcc    900 agctatttt atttgtttgt gcatttgggg ggaattcatc tctctttaat ataaagttgg    960
atgcggaacc caaattacgt gtactacaat ttaaagcaaa ggagtagaaa gacagagctg   1020
ggatgtttct gtcacatcag ctccactttc agtgaaagca tcacttggga ttaatatggg   1080
gatgcagcat tatgatgtgg gtcaaggaat taagttaggg aatggcacag cccaaagaag   1140
gaaaaggcag ggagcgaggg agaagactat attgtacaca ccttatattt acgtatgaga   1200
cgtttatagc cgaaatgatc ttttcaagtt aaattttatg ccttttattt cttaaacaaa   1260
```

-continued

| | |
|---|---|
| tgtatgatta catcaaggct tcaaaaatac tcacatggct atgttttagc cagtgatgct | 1320 |
| aaaggttgta ttgcatatat acatatatat atatatatat atatatatat atatatatat | 1380 |
| atatatatat atatatattt taatttgata gtattgtgca tagagccacg tatgtttttg | 1440 |
| tgtatttgtt aatggtttga atataaacac tatatggcag tgtctttcca ccttgggtcc | 1500 |
| cagggaagtt ttgtggagga gctcaggaca ctaatacacc aggtagaaca caaggtcatt | 1560 |
| tgctaactag cttggaaact ggatgaggtc atagcagtgc ttgattgcgt ggaattgtgc | 1620 |
| tgagttggtg ttgacatgtg ctttggggct tttacaccag ttcctttcaa tggtttgcaa | 1680 |
| ggaagccaca gctggtggta tctgagttga cttgacagaa cactgtcttg aagacaatgg | 1740 |
| cttactccag agacccaca ggtatgacct tctaggaagc tccagttcga tgggcccaat | 1800 |
| tcttacaaac atgtggttaa tgccatggac agaagaaggc agcaggtggc agaatggggt | 1860 |
| gcatgaaggt ttctgaaaat taacactgct tgtgttttta actcaatatt ttccatgaaa | 1920 |
| atgcaacaac atgtataata tttttaatta aataaaaatc tgtggtggtc gttttaaaaa | 1980 |
| aaaaaaaaaa aaaaaaaaaa aaaaaaaaaa aaaaaaaaaa aaaaaaaaaa aaa | 2033 |

<210> SEQ ID NO 399
<211> LENGTH: 3014
<212> TYPE: DNA
<213> ORGANISM: Mus musculus

<400> SEQUENCE: 399

| | |
|---|---|
| cgcacaagta caaccacaca gaagacacag ctggaaagct ccctggcctg ggcattcctc | 60 |
| tggggcagag acctcacgcg aaaatatgga gcctcaaagt cagagcatga cgctggaggt | 120 |
| gccgttgtcc ttggggagat accacatttc tgaggaatat ggctttctcc ttccaaatcc | 180 |
| tctggaagca cttccagatc attacaagcc ttggatggaa attgccctca gacttcctca | 240 |
| cttaatcgag aaccgccagc tccgagctca cgtgtacagg atgcctctcc tggactgcag | 300 |
| attcctaaag agttaccgtg agcagcgcct ggcacacatg cgctggccg ctatcaccat | 360 |
| gggattcgtc tggcaggagg gggaaggcca accccaaaag gtgctgccaa gatctcttgc | 420 |
| cattcctttt gttgaggtat ccaggaactt gggactcccg cctatcctgg tccactctga | 480 |
| cctggtgctg acaaactgga ccaaaaggaa cccagaagga ccgttggaaa tcagtaacct | 540 |
| ggaaaccatc atctcatttc cggggggaga gagcctgcgg ggcttcatcc tagtgacagt | 600 |
| cttggtggag aaggcagcag tgcccggcct taaggccctg gttcagggaa tggaggccat | 660 |
| tcggcaacac agtcaggaca ccctgctaga agccctgcag cagctgagac tctccatcca | 720 |
| ggatatcacc agagccttgg cccaaatgca tgattatgtg gacccagaca tattttactc | 780 |
| ggtcatccgg atcttcctct ctgggtggaa ggacaatcca gccatgcctg tggggctggt | 840 |
| ctatgaaggt gttgccacag agcctctgaa gtactctgga ggaagtgcag cccagagctc | 900 |
| cgtgcttcat gccttcgatg agttcctggg cattgagcat tgcaaggaaa gtgttggctt | 960 |
| tctacacaga atgagggact acatgccgcc ttcccataag gctttcctgg aagatctcca | 1020 |
| cgtagctcct tctctgagag actacatact ggcctctggt cctggggact gctgatggc | 1080 |
| ctataaccag tgtgtggagg ccctgggaga gctgcgcagt taccacatca atgtcgtggc | 1140 |
| cagatacatt atctccgctg ccaccagggc caggagcagg gggctaacta atccctcacc | 1200 |
| ccatgccttg gaagacaggg gcactggggg tactgccatg ctgagcttct tgaagagtgt | 1260 |
| cagggagaag accatggagg ccctcctgtg tcctggtgct tagcagtcat gtcctgcacc | 1320 |
| ctaacactta gatgttctca tcctgcatcc cagcgttaga ggttcacatc ctgcatccta | 1380 |

```
gtgcttagct gttcttgtgc tatatcccag cgcttagcag tcatgtcctg catcctagtg    1440
cttagcattt tatatccagc atcttagtgc ttagagattc acatcctgca tcctagagct    1500
tagcatttta tatccagcat ccttgtgcgt atcagctatg ttttgtatcc tgcttagcag    1560
ttaacatcct gcatcctagt acttatctgt tctcatcctg catcctagag cttagcagtc    1620
aggtcccgtg ggagcaagaa ccagggtctg agctctgtct gagcccaagc atggctttac    1680
tgctttgtta ttgtggctc ccacctccac cccaccccag ccagtttgct tgctagaagc     1740
ctttctgcac tgcctaatcc ccctgcctca cagcagagag ctgcagccat gacctcctca    1800
ttcagtatta ggtggacaag tcggagatac ccaaactcaa ttttaaaaga atcaagttgc    1860
ttttggggca tgttacttca tcttttctta ccctgggcct cttcccttct tccctacctc    1920
cctcgtccct tagtctttca cccctctctc tttctccttt tgtcaccctc cccctcccct    1980
gcttactctc ttttcccttc cccctctcc tcatccctcc ttcctttctt ccttcccttt     2040
ttgtctgtga agcaccaggt ctgatgggcc tcaaactgtg atcttcctgt ctcacccttc    2100
aaaggttatg tgtatgtgac gtgtgtgtgt gtgtgtgtgt gtgtgtgtgt gtgtgtgtgt    2160
tcgtttcttt tgttttttccc tagtggagat gacacccaaa gatttgcaca taccaggcaa   2220
ttgctccacc acctgactac agtcccagct ctctgtattc ctgaaggaaa gtcttgatga    2280
gttgcctagg ctggtattga gctctttagc ccaggcaggc cttagtctga gtagctggga   2340
tgtacaggga tgagccactg agccatgctg ctgctgctaa cgatgatgac gatgatgatg   2400
atgaagatta tgataactac agtcactgca ataatgacgg caaagataat gatggctgtc   2460
tcttcccttt tttgttattt tatttttttat tttaatttac tttaagacag tatcctacta   2520
tgctttagtc caggttgcct tgaactacct cagcctcccc agtgcttaga ttatactcat    2580
gaaccaccaa ggctggctct agattctttc aattcactaa gccctactgt gctcttgtct    2640
gtgacctggg acagccttcc cctccatgcc caggctgaat tcagcactgg gggtgggggt   2700
ggggttagat gctgagtgga gatttgtggg gttaaagatg ctgtccatgc agacctggaa   2760
gtcaccagca cgggagctat cagctactga ctaggaaccc gatgcgactc ccccacagag   2820
ggtagacatt gtcggttcta ttttaactct ctctgttcta tttttaggac cgtgtttttc    2880
tttctcctag tgacactgga aatttgtatg tgaaaaatgc tttaactgac cccttgaaag   2940
ccagtaagcc aaaataagaa taaatagtaa gtccacatgt ttaggataaa aataaatatg   3000
gcttttatat ccga                                                      3014

<210> SEQ ID NO 400
<211> LENGTH: 2294
<212> TYPE: DNA
<213> ORGANISM: Homo sapiens

<400> SEQUENCE: 400
agtccagatg atagttaaga aagcagtaag aatacagaga gtccacaatg agatgaaaat      60
gcactgccag ttgaaacatc ctcctacact ggagctttat aaatatttta aagacaagga    120
ttggattaga tttgacatta gaaatgtacc ataatacaga aggcaatgga cacctaaaga    180
acagaatgaa aaccttctta ggaaatgaag cttgacactt cacccaccag gccaccacaa    240
gaatgttgca ttttcattat tatgatactt caaacaaaat aatggagccc cacagaccga    300
atgtgaagac agcagtgcca ttgtctttgg aaagctatca catatctgaa gagtatggct    360
ttcttcttcc agattctctg aaagaacttc cagatcatta taggccttgg atggaaattg    420
```

| | |
|---|---|
| ccaacaaact tcctcaattg attgatgctc accagcttca agctcatgtg acaagatgc | 480 |
| ccctgctgag ctgccagttc ctgaagggtc accgggagca gcgcctggcc cacctggtcc | 540 |
| tgagcttcct caccatgggt tatgtctggc aggaaggaga ggcgcagcct gcagaggtcc | 600 |
| tgccaaggaa tcttgccctt ccatttgtcg aagtctccag gaacttgggg ctccctccta | 660 |
| tcctggtcca ctcagacttg gtgctgacga actggaccaa aaaagatcca gacggattcc | 720 |
| tggaaattgg gaacctggag accatcatct catttcctgg gggagagagc ctgcatggtt | 780 |
| ttatactggt gactgctttg gtagagaaag aagcagtgcc tgggataaag gctcttgttc | 840 |
| aggccacgaa tgctatcttg cagcccaacc aggaggccct gctccaagcc ctgcagcgac | 900 |
| tgagactgtc tattcaggac atcaccaaaa ccttaggaca gatgcatgat tatgtagatc | 960 |
| cagacatatt ttatgcaggc atccggatct ttctctctgg atggaaagac aacccagcaa | 1020 |
| tgcctgcagg gctgatgtat gaaggagttt cccaagagcc cctgaaatac tccggcggga | 1080 |
| gtgcagctca gagcacagtg cttcatgcct tgatgagtt cttaggcatt cgtcatagca | 1140 |
| aggaaagtgg tgactttctg tacagaatga gggattacat gcctccttcc cataaggcct | 1200 |
| tcatagaaga catccactca gcaccttccc tgagggacta catcctgtca tctggacagg | 1260 |
| accacttgct gacagcttat aaccagtgtg tgcaggccct ggcagagctg cggagctatc | 1320 |
| acatcaccat ggtcaccaaa tacctcatca cagctgcagc caaggcaaag catgggaagc | 1380 |
| caaaccatct cccagggcct cctcaggctt aaaagacag gggcacaggt ggaaccgcag | 1440 |
| ttatgagctt tcttaagagt gtcagggata agaccttgga gtcaatcctt cacccacgtg | 1500 |
| gttaggaggc tgccctctcc ccagcaatgc agagccccca tggagggcag gtgggcctgg | 1560 |
| agaatgaggg tcagggttct gcctgggatc atccaggaag gatctcagcc ctattcatgt | 1620 |
| ttctgctcta cagagcacta tattctcctt gttgagagct gttggcttca caaggagag | 1680 |
| ttgatgtggc caagcctttc cctccctacc tgatcactgc ttaacggcat gtataatgga | 1740 |
| tacttcctca tgcagaaccc ccagaggagt gactgtatgc cattctcttt gccaagtaat | 1800 |
| agaaaaccaa tctaaatgtc aaaaatcaga taaaattgcc tggggataca ttacttgttg | 1860 |
| attttcttaa aaaacaaatt cacttaacaa ttcattaagt tcatactgag cactgcctcc | 1920 |
| aagattaaaa ccaggatttc tgtggtccca gccagccct cttctccctg aatgtgttga | 1980 |
| gttggtggca ggaggttgga aatgctccag tggagatggg aagatagagg atgctgacaa | 2040 |
| taaggacttg gaagtcacta gtgtgaaaat gagcagttaa tgatatggga acggatgaga | 2100 |
| cttccacgt ggtacctaga tttgcaaatt ctattgtaat gcctttattt ttagaagaat | 2160 |
| tattctctct tcttactctg aaaatctgta tttgtaaaat gaatgaatgg atcctatata | 2220 |
| agtaaataag aaaactggga ataagtagta aatcaatgtg tttagtgtgc aaataaatgt | 2280 |
| aaatgctttt attg | 2294 |

<210> SEQ ID NO 401
<211> LENGTH: 3143
<212> TYPE: DNA
<213> ORGANISM: Mus musculus

<400> SEQUENCE: 401

| | |
|---|---|
| aaagctccctt taagaaaagc agggcagata tcagggcagc ctggcttagc agtagtgttg | 60 |
| gagaagaagc tagcaggcag gcagcagaga catggagctg gcctcagcac atctccacaa | 120 |
| agggcaggtt ccctggggag gactactgct cacagcctca cttttagcct cctggagccc | 180 |
| tgccaccact gctgaagtca ccattgaggc tgtgccgccc caggttgctg aagacaacaa | 240 |

```
tgttcttcta cttgttcaca atctgcccct ggcgcttgga gcctttgcct ggtacaaggg        300
aaacactacg gctatagaca aagaaattgc acgatttgta ccaaatagta atatgaattt        360
cacggggcaa gcatacagcg gcagagagat aatatacagc aatggatccc tgctcttcca        420
aatgatcacc atgaaggata tgggagtcta cacactagat atgacagatg aaaactatcg        480
tcgtactcag gcgactgtgc gatttcatgt acaccagcca gtgactcagc ccttcctcca        540
agtcaccaac accacagtca aagaactaga ctctgtgacc ctgacctgct tgtcgaatga        600
cattggagcc aacatccagt ggctcttcaa tagccagagt cttcagctca cagagagaat        660
gacactctcc cagaacaaca gcatcctcag aatagaccct attaagaggg aagatgccgg        720
cgagtatcag tgtgaaatct cgaatccagt cagcgtcagg aggagcaact caatcaagct        780
ggacataata tttgacccaa cacaaggagg cctctcagat ggcgccattg ctggcatcgt        840
gattggagtt gtggctgggg tggctctaat agcagggctg gcatatttcc tctattccag        900
gaagtctggc ggatctggct ccttctgaca actctcctaa caaggtggat gacgtcgcat        960
acactgtcct gaacttcaat tcccagcaac ccaaccggcc aacttcagcc ccttcttctc       1020
caagagccac agaaacagtt tattcagaag taaaaaagaa gtgagcataa tctgtccgtc       1080
tgtcctgctg gctgcaccag tgatgcattc ccggattctg ttcctcactg gagggtctca       1140
gcacacacac acacgtacac atgcgcgcgc gcacacacac acacacacac acacacacac       1200
acttacacac acactcatgc attcactcta ttgactcctt cagtgtctat agaagaaaag       1260
gtggatcctg gagcctacag aaaactcaac ccttctaggc tttcaaattt ggctgagagt       1320
gaggtatcaa aatttctcac cctttcactt tcctgaccca gattgttgaa aattgaccta       1380
ttcagagcac cttcattccc ctcccaactc caagtcctgc cctatcagag tctgacttga       1440
atttccataa accttggagg tcacctaagt gcttacgcca acaaaacaa aacaaaacaa       1500 aacaaaacaa aacaaaacaa aacaaaacaa accagaagca ggaaatggcc agtcccatat       1560
ctttaaaggc tgattggaag ccaccataca tgagaagatc aaacctccat gggcaatcta       1620
cacacccgac aactgtcatg cttacccatc tgggacattc gagtctctga accttgtgcc       1680
ctcacgcctg agcccttctc tgagcctttc tccagaaaat ccactcacag caactagaga       1740
ggctctttgt cagcaactcc aagcaaactg ctaggcagga ttcagaagaa aagacagcat       1800
ctctaacatc caccaggaag gtgcccagaa aagcagagct ggtgactttg gactgacaga       1860
catctggagt gtgaaaaagc agcacagagc taaccttcgg agagtgttga aattatttga       1920
aaagaagcca tatttggagg tattggagtt ttcctctttc tgagacaatc cactatttga       1980
aaattgtagc tactgaattg cctctcagta tgcgagctga tcactttgcc ttagggccac       2040
tagatttctg tctcccttag cccctcaagc ccttttgatc atgagttcca aaccaaaaat       2100
aaataaatga acagtgaggc agtcccttgc agtaccactg tcatgggtca ggctaagcct       2160
cctgcttttc tgaattagtc aagaaaagcc ttggtttccc ttttccatc tctttatctt       2220 gtctttcaga tactggccag agcctggaca ctcttcctct gagatctcca gcttctctgc       2280
cttcttgtgt ttctttaaa ctctaacaaa aactgttctc accttcaaaa aataaaataa       2340
taacaagctt tccacatccc caccaaagag ggacccagct aggttctgg aaacccagca       2400 ccagcctcca gctgcccttc tgcagtgttt ctgcctctgt ttcccttctg ttttgacttt       2460
tttccttctt ttgagacaga gttccagcat ggagcctgtg caggtttcaa tcccacagta       2520
acaccttctg cagcaccca cctgctcaga ctgcagccct ggccaccagg cctggctacc       2580
```

```
tggacattct gtctgccctg cactctcagg aaaccttggc ctctgctact gtctgtttgg    2640
ctcattcaaa gtgtgtcctt aaaggaatgc agtcacccat gccagaggca gtgtttacag    2700
cctggaatgc tctgcacttc cagtggacca gtgctccacc ggaagtgggc tgttagcagg    2760
gtcctctcac ctggccctgg cctttctgta gccttgaatc ctgccttccc caccagggca    2820
ccagggatga gtgcagcagc aggaggagag gcaaacagtc acctcaggaa ccttctgagc    2880
taaggcacac cctctgtgcc tgtcaagcaa aggttgtatt ggatatcaag tgtttggtct    2940
cacgccaagc caacaggctt tggagagaat taattagttc tcctactcag ggatttcttt    3000
cagtcctaac acagcctgtg tatattttgc ttcacccacg caatgctgga ttatttaatt    3060
ttgcccggct taagacaaat ctgagttact tgtaaatttg ctctatgttc ataataaaaa    3120
tgtattatat atcactgata gca                                            3143

<210> SEQ ID NO 402
<211> LENGTH: 3470
<212> TYPE: DNA
<213> ORGANISM: Homo sapiens

<400> SEQUENCE: 402
aaagctctgg gccccaggga ggaggctcag cacagagagt ggaaaacagc agaggtgaca      60
gagcagccgt gctcgaagcg ttcctggagc ccaagctctc ctccacaggt gaagacaggg     120
ccagcaggag acaccatggg gcacctctca gccccacttc acagagtgcg tgtaccctgg     180
caggggcttc tgctcacagc ctcacttcta accttctgga acccgcccac cactgcccag     240
ctcactactg aatccatgcc attcaatgtt gcagagggga aggaggttct tctccttgtc     300
cacaatctgc cccagcaact ttttggctac agctggtaca aggggaaag agtggatggc     360 aaccgtcaaa ttgtaggata tgcaatagga actcaacaag ctaccccagg gcccgcaaac     420
agcggtcgag agacaatata ccccaatgca tccctgctga tccagaacgt cacccagaat     480
gacacaggat tctacaccct acaagtcata aagtcagatc ttgtgaatga agaagcaact     540
ggacagttcc atgtataccc ggagctgccc aagccctcca tctccagcaa caactccaac     600
cctgtggagg acaaggatgc tgtggccttc acctgtgaac ctgagactca ggacacaacc     660
tacctgtggt ggatcaacaa tcagagcctc ccggtcagtc ccaggctgca gctgtccaat     720
ggcaacagga ccctcactct actcagtgtc acaaggaatg acacaggacc ctatgagtgt     780
gaaatacaga acccagtgag tgcgaaccgc agtgacccag tcaccttgaa tgtcacctat     840
ggcccggaca cccccaccat ttccccttca gacacctatt accgtccagg gcaaacctc     900 agcctctcct gctatgcagc ctctaaccca cctgcacagt actcctggct tatcaatgga     960
acattccagc aaagcacaca agagctcttt atccctaaca tcactgtgaa taatagtgga    1020
tcctatacct gccacgccaa taactcagtc actggctgca caggaccac agtcaagacg    1080 atcatagtca ctgagctaag tccagtagta gcaaagcccc aaatcaaagc cagcaagacc    1140
acagtcacag gagataagga ctctgtgaac ctgacctgcc cacaaatga cactggaatc    1200 tccatccgtt ggttcttcaa aaaccagagt ctcccgtcct cggagaggat gaagctgtcc    1260
cagggcaaca cccacctcag cataaaccct gtcaagaggg aggatgctgg gacgtattgg    1320
tgtgaggtct tcaacccaat cagtaagaac caaagcgacc ccatcatgct gaacgtaaac    1380
tataatgctc taccacaaga aaatggcctc tcacctgggg ccattgctgg cattgtgatt    1440
ggagtagtgg ccctggttgc tctgatagca gtagccctgg catgttttct gcatttcggg    1500
aagaccggca ggaccactcc aatgacccac taacaagat gaatgaagtt acttattcta    1560
```

-continued

```
ccctgaactt tgaagcccag caacccacac aaccaacttc agcctcccca tccctaacag    1620
ccacagaaat aatttattca gaagtaaaaa agcagtaatg aaacctgtcc tgctcactgc    1680
agtgctgatg tatttcaagt ctctcaccct catcactagg agattccttt ccctgtagg     1740 ggtagagggg tggggacaga aacaactttc tcctactctt ccttcctaat aggcatctcc    1800
aggctgcctg gtcactgccc ctctctcagt gtcaatagat gaaagtacat gggagtctg     1860 taggaaaccc aaccttcttg tcattgaaat ttggcaaagc tgactttggg aaagagggac    1920
cagaacttcc cctcccttcc ccttttccca acctggactt gttttaaact tgcctgttca    1980
gagcactcat tccttcccac ccccagtcct gtcctatcac tctaattcgg atttgccata    2040
gccttgaggt tatgtccttt tccattaagt acatgtgcca ggaaacaaga gagagagaaa    2100
gtaaaggcag taatgccttc tcctatttct ccaaagcctt gtgtgaactc accaaacaca    2160
agaaaatcaa atatataacc aatagtgaaa tgccacacct ttgtccactg tcagggttgt    2220
ctacctgtag gatcagggtc taagcacctt ggtgcttagc tagaatacca cctaatcctt    2280
ctggcaagcc tgtcttcaga gaacccacta gaagcaacta ggaaaatcac ttgccaaaat    2340
ccaaggcaat tcctgatgga aaatgcaaaa gcacatatat gttttaatat ctttatgggc    2400
tctgttcaag gcagtgctga gagggagggg ttatagcttc aggagggaac cagcttctga    2460
taaacacaat ctgctaggaa cttgggaaag gaatcagaga gctgcccttc agcgattatt    2520
taaattattg ttaaagaata cacaatttgg ggtattggga tttttctcct tttctctgag    2580
acattccacc atttttaattt ttgtaactgc ttatttatgt gaaagggtt attttttactt    2640 agcttagcta tgtcagccaa tccgattgcc ttaggtgaaa gaaaccaccg aaatccctca    2700
ggtcccttgg tcaggagcct ctcaagattt tttttgtcag aggctccaaa tagaaaataa    2760
gaaaaggttt tcttcattca tggctagagc tagatttaac tcagtttcta ggcacctcag    2820
accaatcatc aactaccatt ctattccatg tttgcacctg tgcattttct gtttgccccc    2880
attcactttg tcaggaaacc ttggcctctg ctaaggtgta tttggtcctt gagaagtggg    2940
agcaccctac agggacacta tcactcatgc tggtggcatt gtttacagct agaaagctgc    3000
actggtgcta atgccccttg gggaaatggg gctgtgagga ggaggattat aacttaggcc    3060
tagcctcttt taacagcctc tgaaatttat cttttcttct atggggtcta taaatgtatc    3120
ttataataaa aaggaaggac aggaggaaga caggcaaatg tacttctcac ccagtcttct    3180
acacagatgg aatctctttg gggctaagag aaaggtttta ttctatattg cttacctgat    3240
ctcatgttag gcctaagagg cttttctccag gaggattagc ttggagttct ctatactcag    3300
gtacctcttt cagggttttc taaccctgac acggactgtg catactttcc ctcatccatg    3360
ctgtgctgtg ttatttaatt tttcctggct aagatcatgt ctgaattatg tatgaaaatt    3420
attctatgtt tttataataa aaataatata tcagacatcg aaaaaaaaaa               3470
```

<210> SEQ ID NO 403
<211> LENGTH: 1155
<212> TYPE: DNA
<213> ORGANISM: Mus musculus

<400> SEQUENCE: 403

```
ccaaagcact tcttagctta tcatgggact ctgcatacgc ctgtgccaaa tacacaggaa     60
cacgttcaca tacctccttg cctgtccgcc tactcttctt gccccacctc catagttctt    120
atagccacac cctgcaagga aaaccccag actcctgtga aggcagaaag cagacaagga    180
```

```
tgtatgtgtg ggttcagcag cccacagccc ttctgctgct gggactcaca cttggagtta      240
cagcaaggcg gctcaactgt gttaaacata cctacccag tggtcacaag tgctgtcgtg       300
agtgccagcc aggccatggt atggtgagcc gctgtgatca taccagggat actctatgtc     360
atccgtgtga gactggcttc tacaatgaag ctgtcaatta tgatacctgc aagcagtgta      420
cacagtgcaa ccatcgaagt ggaagtgaac tcaagcagaa ttgcacacct actcaggata     480
ctgtctgcag atgtagacca ggcacccaac ctcggcagga cagcggctac aagcttggag      540
ttgactgtgt tccctgccct cctggccact tttctccagg caacaaccag gcctgcaagc     600
cctggaccaa ttgtaccttta tctggaaagc agaccccgcca cccagccagt gacagcttgg    660
acgcagtctg tgaggacaga agcctcctgg ccacactgct ctgggagacc cagcgcccta     720
cattcaggcc aaccactgtc caatccacca cagtctggcc caggacttct gagttgccct     780
ctccacccac cttggtgact cctgagggcc ctgcatttgc tgttctccta ggcctgggcc     840
tgggcctgct ggctcccttg actgtcctgc tggccttgta cctgctccgg aaggcttgga     900
gattgcctaa cactcccaaa ccttgttggg gaaacagctt caggacccg atccaggagg      960 aacacacaga cgcacacttt actctggcca agatctgagc attactacag gagtggattt   1020
tatggggcac ggacaaccca tatcctgatg cctgccagta cctccacac cgttctaggt    1080 gctgggctgg ctctgggctt tcctatgtat gctatgcata ctacctgcct ggtggtgctc   1140
ctaataaaca tgcta                                                  1155

<210> SEQ ID NO 404
<211> LENGTH: 1120
<212> TYPE: DNA
<213> ORGANISM: Homo sapiens

<400> SEQUENCE: 404
ccgcaaggaa aacccagact ctggcgacag cagagacgag gatgtgcgtg ggggctcggc      60
ggctgggccg cgggccgtgt gcggctctgc tcctcctggg cctggggctg agcaccgtga     120
cggggctcca ctgtgtcggg gacacctacc ccagcaacga ccggtgctgc cacgagtgca     180
ggccaggcaa cgggatggtg agccgctgca gccgctccca gaaacgcgtg tgccgtccgt     240
gcgggccggg cttctacaac gacgtggtca gctccaagcc gtgcaagccc tgcacgtggt     300
gtaacctcag aagtgggagt gagcggaagc agctgtgcac ggccacacag acacagtct     360 gccgctgccg ggcgggcacc cagcccctgg acagctacaa gcctggagtt gactgtgccc     420
cctgccctcc agggcactttc tccccaggcg acaaccaggc ctgcaagccc tggaccaact     480
gcaccttggc tgggaagcac accctgcagc cggccagcaa tagctcggac gcaatctgtg     540
aggacaggga ccccccagcc acgcagcccc aggagaccca gggcccccg gccaggccca     600 tcactgtcca gcccactgaa gcctggccca gaacctcaca gggaccctcc acccggcccg     660
tggaggtccc cggggccgt gcggttgccg ccatcctggg cctgggcctg gtgctggggc     720
tgctgggccc cctggccatc ctgctggccc tgtacctgct ccggagggac agaggctgc     780 cccccgatgc ccacaagccc cctggggag gcagtttccg gaccccatc aagaggagc      840 aggccgacgc ccactccacc ctggccaaga tctgacctgg gccaccaag gtggacgctg     900 ggccccgcca ggctggagcc cggagggtct gctgggcgag cagggcaggt gcaggccgcc     960
tgccccgcca cgctcctggg ccaactctgc accgttctag gtgccgatgg ctgcctccgg   1020
ctctctgctt acgtatgcca tgcataccct ctgccccgcg ggaccacaat aaaaaccttg   1080
gcagacggga gtctccgacc ggcaaaaaaa aaaaaaaaa                          1120
```

<210> SEQ ID NO 405
<211> LENGTH: 1609
<212> TYPE: DNA
<213> ORGANISM: Mus musculus

<400> SEQUENCE: 405

| | | | | | | |
|---|---|---|---|---|---|---|
| attgcttttt | gtctcctgtt | ctgggacctt | tatcttctga | cccgcaggct | tgactttgcc | 60 |
| cttattggct | cctttgtggt | gaagagcagt | cttcccccag | gttccccgcc | acagctgtat | 120 |
| ctcctctgca | ccccgactgc | agagatggaa | ggggaagggg | ttcaaccoct | ggatgagaat | 180 |
| ctggaaaacg | gatcaaggcc | aagattcaag | tggaagaaga | cgctaaggct | ggtggtctct | 240 |
| gggatcaagg | gagcagggat | gcttctgtgc | ttcatctatg | tctgcctgca | actctcttcc | 300 |
| tctccggcaa | aggaccctcc | aatccaaaga | ctcagaggag | cagttaccag | atgtgaggat | 360 |
| gggcaactat | tcatcagctc | atacaagaat | gagtatcaaa | ctatggaggt | gcagaacaat | 420 |
| tcggttgtca | tcaagtgcga | tgggctttat | atcatctacc | tgaagggctc | cttttccag | 480 |
| gaggtcaaga | ttgaccttca | tttccgggag | gatcataatc | ccatctctat | tccaatgctg | 540 |
| aacgatggtc | gaaggattgt | cttcactgtg | gtggcctctt | tggctttcaa | agataaagtt | 600 |
| tacctgactg | taaatgctcc | tgatactctc | tgcgaacacc | tccagataaa | tgatggggag | 660 |
| ctgattgttg | tccagctaac | gcctggatac | tgtgctcctg | aaggatctta | ccacagcact | 720 |
| gtgaaccaag | taccactgtg | aattccactc | tgagggtgga | cgggacacag | gttctttctc | 780 |
| gagagagatg | agtgcatcct | gctcatgaga | tgtgactgaa | tgcagagcct | accctacttc | 840 |
| ctcactcagg | gatatttaaa | tcatgtctta | cataacagtt | gacctctcat | tcccaggatt | 900 |
| gccttgagcc | tgctaagagc | tgttctggga | atgaaaaaaa | aaataaatgt | ctcttcaaga | 960 |
| cacattgctt | ctgtcggtca | gaagctcatc | gtaataaaca | tctgccactg | aaaatggcgc | 1020 |
| ttgattgcta | tcttctagaa | ttttgatgtt | gtcaaaagaa | agcaaaacat | ggaaagggtg | 1080 |
| gtgtccaccg | gccagtagga | gctggagtgc | tctcttcaag | gttaaggtga | tagaagttta | 1140 |
| catgttgcct | aaaactgtct | ctcatctcat | gggggcttg | gaaagaagat | taccccgtgg | 1200 |
| aaagcaggac | ttgaagatga | ctgtttaagc | aacaaggtgc | actcttttcc | tggcccctga | 1260 |
| atacacataa | aagacaactt | ccttcaaaga | actacctagg | gactatgata | cccaccaaag | 1320 |
| aaccacgtca | gcgatgcaaa | gaaaaccagg | agagctttgt | ttattttgca | gagtatacga | 1380 |
| gagattttac | cctgagggct | attttttatta | tacaggatga | gagtgaactg | gatgtctcag | 1440 |
| gataaaggcc | aagaaggatt | tttcacagtc | tgagcaagac | tgttttttgta | ggttctctct | 1500 |
| ccaaaacttt | taggtaaatt | tttgataatt | ttaaaatttt | tagttatatt | tttggaccat | 1560 |
| tttcaataga | agattgaaac | atttccagat | ggtttcatat | ccccacaag | | 1609 |

<210> SEQ ID NO 406
<211> LENGTH: 3484
<212> TYPE: DNA
<213> ORGANISM: Homo sapiens

<400> SEQUENCE: 406

| | | | | | | |
|---|---|---|---|---|---|---|
| ggccctggga | cctttgccta | ttttctgatt | gataggcttt | gttttgtctt | tacctccttc | 60 |
| tttctgggga | aaacttcagt | tttatcgcac | gttcccctttt | tccatatctt | catcttccct | 120 |
| ctacccagat | tgtgaagatg | gaagggtcc | aaccctgga | agagaatgtg | ggaaatgcag | 180 |
| ccaggccaag | attcgagagg | aacaagctat | tgctggtggc | ctctgtaatt | cagggactgg | 240 |

```
ggctgctcct gtgcttcacc tacatctgcc tgcacttctc tgctcttcag gtatcacatc      300
ggtatcctcg aattcaaagt atcaaagtac aatttaccga atataagaag gagaaaggtt      360
tcatcctcac ttcccaaaag gaggatgaaa tcatgaaggt gcagaacaac tcagtcatca      420
tcaactgtga tgggttttat ctcatctccc tgaagggcta cttctcccag gaagtcaaca      480
ttagccttca ttaccagaag gatgaggagc ccctcttcca actgaagaag gtcaggtctg      540
tcaactcctt gatggtggcc tctctgactt acaaagacaa agtctacttg aatgtgacca      600
ctgacaatac ctccctggat gacttccatg tgaatggcgg agaactgatt cttatccatc      660
aaaatcctgg tgaattctgt gtcctttgag gggctgatgg caatatctaa aaccaggcac      720
cagcatgaac accaagctgg gggtggacag ggcatggatt cttcattgca agtgaaggag      780
cctcccagct cagccacgtg ggatgtgaca agaagcagat cctggccctc ccgcccccac      840
ccctcaggga tatttaaaac ttattttata taccagttaa tcttatttat ccttatattt      900
tctaaattgc ctagccgtca cacccccaaga ttgccttgag cctactaggc acctttgtga      960
gaaagaaaaa atagatgcct cttcttcaag atgcattgtt tctattggtc aggcaattgt     1020
cataataaac ttatgtcatt gaaaacggta cctgactacc atttgctgga aatttgacat     1080
gtgtgtggca ttatcaaaat gaagaggagc aaggagtgaa ggagtggggt tatgaatctg     1140
ccaaaggtgg tatgaaccaa cccctggaag ccaaagcggc ctctccaagg ttaaattgat     1200
tgcagtttgc atattgccta aatttaaact ttctcatttg gtggggttc aaaagaagaa     1260 tcagcttgtg aaaaatcagg acttgaagag agccgtctaa gaaataccac gtgctttttt     1320
tctttaccat tttgctttcc cagcctccaa acatagttaa tagaaatttc ccttcaaaga     1380
actgtctggg gatgtgatgc tttgaaaaat ctaatcagtg acttaagaga gatttttcttg     1440 tatacaggga gagtgagata acttattgtg aagggttagc tttactgtac aggatagcag     1500
ggaactggac atctcagggt aaaagtcagt acggatttta atagcctggg gaggaaaaca     1560
cattctttgc cacagacagg caaagcaaca catgctcatc ctcctgccta tgctgagata     1620
cgcactcagc tccatgtctt gtacacacag aaacattgct ggtttcaaga aatgaggtga     1680
tcctattatc aaattcaatc tgatgtcaaa tagcactaag aagttattgt gccttatgaa     1740
aaataatgat ctctgtctag aaataccata gaccatatat agtctcacat tgataattga     1800
aactagaagg gtctataatc agcctatgcc agggcttcaa tggaatagta tcccccttatg     1860 tttagttgaa atgtccccctt aacttgatat aatgtgttat gcttatggcg ctgtggacaa     1920
tctgattttt catgtcaact ttccagatga tttgtaactt ctctgtgcca aaccttttat     1980
aaacataaat ttttgagata tgtattttaa aattgtagca catgtttccc tgacattttc     2040
aatagaggat acaacatcac agaatctttc tggatgattc tgtgttatca aggaattgta     2100
ctgtgctaca attatctcta gaatctccag aaaggtggag ggctgttcgc ccttacacta     2160
aatggtctca gttggatttt ttttttcctgt tttctatttc ctcttaagta caccttcaac     2220
tatattccca tccctctatt ttaatctgtt atgaaggaag gtaaataaaa atgctaaata     2280
gaagaaattg taggtaaggt aagaggaatc aagttctgag tggctgccaa ggcactcaca     2340
gaatcataat catggctaaa tatttatgga gggcctactg tggaccaggc actgggctaa     2400
atacttacat ttacaagaat cattctgaga cagatattca atgatatctg gcttcactac     2460
tcagaagatt gtgtgtgtgt ttgtgtgtgt gtgtgtgtgt gtatttcact ttttgttatt     2520
gaccatgttc tgcaaaattg cagttactca gtgagtgata tccgaaaaag taaacgttta     2580
tgactatagg taatatttaa gaaaatgcat ggttcatttt taagtttgga attttttatct     2640
```

```
atatttctca cagatgtgca gtgcacatgc aggcctaagt atatgttgtg tgtgttgttt    2700
gtctttgatg tcatggtccc ctctcttagg tgctcactcg ctttgggtgc acctggcctg    2760
ctcttcccat gttggcctct gcaaccacac agggatattt ctgctatgca ccagcctcac    2820
tccaccttcc ttccatcaaa aatatgtgtg tgtgtctcag tccctgtaag tcatgtcctt    2880
cacagggaga attaaccctt cgatatacat ggcagagttt tgtgggaaaa gaattgaatg    2940
aaaagtcagg agatcagaat tttaaatttg acttagccac taactagcca tgtaaccttg    3000
ggaaagtcat ttcccatttc tgggtcttgc ttttctttct gttaaatgag aggaatgtta    3060
aatatctaac agtttagaat cttatgctta cagtgttatc tgtgaatgca catattaaat    3120
gtctatgttc ttgttgctat gagtcaagga gtgtaacctt ctcctttact atgttgaatg    3180
tatttttttc tggacaagct tacatcttcc tcagccatct ttgtgagtcc ttcaagagca    3240
gttatcaatt gttagttaga tattttctat ttagagaatg cttaagggat tccaatcccg    3300
atccaaatca taatttgttc ttaagtatac tgggcaggtc ccctatttta agtcataatt    3360
ttgtatttag tgctttcctg gctctcagag agtattaata ttgatattaa taatatagtt    3420
aatagtaata ttgctattta catggaaaca aataaaagat ctcagaattc actaaaaaaa    3480
aaaa                                                                 3484
```